(12) United States Patent
Andersen et al.

(10) Patent No.: US 8,765,130 B2
(45) Date of Patent: Jul. 1, 2014

(54) ANTAGONISTIC DR3 LIGANDS

(71) Applicant: Novo Nordisk A/S, Bagsvaerd (DK)

(72) Inventors: Mette Dahl Andersen, Vaerloese (DK);
Peder Lisby Noerby, Birkeroed (DK);
Kristian Kjaergaard, Ballerup (DK);
Susanne Nedergaard Grell, Soeborg (DK); Albrecht Gruhler, Frederikssund (DK); Jens Buchardt, Gentofte (DK);
Henrik Sune Andersen, Holte (DK);
Soeren Padkjaer, Vaerloese (DK);
Jesper Kastrup, Stenloese (DK);
Katarina Haakansson, Bagsvaerd (DK); Lars Hornum, Bagsvaerd (DK);
Birgitte Friedrichsen, Gentofte (DK);
Dorrit Baunsgaard, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/974,275

(22) Filed: Aug. 23, 2013

(65) Prior Publication Data

US 2013/0336984 A1    Dec. 19, 2013

Related U.S. Application Data

(63) Continuation of application No. 13/982,617, filed as application No. PCT/EP2012/053539 on Mar. 1, 2012.

(60) Provisional application No. 61/448,827, filed on Mar. 3, 2011.

(30) Foreign Application Priority Data

Mar. 1, 2011   (EP) .................................. 11156416

(51) Int. Cl.
*A61K 39/395*    (2006.01)
*C07K 16/28*    (2006.01)
*C07K 14/705*    (2006.01)
*A61K 39/00*    (2006.01)

(52) U.S. Cl.
CPC ........ *C07K 16/2878* (2013.01); *C07K 14/70578* (2013.01); *A61K 2039/505* (2013.01); *C07K 2317/24* (2013.01); *C07K 2317/34* (2013.01); *C07K 2317/55* (2013.01); *C07K 2317/75* (2013.01); *C07K 2317/76* (2013.01); *C07K 2317/94* (2013.01); *C07K 2317/73* (2013.01); *C07K 2317/92* (2013.01)
USPC ...................................................... 424/144.1

(58) Field of Classification Search
None
See application file for complete search history.

(56) References Cited

U.S. PATENT DOCUMENTS

2007/0190607 A1    8/2007   Lenardo et al.

FOREIGN PATENT DOCUMENTS

| WO | 97/33904 A1 | 9/1997 |
|---|---|---|
| WO | 97/37020 A1 | 10/1997 |
| WO | 00/64465 A1 | 11/2000 |
| WO | 01/35995 A2 | 5/2001 |
| WO | 02/40680 A2 | 5/2002 |
| WO | 2007/027751 A2 | 3/2007 |
| WO | 2010/042697 A1 | 4/2010 |
| WO | 2011/106707 A2 | 9/2011 |

OTHER PUBLICATIONS

Novus Biologicals, "DR3 Antibody (H00008718-M07)", 2009, pp. 1-4.
Meylan, F. et al, Mucosal Immunology, "The TNF-Family Cytokine TL1A Drives IL-13-Dependent Small Intestinal Inflammation", 2010, vol. 4, No. 2, pp. 172-185.
Wen L et al., Journal of Biological Chemistry, "TL1A-Induced NF-KAPPA B Activation and C-IAP2 Production Prevent DR3-Mediated Apoptosis in TF-1 Cells", 2003, vol. 278, No. 40, pp. 39251-39258.
Website, Last Modified Feb. 25, 2014 , <http://www.bioinf.org.uk/abs/>.

*Primary Examiner* — Zachary Skelding
(74) *Attorney, Agent, or Firm* — Michael J. Brignati

(57) ABSTRACT

The present invention relates to treatment of inflammatory diseases. In particular, the present invention relates to antagonistic DR3 ligands useful for treating inflammatory diseases.

23 Claims, 13 Drawing Sheets

Fig. 1

SEQ ID NO 1: hDR3 (signal peptide 1-14 and transmembrane domain shown in grey, Death domain (DD) is underlined)
1-417
MEQRPRGCAAVAAALLLVLLGARAQGGTRSPRCDCAGDFHKKIGLFCCRGCPAGHYLKAPCTEP
CGNSTCLVCPQDTFLAWENHHNSECARCQACDEQASQVALENCSAVADTRCGCKPGWFVECQ
VSQCVSSSPFYCQPCLDCGALHRHTRLLCSRRDTDCGTCLPGFYEHGDGCVSCPTSTLGSCPER
CAAVCGWRQMFWVQVLLAGLVVPLLLGATLTYTYRHCWPHKPLVTADEAGMEALTPPPATHLSP
LDSAHTLLAPPDSSEKICTVQLVGNSWTPGYPETQEALCPQVTWSWDQLPSRALGPAAAPTLSPE
SPAGSPAMMLQPGPQLYDVMDAVPARRWKEFVRTLGLREAEIEAVEVEIGRFRDQQYEMLKRW
RQQQPAGLGAVYAALERMGLDGCVEDLRSRLQRGP SEQ ID NO 2:
DR3 (CRD1) – Fc (DR3 region underlined)
QGGTRSPRCDCAGDFHKKIGLFCCRGCPAGHYLKAPCTEPCGNSTCLESKYGPPCPPCPAPEFL
GGPSVFLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSRWQEGNVFSCSVM
HEALHNHYTQKSLSLSLGK SEQ ID NO 3:
DR3 (CRD1+ A1) – Fc (DR3 region underlined)
QGGTRSPRCDCAGDFHKKIGLFCCRGCPAGHYLKAPCTEPCGNSTCLVCPQDTFLAWENHHNS
ECAESKYGPPCPPCPAPEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTPPVLDSDGSFFLYSRL
TVDKSRWQEGNVFSCSVMHEALHNHYTQKSLSLSLGK SEQ ID NO 4:
DR3 (CRD1+CRD2) – Fc (DR3 region underlined)

FIG. 1 (CONTINUED)

<u>QGGTRSPRCDCAGDFHKKIGLFCCRGCPAGHYLKAPCTEPCGNSTCLVCPQDTFLAWENHHNS
ECARCQACDEQASQVALENCSAVADTRCGESKYGPPCPPC</u>PAPEFLGGPSVFLFPPKPKDTLMI
SRTPEVTCVVVDVSQEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHYTQKSLSLSLG
K

SEQ ID NO 5:
DR3 (CRD1+CRD2+A1) – Fc (DR3 region underlined)
<u>QGGTRSPRCDCAGDFHKKIGLFCCRGCPAGHYLKAPCTEPCGNSTCLVCPQDTFLAWENHHNS
ECARCQACDEQASQVALENCSAVADTRCGCKPGWFVECQVSQCVSSSPFYCQESKYGPPCPP
C</u>PAPEFLGGPSVFLFPPKPKDTLMISRTPEVTCVVVDVSQEDPEVQFNWYVDGVEVHNAKTKPRE
EQFNSTYRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRWQEGNV
FSCSVMHEALHNHYTQKSLSLSLGK

SEQ ID NO 6:
GST-hDR3 (CRD1): (DR3 region underlined)
SPILGYWKIKGLVQPTRLLLEYLEEKYEEHLYERDEGDKWRNKKFELGLEFPNLPYYIDGDVKLTQ
SMAIIRYIADKHNMLGGSPKERAEISMLEGAVLDIRYGVSRIAYSKDFETLKVDFLSKLPEMLKMFE
DRLSHKTYLNGDHVTHPDFMLYDALDVVLYMDPMCLDAFPKLVSFKKRIEAIPQIDKYLKSSKYIAW
PLQGWQATFGGGDHPPKSDLVPRGSPEF<u>QGGTRSPRCDCAGDFHKKIGLFCCRGCPAGHYLKA
PCTEPCGNSTCL</u>EFPGRLERPHRD

SEQ ID NO 7:
hDR3-TEV-Fc (DR3 region underlined)
<u>QGGTRSPRCDCAGDFHKKIGLFCCRGCPAGHYLKAPCTEPCGNSTCLVCPQDTFLAWENHHNS
ECARCQACDEQASQVALENCSAVADTRCGCKPGWFVECQVSQCVSSSPFYCQPCLDCGALHR
HTRLLCSRRDTDCGTCLPGFYEHGDGCVSCPTSTLGSCPERCAAVCGWRQENLYFQGESKYGP
CPPC</u>PAPEFLGGPSVFLFPPKPKDTLMISRTPEVTCVVVDVSQEDPEVQFNWYVDGVEVHNAKT
KPREEQFNSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVDKSRWQ
EGNVFSCSVMHEALHNHYTQKSLSLSLGK

FIG. 1 (CONTINUED)

SEQ ID NO 8:

27F16A1: heavy chain – mIgG1 (CDRs marked with bold)

EVQLVESGGDFVKPGGSLKLSCAASGFTFNNYGMSWVRQTPDKRLEWVAAISSGVTYTYYPD TVKGRFTISRDNAKNTLYLHMSSLKSEDTAMYYCGRHDDYGNHFDYWGQGTTLTVSS

SEQ ID NO 9:

27F16A1: light chain – kappa (CDRs marked with bold)

DIVMTQSPSSLAMSLGQRVTMNCKSSQSLLNSHNQKNYLAWYQQKPGQSPKLLVYFASSRE SGVPDRFIGSGSGTDFTLTISSVQAEDLADYFCQQHYSTPFTFGSGTKLEIKR

SEQ ID NO 10:

27F44A2/"0072": heavy chain-mIgG1 (CDRs marked with bold)

EVKLVESGGGLVKPGGSLKLSCSASGFAFSNYDMSWVRQTPEKRLEWVAAFSSDGYTFYPDS LKGRFTISRDNARNTLYLQMSSLGSEDTALYCCARHADYANYPVMDYWGQGTSVTVSS

SEQ ID NO 11:

27F44A2/"0072": light chain-kappa (CDRs marked with bold)

DIVLAQSPASLLVSLGQRATISCRASKSVSTSGYSYMHWYQQKPGQPPKLLIYLASNLESGVP ARFSGSGSGTDFTLNIHPVEEEDAATYYCQHSRELPLTFGAGTMLELKR

SEQ ID NO 12:

28F26A3/"0073"/"0124":heavy chain-mIgG2a (CDRs marked with bold)

EVKVVESGGGLVKPGGSLKLSCAASGFVFSSYDMSWVRQIPEKRLEWVAAISSGDYYTYYPDS VKGRFTISRDDARNTLYLQMSSLRSEDTALYYCARHRGGNYPQYAMDYWGQGTSVTVSS

SEQ ID NO 13:

28F26A3/"0073"/"0124": light chain-kappa (CDRs marked with bold)

DILLTQSPASFAVSLGQRATISCRASKSVSTSGYNYIHWYQQKPGQPPKLLIYLTSNLESGVPA RFSGSGSGTDFTLNIHPVEEEDAATYYCQHSRELPFTFGSGTKLEIKR

FIG. 1 (CONTINUED)

SEQ ID NO 14:

11H08 heavy chain (0230) – CDRs marked with underline:

EVQLVESGGGLVKPGGSLRLSCAASGFTFT<u>NYAMS</u>WVRQAPGQRLEWVS<u>TITSGGSYIYYLDSV</u>
<u>KG</u>RFTISRDNAKSTLYLQMNSLRAEDTAVYNCAR<u>RKDGNYYYAMDY</u>WGQGTTVTVSSASTKGPS
VFPLAPCSRSTSESTAALGCLVKDYFPEPVTVSWNSGALTSGVHTFPAVLQSSGLYSLSSVVTVP
SSSLGTKTYTCNVDHKPSNTKVDKRVESKYGPPS

SEQ ID NO 15:

11H08 light chain (0230) – CDRs marked with underline:

DIVLTQSPSSLSASVGDRVTITC<u>RASESVDSYGNSFIH</u>WYQQKPGQPPKLLIY<u>RASNLES</u>GIPARFS
GSGSRTDFTLTISSLQPEDFATYYC<u>QQSYEDPWT</u>FGGGTKVEIKRTVAAPSVFIFPPSDEQLKSGT
ASVVCLLNNFYPREAKVQWKVDNALQSGNSQESVTEQDSKDSTYSLSSTLTLSKADYEKHKVYA
CEVTHQGLSSPVTKSFNRGEC

SEQ ID NO 16:

"0228 heavy chain" (humanized version of 27F44A2/"0072"): incl. the "S49A" back mutation – CDRs marked with underline):

EVQLVESGGGLVQPGGSLRLSCAASGFTFS<u>NYDMS</u>WVRQATGKGLEWVAA<u>FSSDGYTEYPGSV</u>
<u>KG</u>RFTISRENAKNSLYLQMNSLRAGDTAVYYCAR<u>HADYANYPVMDY</u>WGQGTLVTVSSASTKGPS
VFPLAPCSRSTSESTAALGCLVKDYFPEPVTVSWNSGALTSGVHTFPAVLQSSGLYSLSSVVTVP
SSSLGTKTYTCNVDHKPSNTKVDKRVESKYGPPC

SEQ ID NO 17:

"0228 light chain" (humanized version of 27F44A2/"0072") – CDRs marked with underline):

DIQMTQSPSSLSASVGDRVTITC<u>RASKSVSTSGYSYMH</u>WYQQKPGKAPKLLIY<u>LASNLES</u>GVPSR
FSGSGSGTDFTLTISSLQPEDFATYYC<u>QHSRELPLT</u>FGGGTKVEIKRTVAAPSVFIFPPSDEQLKSG
TASVVCLLNNFYPREAKVQWKVDNALQSGNSQESVTEQDSKDSTYSLSSTLTLSKADYEKHKVYA
CEVTHQGLSSPVTKSFNRGEC

SEQ ID NO 18:

"0130 heavy chain" (45F36) – CDRs marked with underline

FIG. 1 (CONTINUED)
EVQLVESGGGLVKPGGSLKLSCAASGFTFS<u>SYAMS</u>WVRQSPDKRLEWVA<u>EISSSGDIYIYYPDIV</u>
<u>TG</u>RFTISRDNAKKTLYLEMSGLRSEDTAMYYCAR<u>DREAYYGQQYVMD</u>YWGQGTSVTVSS

SEQ ID NO 19:
"0130 light chain" (45F36) – CDRs marked with underline
DIVLTQSPASLAVSLGLSVTISC<u>RASESIEYSGTSFLQ</u>WYQQKPGQPPRLLIY<u>GSSTVES</u>GVPARFS
GSGSGTDFSLNIHPVEEDDSAMYFC<u>QQSRRLPWT</u>FGGGTKLEIKR SEQ ID NO 20:
"0143" heavy chain (44F434) – CDRs marked with underline
EVQLVESGGDLVMPGGSLKLSCAASGFIFS<u>SYGLS</u>WIRQTPDKRLEWVAT<u>ISGGDSYTYYPDSVK</u>
GRFTISSDNAKNTLYLQMTSLKSEDTAMYYCATQ<u>REIYYGTYYALDH</u>WGQGTSVTVSS SEQ ID NO 21:
"0143" light chain (44F434) – CDRs marked with underline
DIQMTQTTSSLSASLGDRVTISC<u>RASQDINNYLN</u>WYQQKPDGTVKLLIY<u>YTSRLQS</u>GVPSRFSGSG
SGTDYSLTISSLEQDDIATYFC<u>QQGSPLPWT</u>FGGGTKLEIKR SEQ ID NO 22:
"0152" heavy chain (60F191) – CDRs marked with underline
EVQLVESGGGLVEPGGSLKLSCAASGFTFS<u>TYAMS</u>WVRQSPEKRLEWVA<u>EISSGDSYTYYPDIVT</u>
GRFTISRDDAKNTLFLEMSSLRSEDTAIYYCVRD<u>QDYRYDGYYAMDH</u>WGQGTSVTVSS SEQ ID NO 23:
"0152" light chain (60F191) – CDRs marked with underline
DIVLTQSPASLAVSLGQRATISC<u>RASESVEHYGISLMQ</u>WYQQKPGQPPKLLIY<u>AASNVES</u>GVPAR
FSGRGSGPDFSLNIHPVEEDDIAMYFC<u>QQSRRIPWT</u>FGGGTKLEIKR SEQ ID NO 24:
"0148" heavy chain (5F13 – CDRs marked with underline)
EVQLVESGGGLVKPGGSLKFSCAVSGFTFS<u>SYVMS</u>WVRQTPEKRLEWVA<u>AISSDSYTYYLDSV</u>
<u>K</u>GRFTISRDNAKNTLYLQMSSLRSEDTAMYYCARQ<u>TRSDAMDY</u>WGQGTSVTVSS

FIG. 1 (CONTINUED)

SEQ ID NO 25:
"0148" light chain (5F13 – CDRs marked with underline)
DIVLTQSPASLAVSLGQRATISC<u>RASESVDNYGNSFMH</u>WYQQKPGQPPKLLIY<u>RASNLES</u>GIPARF
SGSGSRTDFTLTINPVEADDVAIYYC<u>QQSNEDPLT</u>FGAGTKLELKR SEQ ID NO 26:
"0163" heavy chain (45F187 - CDRs marked with underline)
EVQLVESGGGLVQPGGSLRLSCATSGFTFT<u>NYYMA</u>WVRKPPGKTLEWLG<u>FMRNIVNGYTTDYSG
SVEG</u>RFTISRDNSQSILYLQMNALRPEDSATYYCAR<u>DIGYRYDGGGYGLDY</u>WGQGTSVTVSS SEQ ID NO 27:
"0163" light chain (45F187 - CDRs marked with underline)
DIQMTQSPASLSASVGETVTLTC<u>RASGNIHNYLT</u>WYQQKQGKSPQLLVY<u>NVKTLAD</u>GVSSRFSGS
GSGTQFSLKINSLQPEDFGSYYC<u>QHFWTTPYT</u>FGGGTKLEIRR SEQ ID NO 28:
The basic humanization construct of 0072, hz0072 (VH) – CDRs marked with bold
EVQLVESGGGLVQPGGSLRLSCAASGFTFSNYDMSWVRQATGKGLEWVS**AFSSDGYTFYPGSV
KGRFTISRENAKNSLYLQMNSLRAGDTAVYYCARHADYANYPVMDY**WGQGTLVTVSS

SEQ ID NO 29:
The basic humanization construct of 0072, hz0072 (VL) - CDRs marked with bold
DIQMTQSPSSLSASVGDRVTITCRASKSVSTSGYSYMHWYQQKPGKAPKLLIYLASNLES
GVPSRFSGSGSGTDFTLTISSLQPEDFATYYCQHSRELPLTFGGGTKVEIK

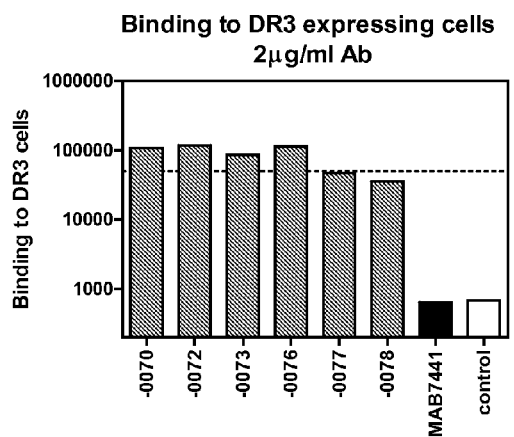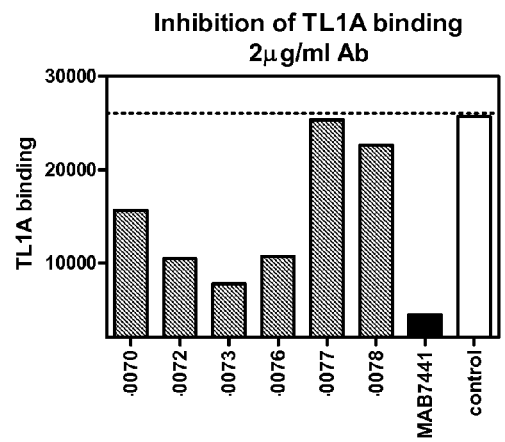
FIG. 6A                    FIG. 6B

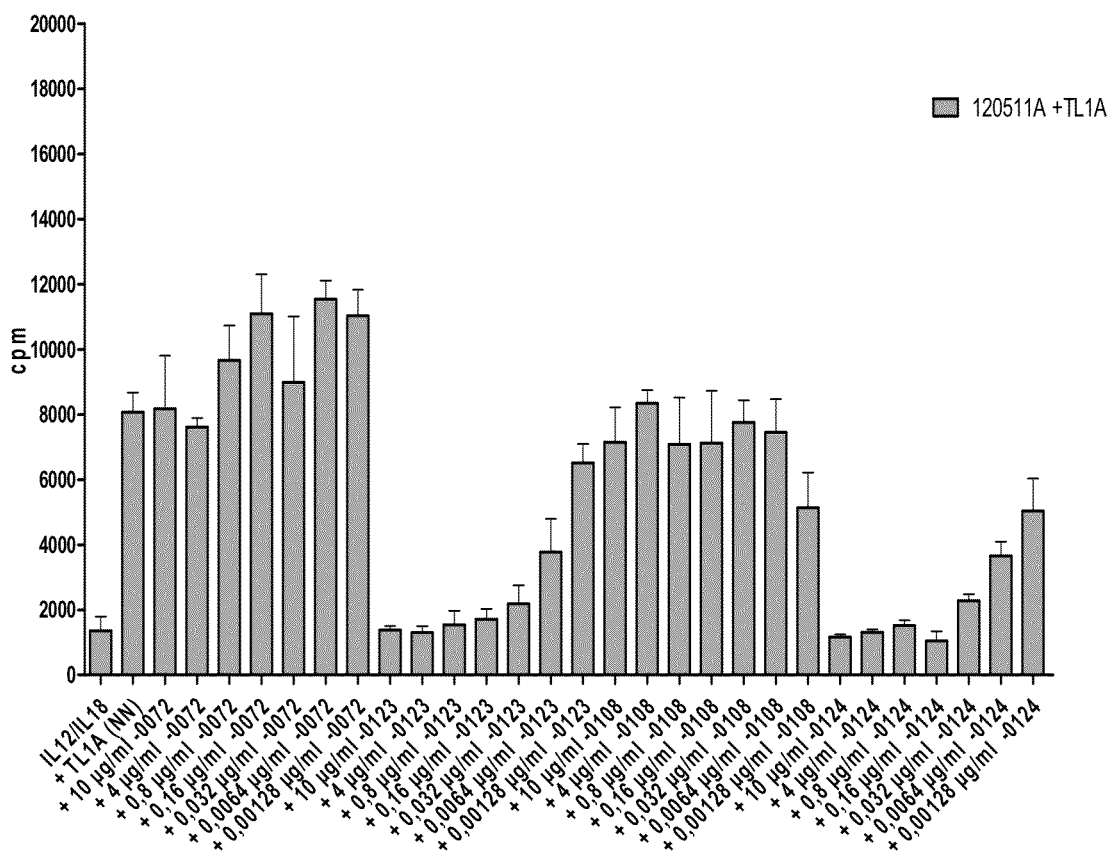

ANTAGONISTIC DR3 LIGANDS

CROSS-REFERENCE TO RELATED APPLICATIONS

This application is a continuation of U.S. patent application Ser. No. 13/982,617, filed Jul. 30, 2013, which is a 35 U.S.C. §371 national stage application of International Patent Application PCT/EP2012/053539 (published as WO 2012/117067), filed Mar. 1, 2012, which claimed priority of European Patent Application 11156416.7, filed Mar. 1, 2011; this application further claims priority under 35 U.S.C. §119 of U.S. Provisional Application 61/448,827, filed Mar. 3, 2011, the entire contents and substance of which are hereby incorporated by reference in their entireties as if fully set forth below.

BACKGROUND OF THE INVENTION

TL1A is a TNF-superfamily member produced by endothelial cells, dendritic cells, monocytes and other immune cells. TL1A signals through DR3-a TNF receptor-superfamily member expressed by activated T-cells and other immune cells. Receptor ligation by TL1A leads to increased proliferation and cytokine production by T-helper effector cells. DR3 and TL1A are involved in RA and CD and antagonizing the DR3-induced effects would therefore be desirable in treatment of inflammatory diseases such as e.g. RA (Rheumatoid Arthritis) and CD (Crohns Disease).

WO2011106707 discloses a DR3 specific antibody (11H08), as well as variants thereof, comprising the 11H08 CDR sequences (SEQ ID NO 14+15) inserted into various antibody frameworks. The 11H08 antibody binds DR3 with a relatively low affinity and it does not bind to the CRD1 domain. There is thus a need in the art for DR3 antagonists useful for treating inflammatory diseases.

BRIEF SUMMARY OF THE INVENTION

Bivalent antibodies raised against DR3 have agonistic effects. A few of these agonistic DR3 specific antibodies have the ability to block interaction between DR3 and TL1A. As agonistic antibodies lead to increased proliferation and cytokine production by T helper effector cells, it is undesirable to use bivalent DR3 antibodies in connection with treatment of inflammatory disorders.

The present invention provides antagonistic DR3 ligands, wherein said ligands have a monovalent specificity for DR3, and wherein said ligand blocks binding of TL1A to DR3. Such ligands are preferably derived from a bivalent agonistic antibody and they are optionally conjugated with a half life extending moiety such as e.g. a lipophilic moiety. Such ligands preferably have a high affinity, and/or preferably bind to the CRD1 domain of DR3. The present invention furthermore relates to use of such ligands for treating inflammatory diseases. The DR3 ligands of the present invention are shown herein to be capable of antagonizing effects induced via DR3.

BRIEF DESCRIPTION OF THE DRAWINGS

FIG. 1: The sequences referred to herein.

FIG. 6: Examples of antibodies blocking the TL1A:DR3 interaction done by flow cytometry. FIG. 6A show specific binding to DR3 cells of 6 positive DR3 antibodies. FIG. 6B show inhibition studies showing 4 blocking antibodies and two non-blockers. Y-axis shows mean intensity fluorescence.

FIG. 8: CD4+ T cells stimulated with IL12/IL18+ TL1A with and without anti-DR3Fabs vs mAb. T cell proliferation is measured on day 5.

DETAILED DESCRIPTION OF THE INVENTION

Figure 2:
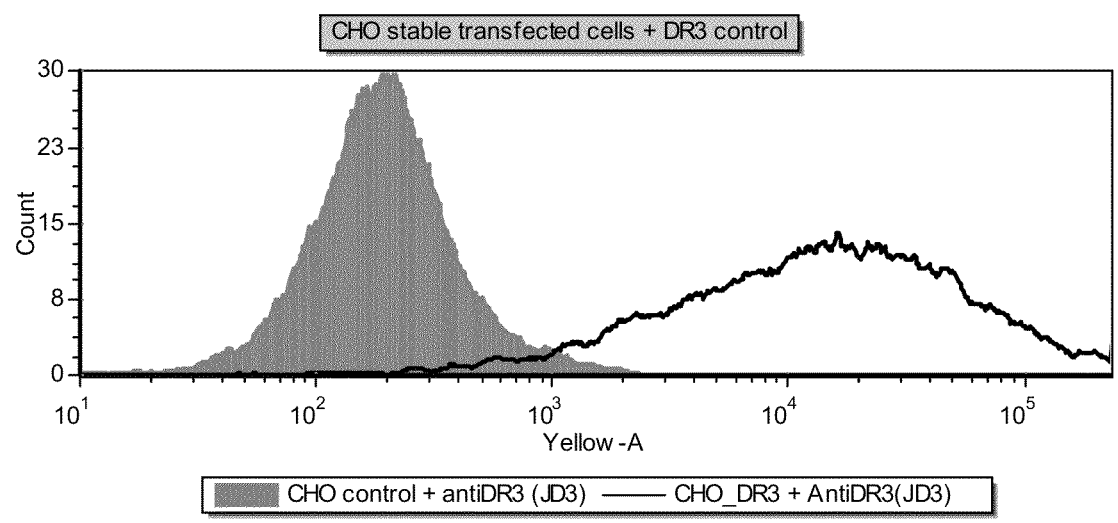
FIG. 2: DR3 expression on CHOK1SV analysed by FCM. JD3 is a commercially available DR3 antibody.

The inventors of the present invention realized that production of the DR3 antigen-soluble as well as cell-surface expressed versions thereof—proved difficult as none of the traditional approaches were successful. Recombinant expression of the extracellular domain of DR3 in human cell lines usually led to the secretion of soluble proteins that contained large amounts of oligomers and high molecular weight complexes (see also example 3). These oligomerized protein batches were presumably not optimal for immunizations. In parallel with soluble protein expression optimization (as described in example 3), mice were immunized with cells over-expressing membrane-bound DR3. Production of a stable cell line over-expressing DR3 was, however, not straight-forward. The death domain in full length DR3 leads to cell-death in stably transfected cell lines over-expressing DR3 and it was therefore necessary to modify the full length DR3 (see examples 2 and 5). Immunizations have been performed in different mice strains (BALB/C, RBF and NMRCF1) in order to increase the antibody-repertoire diversity and the likelihood of generating neutralizing anti-DR3Abs.

Several hundred DR3-binding antibodies were identified; of these only few (~2%) were able to block/inhibit DR3:TL1A binding. The DR3 antibodies with the ability to block DR3:TL1A binding were thus presumed to have the ability to antagonize DR3 induced effects. It did, however, turn out that all DR3 antibodies regardless of whether they had the ability to block DR3:TL1A binding or not were agonistic both in the presence and absence of TL1A, i.e. they did apparently to some extent mimic the effects on DR3 that TL1A binding induces.

Based on these surprising observations, the inventors hypothesized that the explanation for the agonistic effects exerted by all the DR3 antibodies could possibly be that any bivalent DR3 antibody would result in clustering of DR3 and that DR3 clustering might have the potential to elicit intracellular DR3 signaling. This hypothesis furthermore finds support in recent publications regarding TNFR family members Fas (CD95) and TNFR2 (Wang et al. (2010) Nature Struc. Mol. Biol. 17, 1324-1328; Mukai et al. (2010) Sci. Signal. 3, ra83). Wang et al provide both structural data and solution data demonstrating that the intracellular signaling complex are of higher order and contains at least 5-7 copies of the receptor. Similarly, Mukai et al demonstrate that clustering of the extracellular part of the receptor is induced by ligand binding. Thus, both publications indicate that higher order clustering of these TNFR family members may be a prerequisite for signaling.

In order to test this hypothesis, Fab fragments (monovalent DR3 antibodies) produced by cleavage of mAb's by papain were tested in functional assays. The surprising outcome from these assays was that monovalent DR3 antibodies (made on basis of the DR3 antibodies having the ability to block/inhibit DR3:TL1A binding) were antagonistic in functional assays, i.e. they had the ability to inhibit DR3 induced effects. Monovalent DR3 ligands/antibodies do therefore not facilitate DR3-clustering and they do therefore not have agonistic effects.

Antibodies that did not prevent TL1A:DR3 interaction were used as negative controls. This type of antibodies are agonistic in the absence of TL1A at very high concentrations but only as mAbs. The corresponding Fabs from these antibodies were not able to prevent TL1A-induced effects.

Definitions

"Inflammation" is the complex biological response of vascular tissues to harmful stimuli, such as pathogens, damaged cells, or irritants. Inflammation is a protective attempt by the organism to remove the injurious stimuli as well as initiate the healing process for the tissue. Inflammation is not a synonym for infection—infection is caused by an exogenous pathogen, while inflammation is the responses of the immune system in the organism to the pathogen.

Normally, the immune system is able to distinguish between the body's normal cells or "self" and foreign pathogens or abnormal cells or "non-self". The process by which the immune system loses the ability to recognize "self" as normal and the subsequent response directed against the tissue or cells, results in loss of tolerance, a state of "autoimmunity". The pathologies resulting from autoimmunity often have serious clinical consequences and are one of the major health problems in the world, especially in developed nations.

Biologic therapeutics are now available for the treatment of certain autoimmune diseases and/or cancer. For example, patients with rheumatoid arthritis may be treated with Rituximab (anti-CD20), and patients with Crohn's disease may be treated with Infliximab or Natalizumab. Unfortunately, patients that receive treatment with any one of these biologics also experience a variety of side-effects and/or are non-responders and/or develop inhibitors. There is still a need for alternative biological medicaments which specifically target pathological tissue and/or which do not affect healthy tissue and/or which result in less severe side effects and/or which result in fewer side effects and/or which may be used long-term and/or which do not result in the formation of inhibitors. The current invention relates to these unmet needs amongst patients with autoimmune diseases and in those with chronic inflammatory diseases.

The ligands of the present invention are thus suitable for use in treatment of inflammatory diseases and conditions such as e.g. psoriasis, type I diabetes, Grave's disease, Inflammatory bowel disease (IBD), Crohn's disease, ulcerative colitis, irritable bowel syndrome, multiple sclerosis, rheumatoid arthritis (RA), autoimmune myocarditis, Kawasaki disease, coronary artery disease, chronic obstructive pulmonary disease, interstitial lung disease, autoimmune thyroiditis, systemic lupus erythematosus (SLE), scleroderma, systemic sclerosis, psoriatic arthritis, osteoarthritis, atoptic dermatitis, vitiligo, graft vs. host disease, Sjöogrens's syndrome, autoimmune nephritis, Goodpasture's syndrome, chronic inflammatory demyeliniating polyneutopathy, allergy, asthma and other autoimmune diseases.

"Crohn's disease" (CD/granulomatous/colitis) is an inflammatory disease of the intestines that may affect any part of the gastrointestinal tract from mouth to anus, causing a wide variety of symptoms. It primarily causes abdominal pain, diarrhea (which may be bloody), vomiting, or weight loss, but may also cause complications outside of the gastrointestinal tract such as skin rashes, arthritis, inflammation of the eye, tiredness, and lack of concentration. There is no known pharmaceutical or surgical cure for Crohn's disease. Treatment options are restricted to controlling symptoms, maintaining remission and preventing relapse.

"Rheumatoid arthritis" (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds.

"DR3" is sometimes referred to as Death Receptor 3, TRAMP, TNFRSF12, TNFR25, TNFRS25, APO-3, DDR3, LARD, TR3, WSL-1, or WSL-LR. Human DR3 is a member of the TNF receptor (TNFR) super family comprising four cysteine-rich motives in the extracellular domain and a "death domain" in the cytoplasmic domain. Human DR3 comprises the amino acid sequence as defined in SEQ ID NO:1. The extracellular domain of DR3 (residues 25-199) comprises four cysteine-rich domains (CRD1, CRD2, CRD3 and CRD4). Each CRD typically contains six cysteine residues that form three disulfide bounds. In addition each CRD can be subdivided into modules A1 and B2 which are typically observed in conventional members of the TNFR superfamily.

"Block/inhibit/reduce binding of DR3 to TL1A". Monovalent ligands/antibodies according to the present invention have the ability to inhibit/block/reduce DR3:TL1A binding. It can be tested in a high-throughput image based assay. This was done in an FMAT system, by screening for the ability to bind DR3 transfected CHO cells and counter-screened against wild-type cells (described more in detail in example 4). Monovalent ligands/antibodies according to the present invention have the capacity to block or inhibit or reduce DR3:TL1A binding, as measured in this assay, if DR3:TL1A binding is reduced at least 10%, preferably at least 20%, preferably at least 25% preferably at least 30%, preferably at least 40%, preferably at least 50%, preferably at least 60%, preferably at least 70%, preferably at least 75%, preferably at least 80%, preferably at least 90%, preferably at least 95% and most preferably about 100%.

"Protractive groups"/"half life extending moieties" is herein understood as one or more chemical groups attached to one or more amino acid site chain functionalities such as —SH, —OH, —COOH, —CONH$_2$, —NH$_2$, or one or more N- and/or O-glycan structures and that can increase in vivo circulatory half life of a number of therapeutic proteins/peptides when conjugated to these proteins/peptides. Examples of protractive groups/half life extending moieties include but not limited to are: Biocompatible fatty acids and derivatives thereof, Hydroxy Alkyl Starch (HAS) e.g. Hydroxy Ethyl Starch (HES), Poly Ethylen Glycol (PEG), Poly(Gly$_x$-Ser$_y$)$_n$ (HAP), Hyaluronic acid (HA), Heparosan polymers (HEP), Phosphorylcholine-based polymers (PC polymer), Fleximers, Dextran, Poly-sialic acids (PSA), an Fc domain, Transferrin, Albumin, Elastin like peptides, XTEN polymers, Albumin binding peptides, a CTP peptide, and any combination thereof.

"PEGylated DR3 ligand variants" according to the present invention may have one or more PEG molecule attached to any part of the DR3 ligand polypeptide including any amino acid residue or carbohydrate moiety of the DR3 ligand polypeptide. Chemical and/or enzymatic methods can be employed for conjugating PEG or other protractive groups to a glycan on the monovalent DR3 ligand according to the invention. An example of an enzymatic conjugation process is described e.g. in WO03031464. The glycan may be naturally occurring or it may be inserted via e.g. insertion of an N-linked glycosylation site using methods well known in the art. "Cysteine-PEGylated DR3 ligand variant" according to the present invention have one or more PEG molecules conjugated to a sulfhydryl group of a cysteine present in the DR3 ligand. "Cysteine-acylated DR3 ligand variant" or "Cysteine-alkylated DR3 ligand variant" according to the present invention have one or more hydrophobic half life extending moieties conjugated to a sulfhydryl group of a cysteine introduced in the DR3 ligand. It is furthermore possible to link protractive half life extending moieties to other amino acid residues.

The most abundant protein component in circulating blood of mammalian species is serum albumin, which is normally present at a concentration of approximately 3 to 4.5 grams per 100 milliters of whole blood. Serum albumin is a blood protein of approximately 65,000 daltons which has several important functions in the circulatory system. It functions as a transporter of a variety of organic molecules found in the blood, as the main transporter of various metabolites such as fatty acids and bilirubin through the blood, and, owing to its abundance, as an osmotic regulator of the circulating blood. Serum albumin has a half-life of more than one week, and one approach to increasing the plasma half-life of proteins has been to conjugate to the protein a moiety that binds to serum albumin. Albumin binding property may be determined as described in *J. Med. Chem.*, 43, 1986, (2000) which is incorporated herein by reference.

Hydrophobic/Lipophilic Half Life Extending Moiety: The ligands according to the present invention are preferably conjugated with a half life extending moiety that is largely lipophilic/hydrophobic in nature. In a preferred embodiment, the hydrophobic half life extending moiety is capable of forming non-covalent complexes with albumin ("albumin binder"), thereby promoting the circulation of the derivative with the blood stream, and also having the effect of extending the time of action of the derivative. Thus, a preferred substituent, or moiety, as a whole may be referred to as an albumin binding moiety.

The half life extending moiety is preferably at, or near, the opposite end of the albumin binding moiety as compared to its point of attachment to the DR3 ligand according to the invention. The other portion of the albumin binding moiety, i.e. the portion in-between the half life extending moiety and the point of attachment to the peptide, may be referred to as a linker moiety, linker, spacer, or the like. However, the presence of a linker is optional, and hence the albumin binding moiety may be identical to the half life extending moiety.

In particular embodiments, the albumin binding moiety and/or the half life extending moiety is lipophilic, and/or negatively charged at physiological pH (7.4).

The albumin binding moiety and/or the half life extending moiety may be covalently attached to an amino group of the peptide by conjugation chemistry such as by alkylation, acylation, or amide formation; or to a hydroxyl group, such as by esterification, alkylation; or to other groups through oximation.

In a preferred embodiment, an active thiophilic derivative of the albumin binding moiety and/or the half life extending moiety is covalently linked to the thiol of a cysteine residue of the anti-DR3 Fab. Such thiophilic groups include, but are not limited to, maleimides, halo-maleimides, halides (especially α-haloacetyl), acryloyl-derivatives (eg. acrylates and acrylamides), vinylsulfones, reactive disulfide groups (eg. 2-pyridyl). Thus, the anti-DR3 Fab' of the present invention is preferably linked to the albumin binding moiety through a thioether or disulfide bond.

Monovalent antibodies according to the present invention, such as e.g. Fab' fragments, may be designed to contain the naturally occurring cysteine residue from the heavy chain that forms part of one of the heavy chain sulphur bridges of an intact antibody. This cysteine residue is termed C239 (Kabat numbering). Cysteine residues can also be inserted by genetic engineering but there may be safety advantages associated by employing naturally occurring cysteine residues for conjugation purposes.

In a preferred embodiment, an active ester of the albumin binding moiety and/or the hydrophobic half life extending moiety is covalently linked to an amino group of a sialic acid residue or a sialic acid derivative, under formation of an amide bond (this process being referred to as acylation).

According to a highly preferred embodiment of the present invention, the albumin bidning moiety is attached to the ligand via a glycan using enzymatic methods such as e.g. a method involving use of a sialilyltransferase.

For the present purposes, the terms "albumin binding moiety", "half life extending moiety", and "linker" include the un-reacted as well as the reacted forms of these molecules. Whether or not one or the other form is meant is clear from the context in which the term is used.

The term "fatty acid" refers to aliphatic monocarboxylic acids having from 4 to 28 carbon atoms, it is preferably unbranched, and/or even numbered, and it may be saturated or unsaturated The term "fatty diacid" refers to fatty acids as defined above but with an additional carboxylic acid group in the omega position. Thus, fatty diacids are dicarboxylic acids.

The nomenclature is as is usual in the art, for example —COOH, as well as HOOC—, refers to carboxy; —C$_6$H$_4$— to phenylen; —CO—, as well as —OC—, to carbonyl (O═C<); C$_6$H$_5$—O— to phenoxy; and halide refers to the halogens —F, —Cl, —Br, —I, and -At.

In a preferred embodiment, the albumin binding moiety of the present invention comprises a fatty acyl group (—(CH$_2$)$_n$—CO—, where n=1, 2, 3, . . . 40) or an omega-carboxy fatty acyl group (HO$_2$C—(CH$_2$)$_n$—CO—, where n=1, 2, 3, . . . 40) linked to the peptide or protein via a linker and a sialic acid residue or sialic acid derivative.

In a preferred embodiment, the albumin binding moiety of the present invention comprises a fatty acyl group (—(CH$_2$)n-CO—, where n=1, 2, 3, . . . 40) or an omega-carboxy fatty acyl group (HO2C—(CH2)n-CO—, where n=1, 2, 3, . . . 40) linked to the peptide or protein via a linker and a cysteine residue. In a particular preferred embodiment, n is 16 or 18.

In another preferred embodiment, the albumin binding moiety of the present invention comprises a fatty acyl group of the type R—(CH$_2$)n-CO—, where n=1, 2, 3, ... 40, linked to the peptide or protein via a linker and a cysteine residue. R is a group comprising an acidic group, eg. tetrazol-5-yl or O—C6H4-COOH. In a particular preferred embodiment, n is 14 or 15.

Compounds having a —(CH$_2$)$_{12}$— moiety are possible albumin binders in the context of this invention. If such a compound is attached to a protein or peptide and results in an increased plasma half life of said protein or peptide, it is understood that the albumin binder may contribute to the overall increase of plasma half life.

In a preferred embodiment the linker moiety, if present, has from 2 to 80 C-atoms, preferably from 5 to 70 C-atoms. In additional preferred embodiments, the linker moiety, if present, has from 4 to 20 hetero atoms, preferably from 2 to 40 hetero atoms, more preferably from 3 to 30 hetero atoms. Particularly preferred examples of hetero atoms are N-, and O-atoms. H-atoms are not hetero atoms.

In another embodiment, the linker comprises at least one OEG molecule, and/or at least one glutamic acid residue, or rather the corresponding radicals (OEG designates 8-amino-3,6-dioxaoctanic acid, i.e. this radical: —NH—(CH2)2-O—(CH2)2-O—CH2-CO—).

In one preferred embodiment, the linker moiety comprises a di-carboxamide moiety and the linker is linked to a cysteine residue through a thioether bond. In preferred examples, the di-carboxamide moiety contains from 2-30 C-atoms, preferably 4-20 C-atoms, more preferably 4-10 C-atoms.

In one preferred embodiment, the linker moiety comprises a di-carboxamide moiety linked to a sialic acid residue by an amide bond. In preferred examples, the di-carboxyl residue has from 2-30 C-atoms, preferably 4-20 C-atoms, more preferably 4-10 C-atoms. In additional preferred examples, the di-carboxyl residue has from 0-10 hetero-atoms, preferably 0-5 hetero-atoms.

In another preferred example, the linker moiety/spacer comprises a group containing both an amino and a distal carboxyl-group linked to a sialic acid residue by an amide bond through its distal carboxyl groups. In one preferred embodiment this group is an OEG group. The term "hydrophilic spacer" as used herein means a spacer that separates a monovalent DR3 antibody/ligand according to the invention and an albumin binding residue with a chemical moiety which comprises at least 5 non-hydrogen atoms where 30-50% of these are either N or O. Preferably, the albumin binding residue is, via a hydrophilic spacer, linked to a Cys residue.

The amino acid glutamic acid (Glu) comprises two carboxylic acid groups. Its gamma-carboxy group is preferably used for forming an amide bond with an amino group of a sialic acid residue or a sialic acid derivative, or with an amino group of an OEG molecule, if present, or with the amino group of another Glu residue, if present. The amino group of Glu in turn forms an amide bond with the carboxy group of the half life extending moiety, or with the carboxy group of an OEG molecule, if present, or with the gamma-carboxy group of another Glu, if present. This way of inclusion of Glu is occasionally briefly referred to as "gamma-Glu".

"Fc fusion derivatives" or "Fc fusion proteins" or DR3 antibody having a mutated Fc domain is herein meant to encompass a DR3 ligand according to the invention fused to an Fc domain that can be derived from any antibody isotype, although an IgG Fc domain will often be preferred due to the relatively long circulatory half life of IgG antibodies—IgG1 and IgG4 isotypes are preferred. The Fc domain may furthermore be modified in order to modulate certain effector functions such as e.g. complement binding and/or binding to certain Fc receptors. The Fc domain may furthermore be modulated in order to increase affinity to the neonatal Fc receptor. Fusion of a DR3 ligand according to the invention with an Fc domain, having the capacity to bind to FcRn receptors, will generally result in a prolonged circulatory half life of the fusion protein. Mutations in positions 234, 235 and 237 in an IgG1 Fc domain will generally result in reduced binding to the FcγRI receptor and possibly also the FcγRIIa and the FcγRIII receptors. These mutations do not alter binding to the FcRn receptor, which promotes a long circulatory half life by an endocytic recycling pathway. Preferably, a modified IgG1 Fc domain of a fusion protein according to the invention comprises one or more of the following mutations that will result in decreased affinity to certain Fc receptors (L234A, L235E, and G237A) and in reduced C1q-mediated complement fixation (A330S and P331S), respectively. Alternatively, the Fc domain may be an IgG4 Fc domain optionally comprising the S241P/S228P mutation.

The term "antibody", "monoclonal antibody" and "mAb" as used herein, is intended to refer to immunoglobulin molecules and fragments thereof that have the ability to specifically bind to an antigen. Full-length antibodies comprise four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Antibodies can be in the form of different isotypes; e.g. IgG (e.g. IgG1, IgG2, IgG3, IgG4), IgGA1, IgA2, IgD, and IgE. A full-length antibody is normally bi-valent/di-valent, i.e. it has the capacity to bind to the antigen with both "arms". In contrast, a monovalent antibody according to the present invention comprises only one binding site specific for the antigen/DR3.

The "Fab region"/"Fab domain"/"Fab fragment"/"Fab", contains variable sections that define the specific target that the antibody can bind. A Fab fragment is an example of a mono-specific/monovalent DR3 ligand/DR3 antibody according to the present invention.

Examples of monovalent DR3 ligands/antibodies according to the present invention include: Fab fragments, monovalent fragments consisting of the VL, VH, CL and CH I domains; a bivalent fragment comprising two Fab fragments linked e.g. by a disulfide bridge at the hinge region, where only one of these Fab fragments is specific for DR3; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR); and (v) a bi-specific antibody that is monovalent for DR3. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426: and Huston et al. (1988) Proc. Natl. Acad. Sci. USA 85:5879-5883). Other forms of single chain antibodies, such as diabodies are also encompassed within the term "monovalent DR3 ligands/antibodies".

"Diabodies" are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

The terms "human antibody", as used herein, means monovalent DR3 antibodies according to the invention having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular in the CDR3.

However, the term "human antibody", as used herein, is not intended to include antibodies in which CDR sequences derived from the germline of another mammalian species, such as a mouse, have been grafted onto human framework sequences, e.g. the so-called "humanized antibodies" or human/mouse chimeric antibodies. Humanized monovalent DR3 antibodies are also a part of the present invention.

The term "chimeric monovalent antibody" refers to monovalent DR3 antibodies according to the invention whose light and heavy chain genes have been constructed, typically by genetic engineering, from immunoglobulin variable and constant region genes belonging to different species. For example, the variable segments of genes from a mouse monoclonal antibody may be joined to human constant segments.

The term "epitope" as used herein means any antigenic determinant on an antigen to which the monovalent antibody binds. Epitopic determinants usually consist of chemically active surface groupings of molecules such as amino acids or sugar mloieties and often have specific three dimensional structural characteristics, as well as specific charge characteristics. Examples of methods for characterizing epitopes include HX-MS, NMR, X-ray, peptide walking, assays, etc. The term "paratope" refers to the part of the antibody that recognizes the antigen.

Monovalent DR3 antibodies of the present invention may be described or specified in terms of the epitope(s) or portion(s) of DR3 that they recognize or specifically bind. The epitope(s) or the polypeptide portions(s) may be specified as e.g. by N-terminal and C-terminal positions, or by size in contiguous amino acid residues. Monovalent DR3 antibodies of the present invention may also be described or specified in terms of their cross-reactivity. Antibodies that do not bind any other analog, ortholog, or homolog of a polypeptide are included.

"Epitope binning"/"competition binding assay" refers to the use of competitive binding assays to identify pairs of ligands/antibodies that are, or are not, capable of binding DR3 simultaneously, thereby identifying ligands/antibodies according to the invention that bind to the same, or overlapping epitopes on the DR3 protein (se example 10), or that cannot bind simultaneously due to steric hindrance. Binning experiments provide evidence that antigenically distinct epitopes are present. However, by themselves, they do not identify, or "map" the epitope to a specific amino acid sequence or location on the DR3 protein. Competition for binding can be evaluated for any pair of ligands/antibodies or fragments. Frequently, favourable properties of a family (or bin) of ligands/antibodies can be correlated with a binding to a specific epitope defined by the antibody bin/competitive group.

The terms "immunoreacts" or "immunoreacting", as used herein, means any binding of a ligand/antibody to its epitope with a dissociation constant Kd lower than $10^{-4}$ M. The terms "immunoreacts" or "immunoreacting" are used where appropriate inter-changeably with the term "specifically bind".

The term "affinity", as used herein, means the strength of the binding of a ligand/antibody according to the invention to an epitope. The affinity of an antibody/ligand is measured by the dissociation constant Kd, defined as $[Ab] \times [Ag]/[Ab-Ag]$ where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining antibody specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589-601 (1983).

"Decreases IFN-gamma (IFN-γ) release in synovial fluid cells from RA patients" can be measured as described herein. It is understood that at a concentration of about 0.1, 0.5, 1, or 5 pg monovalent antibody/ml, using the assay conditions as described herein, IFN-γ release in synovial fluid T cells from RA patients is decreased by at least 15%, more preferably by at least 20%, more preferably by at least 25%, more preferably by at least 30%, more preferably by at least 35%, more preferably by at least 40%, more preferably by at least 45%, more preferably by at least 50%, and most preferably by at least 60%, more preferably by at least 70%, more preferably by at least 75%, more preferably by at least 80%, and most preferably by at least 95%. In responding patient material, antibodies according to the invention decreases interferon release (e.g. IFN-gamma) in RA as well as CD patient material.

"Decreases release of one or more cytokines in Lamina Propria Mononuclear Cells (LPMCs) from intestinal biopsies from CD patients" can be measured as described herein. It is understood that at a concentration of about 0.1, 0.5, 1, or 5 µg monovalent antibody/ml, using the assay conditions as described herein, cytokine release in LPMCs from CD patients is decreased by at least 15%, more preferably by at least 20%, more preferably by at least 25%, more preferably by at least 30%, more preferably by at least 35%, more preferably by at least 40%, more preferably by at least 45%, more preferably by at least 50%, and most preferably by at least 60%, more preferably by at least 70%, more preferably by at least 75%, more preferably by at least 80%, and most preferably by at least 95%. In responding patient material, antibodies according to the invention decreases interferon release (e.g. IFN-gamma) in RA as well as CD patient material.

"Decreases release of one or more cytokines in $CD4^+$ T cells" can be measured as described herein. It is understood that at a concentration of about 0.1, 0.16, 0.5, 1, or 5 µg monovalent antibody/ml, using the assay conditions as described herein, cytokine release in $CD4^+$ T cells is decreased by at least 15%, more preferably by at least 20%, more preferably by at least 25%, more preferably by at least 30%, more preferably by at least 35%, more preferably by at least 40%, more preferably by at least 45%, more preferably by at least 50%, and most preferably by at least 60%, more preferably by at least 70%, more preferably by at least 75%, more preferably by at least 80%, and most preferably by at least 95%.

"Pharmaceutical compositions" comprising DR3 ligands according to the invention may be supplied as a kit comprising a container that comprises the ligand according to the invention. Therapeutic polypeptides can be provided in the form of an injectable solution for single or multiple doses, or as a sterile powder that will be reconstituted before injection. Pharmaceutical compositions comprising ligands according to the invention are suitable for subcutaneous and/or IV administration. Pharmaceutical compositions according to the present invention may comprise one or more pharmaceutically acceptable carriers.

The term "treatment", as used herein, refers to the medical therapy of any human or other animal subject in need thereof. Said subject is expected to have undergone physical examination by a medical or veterinary medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

In terms of the present invention, prophylactic, palliative, symptomatic and/or curative treatments may represent separate aspects of the invention.

The ligands according to the present invention may be administered along with other drugs (e.g. methotrexate, dexamethasone, and prednisone) and/or other biological drugs.

The monovalent DR3 antibody/ligand may be produced by means of recombinant techniques. The DNA sequences encoding the monovalent DR3 antibody/ligand according to the invention are usually inserted into a recombinant vector. The vector is preferably an expression vector in which the DNA sequence is operably linked to additional segments required for transcription of the DNA as well as a promoter capable of directing the transcription of a cloned gene or cDNA in the desired host cell.

After the cells have taken up the DNA, they are grown in an appropriate growth medium, typically 1-2 days, to begin expressing the gene of interest. The host cell into which the DNA sequences encoding the monovalent DR3 antibody/ligand is introduced may be any cell, and includes yeast, fungi, bacteria and higher eucaryotic cells. Examples of mammalian cell lines for use in the present invention are COS-1, baby hamster kidney (BHK) and 293. A preferred BHK cell line is the tk-ts13 BHK cell line that may be referred to as BHK 570 cells. In addition, a number of other cell lines may be used within the present invention, including Rat Hep I, Rat Hep II, TCMK, NCTC 1469, CHO, and DUKX cells.

The transformed or transfected host cell described above is then cultured in a suitable nutrient medium under conditions permitting expression of the monovalent DR3 antibody/ligand after which all or part of the resulting peptide may be recovered from the culture. The monovalent DR3 antibody/ligand produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

Transgenic animal technology may be employed to produce the monovalent DR3 antibody/ligand of the invention. It is preferred to produce the proteins within the mammary glands of a host female mammal, preferably sheep, goats or cattle. Production in transgenic plants may also be employed. Expression may be directed to a particular organ, such as a tuber.

The monovalent DR3 antibody may also be obtained on basis of a bivalent antibody produced as described above and subsequently subject to peptidase digestion and isolation of the resulting Fab fragments.

Monovalent DR3 antibodies/ligands may subsequently be posttranslationally modified in order to obtain a protein having an extended in vivo circulatory half life.

List Of Embodiments

The following is a list of embodiments according to the invention. This list of embodiments is not intended to be limiting and it is understood that the present invention encompasses any combination of the following embodiments.

Embodiment 1: A monovalent antagonistic DR3 antibody, wherein said monovalent antibody blocks binding of DR3 to TL1A, and wherein said monovalent antibody in a bivalent form thereof is an agonistic antibody that blocks binding of DR3 to TL1A.

Embodiment 2: A monovalent antibody according to embodiment 1, wherein the monovalent antibody is not an antibody having the CDR sequences of the 11H08 antibody set forth in WO2011106707 (SEQ ID NOs 14-15).

Embodiment 3: A monovalent antibody according to any one of embodiments 1-2, wherein said monovalent antibody is conjugated with a lipophilic moiety.

Embodiment 4: A monovalent antibody according to embodiment 3, wherein said lipophilic moiety comprises a —(CH$_2$)$_n$—CO— fatty acyl group, wherein n is 16-18.

Embodiment 5: A monovalent antibody according to embodiment 3, wherein said lipophilic moiety comprises a —(CH$_2$)$_n$—CO— fatty acyl group, wherein n is 15.

Embodiment 6: A monovalent antibody according to any one of embodiments 3-5, wherein said antibody is conjugated to a lipophilic moiety selected from the group consisting of formulas (I), (II), (III), (IV), (V), and (VI):

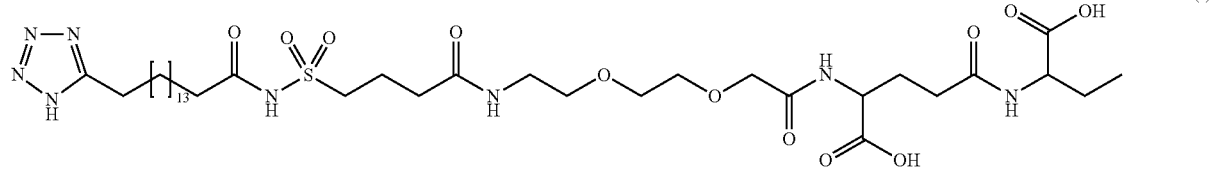

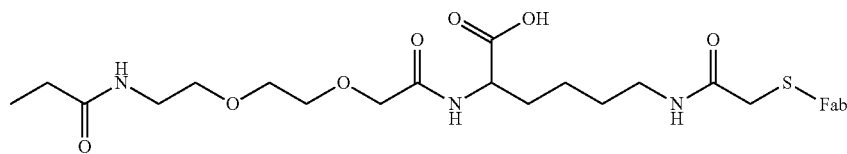
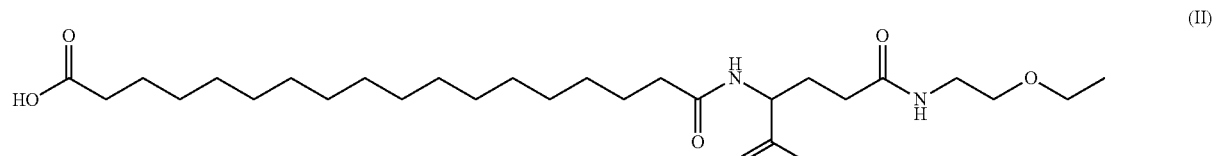
(II)
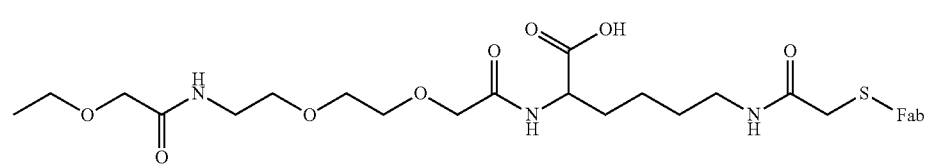
(III)
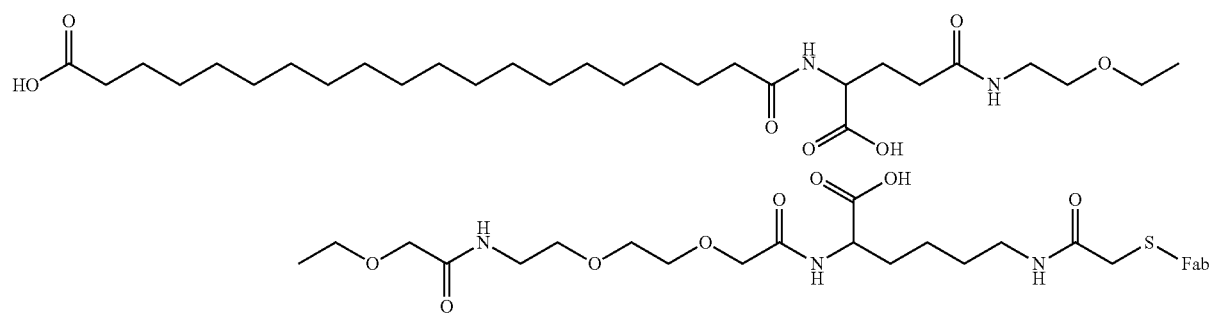
(IV)
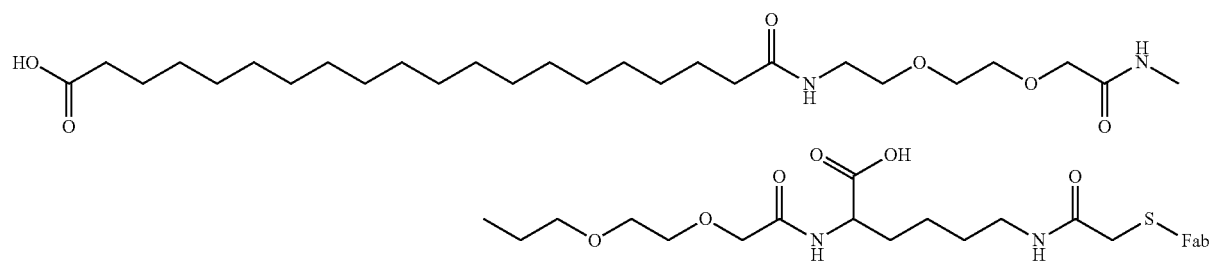
(V)
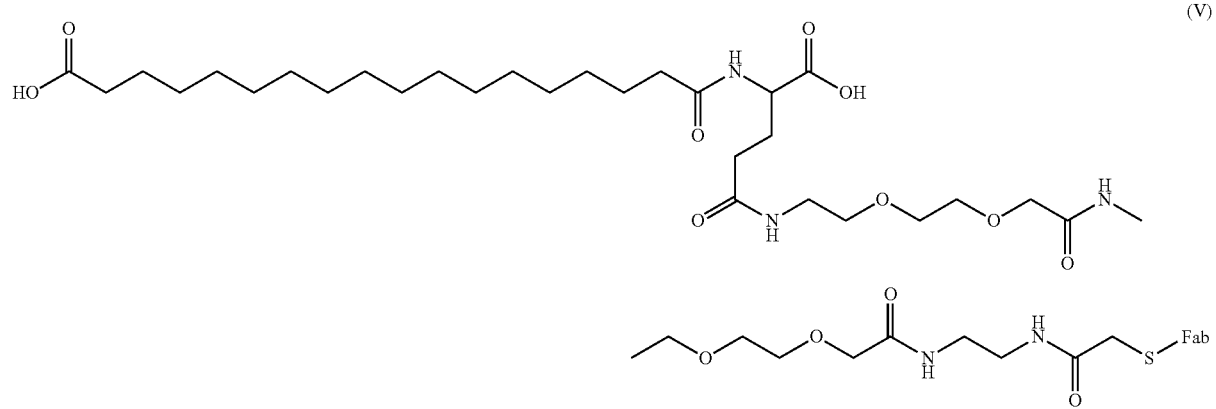

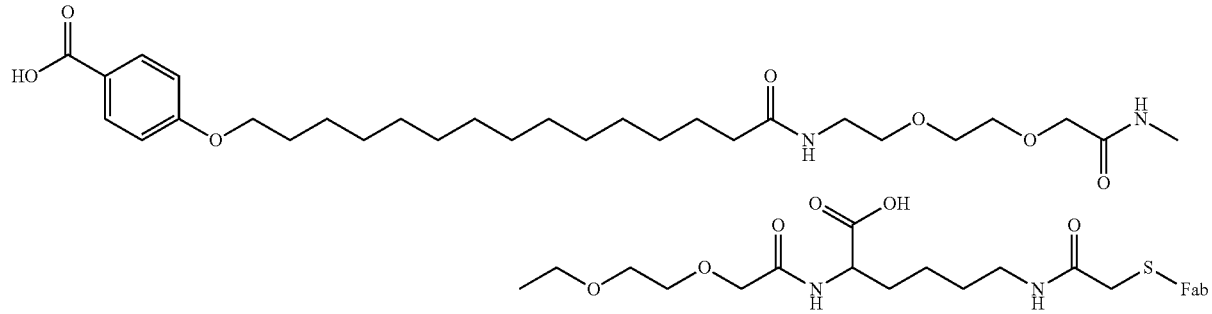

(VI)

Embodiment 7: A monovalent antibody according to any one of embodiments 3-6, wherein said lipophilic moiety is attached to a naturally occurring cysteine residue, preferably the C239 (Kabat numbering) cysteine residue, in the heavy chain of the antibody via a hydrophilic spacer.

Embodiment 8: A monovalent antibody according to any one of the preceding embodiments, wherein said antibody binds to an epitope on DR3, wherein said epitope comprises I43 and/or L45 of SEQ ID NO:1.

Embodiment 9: A monovalent antibody according to any one of the preceding embodiments, wherein said antibody binds an epitope on DR3, wherein said epitope comprises at least one of amino acids G37 to L45 and at least one of amino acids L57 to A59 as set forth in SEQ ID NO:1.

Embodiment 10: A monovalent antibody according to embodiment 9, wherein said epitope comprises amino acids G37 to L45 and amino acids L57 to A59 as set forth in SEQ ID NO:1.

Embodiment 11: A monovalent antibody according to any one of the preceding embodiments, wherein said ligand is a Fab fragment.

Embodiment 12: A monovalent antibody according to any one of the preceding embodiments, wherein said monovalent antibody binds DR3 with a dissociation constant of below 1 nM.

Embodiment 13: A monovalent antibody according to embodiment 12, wherein said monovalent antibody binds DR3 with a dissociation constant of below 500 µM, preferably below 300 µM, preferably below 100 µM, most preferably below 30 µM.

Embodiment 14: A monovalent antibody according to any one of the preceding embodiments, wherein said antibody binds to the CRD1 domain of human DR3.

Embodiment 15: A monovalent antibody, alternatively a bivalent antibody, comprising the three CDR sequences as set forth in SEQ ID NO:16 and the three CDR sequences as set forth in SEQ ID NO:17. In another embodiment, the monovalent antibody according to the invention comprises the three CDR sequences as set forth in SEQ ID NO:10 and the three CDR sequences as set forth in SEQ ID NO:11.

Embodiment 16: A monovalent antibody, alternatively a bivalent antibody, wherein said antibody comprises a human frame work, the CDR3 sequence as set forth in SEQ ID NO:16 and the CDR3 sequence as set forth in SEQ ID NO:17 as well as an "S49A" back mutation in the heavy chain.

Embodiment 17: A monovalent antibody according to embodiment 16, wherein said antibody comprises the three CDR sequences as set forth in SEQ ID NO:16, and the three CDR sequences as set forth in SEQ ID NO:17. In another embodiment, a monovalent antibody according to the invention comprises the heavy chain and light chain as set forth in SEQ ID NOs 16 and 17, respectively.

Embodiment 18: A monovalent antibody according to any one of embodiments 15-17, wherein said antibody is an IgG4 isotype.

Embodiment 19: A monovalent antibody according to any one of the preceding embodiments, wherein said antibody competes with monovalent antibody "0228" for binding to human DR3, wherein the amino acid sequence of the 0228 heavy chain is at set forth in SEQ ID NO:16 and the amino acid sequence of the 0228 light chain is as set forth in SEQ ID NO:17. In another embodiment, the antibody binds to the same epitope as the 0228 antibody.

Embodiment 20: A monovalent antibody according to any one of embodiments 1-14, wherein said antibody comprises the three CDR sequences as set forth in SEQ ID NO:12 and the three CDR sequences as set forth in SEQ ID NO:13.

Embodiment 21: A monovalent antibody according to the invention, wherein said antibody competes with monovalent antibody 0124 for binding to human DR3, wherein the amino acid sequence of the 0124 heavy chain is as set forth in SEQ ID NO:12 and the amino acid sequence of the light chain is as set forth in SEQ ID NO:13. In another embodiment, the antibody binds to the same epitope as the 0124 antibody.

Embodiment 22: A monovalent antibody, alternatively a bivalent antibody, wherein said antibody comprises the three CDR sequences as set forth in SEQ ID NO:18 and the three CDR sequences as set forth in SEQ ID NO:19.

Embodiment 23: A monovalent antibody according to the invention, wherein said antibody competes with monovalent antibody 0130 for binding to human DR3, wherein the amino acid sequence of the 0130 heavy chain is as set forth in SEQ ID NO:18 and the amino acid sequence of the 0130 light chain is as set forth in SEQ ID NO:19. In another embodiment, the antibody binds to the same epitope as the 0130 antibody.

Embodiment 24: A monovalent antibody, alternatively a bivalent antibody, wherein said antibody comprises the three CDR sequences as set forth in SEQ ID NO:20 and the three CDR sequences as set forth in SEQ ID NO:21. (0143).

Embodiment 25: A monovalent antibody according to the invention, wherein said antibody competes with monovalent antibody 0143 for binding to human DR3, wherein the amino acid sequence of the 0143 heavy chain is as set forth in SEQ ID NO:20 and the amino acid sequence of the 0143 light chain is as set forth in SEQ ID NO:21. In another embodiment, said antibody binds to the same epitope as the 0143 antibody.

Embodiment 26: A monovalent antibody, alternatively a bivalent antibody, wherein said antibody comprises the three CDR sequences as set forth in SEQ ID NO:22 and the three CDR sequences as set forth in SEQ ID NO:23. (0152).

Embodiment 27: A monovalent antibody according to the invention, wherein said antibody competes with monovalent antibody 0152 for binding to human DR3, wherein the amino acid sequence of the 0152 heavy chain is as set forth in SEQ ID NO:22 and the amino acid sequence of the 0152 light chain is as set forth in SEQ ID NO:23. In another embodiment, said antibody binds to the same epitope as the 0152 antibody.

Embodiment 28: A monovalent antibody according to the invention, wherein said antibody decreases IFN-gamma (IFN-γ) release in synovial fluid cells from RA patients, wherein said synovial fluid cells are co-stimulated with TL1A. Preferably, the cells are IL-12/IL-18-activated.

Embodiment 29: A monovalent antibody according to the invention, wherein said antibody decreases release of one or more cytokines in Lamina Propria Mononuclear Cells (LPMCs) from intestinal biopsies from CD patients, wherein said cytokines are selected from the list consisting of: IL-6, TNF-α, GM-CSF, and IFN-gamma (IFN-γ), and wherein said LPMCs are co-stimulated with TL1A, IL-12, and IL-18. Preferably, the cells are IL-12/IL-18-activated.

Embodiment 30: A monovalent antibody according to the invention, wherein said antibody decreases release of one or more cytokines in CD4+ T cells, wherein said cytokines are selected from the list consisting of: TNF-α, IL-6, GM-CSF, and IFN-gamma (IFN-γ), and wherein said T cells are co-stimulated by TL1A. Preferably, the cells are IL-12/IL-18-activated.

Embodiment 31: A monovalent antibody according to any one of the preceding embodiments, wherein the antibody is an IgG4 type antibody.

Embodiment 32: A monovalent antibody according to any one of the preceding embodiments, wherein said antibody is conjugated to one or more half life extending moiety selected from one or more of the list consisting of: fatty acids and derivatives thereof, Hydroxy Ethyl Starch (HES), Poly Ethylen Glycol (PEG), hyaluronic acid (HA), heparosan polymers, Phosphorylcholine-based polymers, fleximers, dextran, poly-sialic acids (PSA), an Fc domain, transferrin, albumin, Elastin like peptides, XTEN polymers, albumin binding peptides, and any combination thereof. It follows that the monovalent antibody according to the invention can be conjugated with two or more different types of half life extending moieties.

Embodiment 33: A monovalent antibody according to the invention, wherein said monovalent antibody comprises an Fc domain with reduced effector functions or an Fc domain with increased stability. Preferably, the Fc domain is an IgG1 Fc domain comprising one, two, three, four, or all of the following mutations: L234A, L235E, G237A, A330S, and P331S). Alternatively, the Fc domain may be an IgG4 Fc domain preferably comprising the S241P/S228P mutation.

Embodiment 34: A monovalent antibody according to the invention, wherein said monovalent antibody is conjugated to a half life extending moiety via a glycan, preferably via a sialic acid.

Embodiment 35: A monovalent antibody according to the invention, wherein said antibody is a human antibody.

Embodiment 36: A monovalent antibody according to the invention, wherein said antibody is a humanized antibody.

Embodiment 37: A monovalent antibody according to the invention, wherein said antibody blocks binding of one or more DR3 ligands. It is plausible that DR3 binds to other ligands than TL1A. However, such ligands have not yet been identified.

Embodiment 38: A monovalent antibody (preferably comprising essentially the same paratope as the 27F16A1 antibody) according to the invention, wherein said antibody comprises at least one of the CDR sequences in SEQ ID NO:8 and at least one of the CDR sequences as set forth in SEQ ID NO:9. Preferably, said antibody comprises at two of the CDR sequences set forth in SEQ ID NO:8 and one of the CDR sequence set forth in SEQ ID NO:9. More preferably, said antibody comprises three of the CDR sequences as set forth in SEQ ID NO:8 and one of the CDR sequences as set forth in SEQ ID NO:9. More preferably, said antibody comprises at least one of the CDR sequences as set forth in SEQ ID NO:8 and two of the CDR sequences as set forth in SEQ ID NO:9. More preferably, said antibody comprises at least one of the CDR sequences as set forth in SEQ ID NO:8 and three CDR sequences as set forth in SEQ ID NO:9. More preferably, said antibody comprises one of the CDR sequences as set forth in SEQ ID NO:8 and one of the CDR sequences as set forth in SEQ ID NO:9. More preferably, said antibody comprises two of the CDR sequences as set forth in SEQ ID NO:8 and two of the CDR sequences as set forth in SEQ ID NO:9. More preferably, said antibody comprises three of the CDR sequences as set forth in SEQ ID NO:8 and three of the CDR sequences as set forth in SEQ ID NO:9. Any one of such antibodies according to the present invention may comprise one, two, three, four, five, or six of such CDR sequences, wherein one or two amino acids from this or these CDR sequences has been deleted, added, or mutated into a different amino acid residue—thus resulting in one or more CDR sequences that are different in one or more positions compared to the CDR sequences as set forth in SEQ ID NO:8 and SEQ ID NO:9.

Embodiment 39: A monovalent antibody according to the invention, wherein said antibody competes with monovalent antibody 27F16A1 for binding to human DR3, wherein the amino acid sequence of the 27F16A1 heavy chain is at set forth in SEQ ID NO:8 and the amino acid sequence of the 27F16A1 light chain is as set forth in SEQ ID NO:9. In another embodiment, the present invention relates to antibodies binding to the same epitope as the 27F16A1 antibody.

Embodiment 40: A monovalent antibody (preferably comprising essentially the same paratope as the 27F44A2 antibody) according to the invention, wherein said antibody comprises at least one of the CDR sequences in SEQ ID NO:10 and at least one of the CDR sequences as set forth in SEQ ID NO:11. Preferably, said antibody comprises at two of the CDR sequences set forth in SEQ ID NO:10 and one of the CDR sequence set forth in SEQ ID NO:11. More preferably, said antibody comprises three of the CDR sequences as set forth in SEQ ID NO:10 and one of the CDR sequences as set forth in SEQ ID NO:11. More preferably, said antibody comprises at least one of the CDR sequences as set forth in SEQ ID NO:10 and two of the CDR sequences as set forth in SEQ ID NO:11. More preferably, said antibody comprises at least one of the CDR sequences as set forth in SEQ ID NO:10 and three CDR sequences as set forth in SEQ ID NO:11. More preferably, said antibody comprises one of the CDR sequences as set forth in SEQ ID NO:10 and one of the CDR sequences as set forth in SEQ ID NO:11. More preferably, said antibody comprises two of the CDR sequences as set forth in SEQ ID NO:10 and two of the CDR sequences as set forth in SEQ ID NO:11. More preferably, said antibody comprises three of the CDR sequences as set forth in SEQ ID NO:10 and three of the CDR sequences as set forth in SEQ ID NO:11. Any one of such antibodies according to the present invention may comprise one, two, three, four, five, or six of such CDR sequences, wherein one or two amino acids from this or these CDR sequences has been deleted, added, or mutated into a different amino acid residue thus resulting in one or more CDR sequences that are different in one or more positions compared to the CDR sequences as set forth in SEQ ID NO:10 and SEQ ID NO:11.

Embodiment 41: A monovalent antibody according to the invention, wherein said antibody competes with monovalent antibody 27F44A2 for binding to human DR3, wherein the amino acid sequence of the 27F44A2 heavy chain is as set forth in SEQ ID NO:10 and the amino acid sequence of the light chain is as set forth in SEQ ID NO:11. In another embodiment, an antibody according to the invention binds to the same epitope as the 27F44A2 antibody.

Embodiment 42: A monovalent antibody (preferably comprising essentially the same paratope as the 28F26A3 antibody) according to the invention, wherein said antibody comprises at least one of the CDR sequences in SEQ ID NO:12 and at least one of the CDR sequences as set forth in SEQ ID NO:13. Preferably, said antibody comprises at two of the CDR sequences set forth in SEQ ID NO:12 and one of the CDR sequence set forth in SEQ ID NO:13. More preferably, said antibody comprises three of the CDR sequences as set forth in SEQ ID NO:12 and one of the CDR sequences as set forth in SEQ ID NO:13. More preferably, said antibody comprises at least one of the CDR sequences as set forth in SEQ ID NO:12 and two of the CDR sequences as set forth in SEQ ID NO:13. More preferably, said antibody comprises at least one of the CDR sequences as set forth in SEQ ID NO:12 and three CDR sequences as set forth in SEQ ID NO:13. More preferably, said antibody comprises one of the CDR sequences as set forth in SEQ ID NO:12 and one of the CDR sequences as set forth in SEQ ID NO:13. More preferably, said antibody comprises two of the CDR sequences as set forth in SEQ ID NO:12 and two of the CDR sequences as set forth in SEQ ID NO:13. More preferably, said antibody comprises three of the CDR sequences as set forth in SEQ ID NO:12 and three of the CDR sequences as set forth in SEQ ID NO:13. Any one of such antibodies according to the present invention may comprise one, two, three, four, five, or six of such CDR sequences, wherein one or two amino acids from this or these CDR sequences—thus resulting in one or more CDR sequences that are different in one or more positions compared to the CDR sequences as set forth in SEQ ID NO:12 and SEQ ID NO:13.

Embodiment 43: A monovalent antibody according to the invention, wherein said antibody competes with monovalent antibody 28F26A3 for binding to human DR3, wherein the amino acid sequence of the 28F26A3 heavy chain is as set forth in SEQ ID NO:12 and the amino acid sequence of the 28F26A3 light chain is as set forth in SEQ ID NO:13. In another embodiment, the antibody binds to the same epitope as the 28F26A3 antibody.

Embodiment 44: A DNA molecule encoding a monovalent antibody or ligand according to the invention.

Embodiment 45: An expression vector comprising a DNA molecule according to embodiment 44.

Embodiment 46: A host cell comprising an expression vector according to embodiment 45, or a DNA molecule according to embodiment 44.

Embodiment 47: A method for making a ligand or an antibody according to the invention, wherein said method comprises incubation of a host cell according to embodiment 46.

Embodiment 48: A pharmaceutical composition comprising a compound according to the invention. The composition optionally comprises at least one pharmaceutically acceptable carrier/excipient.

Embodiment 49: Use of a ligand according to the invention or a pharmaceutical composition according to the invention as a medicament.

Embodiment 50: Use of a ligand according to the invention, or a pharmaceutical composition according to the invention for treating an inflammatory disease.

Embodiment 51: Use of a ligand according to the invention, or a pharmaceutical composition according to the invention, for treatment of RA.

Embodiment 52: Use of a ligand according to the invention, or a pharmaceutical composition according to the invention, for treatment of Crohns Disease (CD).

Embodiment 53: Use of a ligand according to the invention, or a pharmaceutical composition according to the invention, for treatment of ulcerative colitis (UC).

Embodiment 54: A method of treating an inflammatory disease, wherein said method comprises administering a ligand according to the invention, or a pharmaceutical composition according to the invention, to a person in need thereof. The inflammatory disease is preferably RA, Crohns disease or ulcerative colitis.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

Example 1

Immunization and Hybridoma Generation

As stated in the following examples it is difficult to produce a soluble form of full length DR3 of high quality due to the cysteine rich nature of this protein. Soluble forms of DR3 tend to be highly aggregated, which can lead to shielding of important ligand-binding regions and make it difficult to raise desired antibody responses upon immunization. A whole range of immunization-regimens have been performed in order to obtain a robust anti-DR3 antibody (Ab) serum titer using both soluble full-length DR3 protein, DR3 protein-derivatives containing only parts of the ECD (like e.g. immunization with only the CRD1 domain) of DR3, and DR3-expressing cells (as described in example 3) for immunization. Immunizations have been performed in different mice strains (BALB/C, RBF and NMRCF$_1$) in order to increase the antibody-repertoire diversity and the likelihood of generating neutralizing anti-DR3Abs. In one example, BALB/C mice were immunized eight times intraperitoneally (IP) with $5 \times 10^6$ DR3-expressing CHO cells with or without incomplete Freunds adjuvant (IFA), followed by 6 IP immunizations with purified hDR3-Fc (see example 3) in IFA. Mice sera were screened for DR3/hTL1A blocking antibodies by FACS as described in Example 4. Mice having a DR3/hTL1A blocking Ab titer received a final boost consisting of a single intravenous injection (i.v.) in the tail vein using DR3-mFc. Three days after boost the mice were sacrificed and splenocytes were fused with X63Ag8653 myeloma cells by standard electrofusion procedure. The fused cells were seeded in 96-well plates and cultured in DMEM (Invitrogen) and HAT selection medium supplemented with FCS (Hyclone) for one week prior to screening for DR3/hTL1A blocking mAbs.

Example 2

Cells for Screening and Immunization

Cells over-expressing transmembrane (TM) DR3 have been developed as an essential tool for use in cell based screening assays and for immunisation of mice.

Production of a stable cell line overexpressing TM DR3 has not been straight-forward. Initially full length DR3 including TM and death domain (DD) (see SEQ ID NO:1 for full AA sequence) was cloned into the pcDNA3.1 expression vector (Invitrogen) and the vector was used for transfection of Ba/F3 cells. However, the DD in full length DR3 leads to cell death in stable cell lines. It was simply not possible to express full length DR3 with an active DD. In order to inactivate the DD in DR3 and still be capable of expressing transmembrane DR3 protein two new constructs were designed and developed. A mutation in SEQ ID NO:1 (L356N) according to Itoh and Nagata, JBC (268) pp. 10932-10937, 1993 who described a similar mutated version for CD95 where the mutation leads to inactivation of the receptor. Deletion of the DD in SEQ ID NO:1 (ΔM339-P417) as determined according to Screaton et al., PNAS (94) pp. 4615-4619, 1997. Both the truncated version and the mutated version was cloned into pcDNA3.1 and expressed in Ba/F3. This resulted in two stable cell lines overexpressing surface DR3. From flow-cytometry (FCM) analysis the expression level for DR3 was found to be highest in the cell line developed with the truncated version of DR3. However, the expression level was still too low for a cell line to be used in screening assay.

It was therefore decided to investigate whether the GS-CHO system from Lonza (Basel, Switzerland) could be used for expression of the truncated version of DR3. The coding cDNA from pcDNA3.1 was transferred to the Lonza expression vector, pEE14.4.

The establisment of stable CHOK1 SV cells were performed according to Lonzas manufacturer's protocol. CHOK1 SV cells were transfected by electroporation. Prior to transfection the pEE14.4 plasmid was linearized by digesting with the AcII restriction enzyme. Ten µg of AcII digested pEE14.4 plasmid was used for transfection of $1 \times 10^7$ CHOK1SV cells by electroporation. Cells were plated into a T75 flask. The day after the transfection selection was initiated by adding L-Methionine sulfoximine (MSX) to a final concentration of 50 µM in CD-CHO medium without glutamax (Invitrogen).

Three weeks after transfection, the cells are purified by using lympholyte-mammal (Cedarlane), transferred to shakerflask and cultured in an incubator shaker at 37° C., 8% $CO_2$ and 125 rpm. The selection pressure was from this point lowered to 25 µM MSX. DR3 expression was analysed by FCM. However the DR3 expression level was very low and it was decided to sort the pool by fluorescence-activated cell sorting (FACS) to increase the expression level. Four days after FACS the pool were tested for DR3 expression by FCM and for the first time DR3 expression was fine (FIG. 2). Unfortunately, after 2-3 weeks the DR3 expression level starts to decrease and the cells could no longer bee used for screening.

Figure 3:
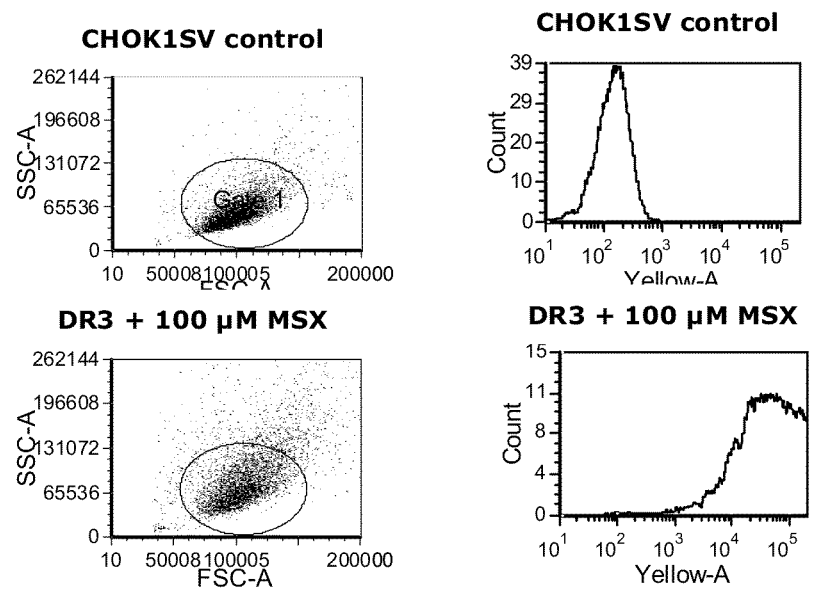
FIG. 3: Stable DR3 expression on CHOK1SV cultured with 100 µM MSX. Expression analysed by FCM.

In an attempt to increase the DR3 level and make the pool more stable the MSX selection pressure was investigated by increasing to 50 µM and 100 µM and in addition the pool was subcloned with ½ cell/well in 4×96W plates. Subcloning resulted in two clones with high DR3 expression level analysed by FCM. However after 1-3 weeks the clones start losing the expression again and appear unstable and thus could not be used for screening. Increasing the MSX selection to 100 µM for the pool resulted in a very fine and high expression level and in addition this could keep a high expression level over time (FIG. 3).

The resulting cell line used for screening and immunisation are therefore a CHOK1 SV transfected with truncated DR3 and cultured in CD-CHO+100 µM MSX.

Example 3

Expression and Purification of Soluble DR3

Figure 4:
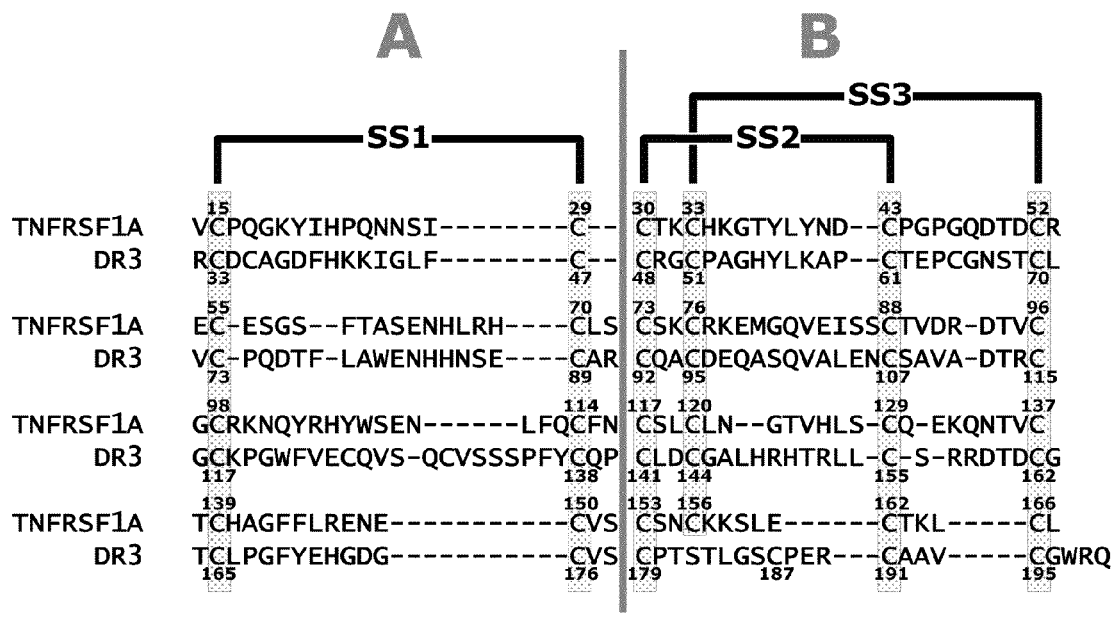
FIG. 4: Sequence alignment of TNFR1 and DR3 extracellular domains. Each line represents a cysteine rich domain (CRD) which again can be divided into A and B sub-domains. The conserved disulfide pattern in CRD, as determined for TNFR1, is highlighted.

Human DR3 is a very cysteine rich protein comprising four cysteine-rich domains (CRD1, CRD2, CRD3 and CRD4) in the extracellular domain (ECD, residues 25-199) and a "death domain" (DD) in the cytoplasmic domain. According to Banner et al., Cell (73) pp. 431-445, (1993) each CRD typically contains six cysteine residues that form three disulfide bounds. In addition each CRD can be subdivided into modules A1 and B2 which are typically observed in conventional members of the TNFR superfamily (J. H. Naismith et al., Trends Biochem. Sci. (23) pp. 74-79, 1998). The sequence for DR3 with predicted CRDs and modules A1 and B2 is shown in FIG. 4.

Production of soluble DR3 has been very difficult, which may be due to the high cysteine content of the protein. Recombinant expression of the ECD of DR3 in human cell lines usually led to the secretion of soluble proteins that contained large amounts of oligomers and high molecular weight complexes, due to the formation of intermolecular disulfide bonds. These protein batches did not bind TL1A and were not active in cellular assays.

Different approaches have been taken to solve the aggregation problems. Initially, the full ECD (25-199) of DR3 was fused to a Fc domain of either mouse IgG1 or human IgG4. Transient production in HEK293 resulted in low yields (<10 mg/L) and a high degree of aggregation. Gel filtration allowed enrichment of the expected dimer, but due to the low yields and high degree of oligomerization, it was initially not possible to obtain a pure fraction. Other purification tags such as biotinylation, FLAG-tag or the trimerization peptide, Tenascin C (TNC) have also been tested, but did not improve results.

In addition, DR3-Fc fusion proteins have been engineered that contained only parts of the ECD of DR3, in order to determine the part of the protein responsible for the oligomerisation. Four proteins were designed as follows:

DR3 (CRD1)-Fc (SEQ ID NO:2)
DR3 (CRD1+A1)-Fc (SEQ ID NO:3)
DR3 (CRD1+CRD2)-Fc (SEQ ID NO:4)
DR3 (CRD1+CRD2+A1)-Fc (SEQ ID NO:5)

The formation of intermolecular disulfide bonds and thereby misfolding correlated with increasing length of the DR3 ECD, probably reflecting the increasing number of cysteines. Concurrently, the yield of protein expression decreased with increasing length of the DR3 EC domain. Gel filtration allowed the purification of mainly dimeric fractions for all these constructs; however, the proteins were not biologically active. Apart from the constructs a number of truncation and cys-deletion constructs were also made in the attempt to pinpoint a single cysteine or a minor region responsible for the oligomerization. However, no single region or specific cysteine seem to be responsible and the entire DR3 sequence seems to be difficult to express in a soluble form.

In addition, a fusion protein between the glutathion S-transferase (GST) and the CRD1 of DR3 has been produced, that was homogenic (SEQ ID NO:6).

Stable expression of the DR3-Fc, comprising the ECD of DR3, a linker containing a TEV cleavage site and the Fc part of human IgG4, in Chinese Hamster Ovary (CHO) cells increased the expression levels and allowed for the isolation of mainly dimeric protein (SEQ ID NO:7). This fraction could compete for TL1A binding to DR3 in a reporter gene assay measuring TL1A induced DR3 signalling.

A number of these proteins have been used for immunization of mice. Some of the batches were further purified to separate out small amounts non-oligomerized DR3. These batches were used for surface plasmon resonance (SPR) binding assays.

Transient Expression in HEK293 Cells:
Vectors:

All the variants of the DR3 proteins were expressed by using the CMV promotor-based expression vectors (pTT vectors). The pTT vectors are generated for transient expression in the HEK293-6E EBNA-based expression system developed by Yves Durocher (Durocher et al. Nucleic Acid Research, 2002).

Cell Maintenance:

HEK293-6E cells were grown in suspension in FreeStyle™ 293 expression medium (Gibco) supplemented with 25 pg/ml Geneticin (Gibco), 1% v/v of the surfactant Pluronic F-68 (Gibco) & 1% v/v Penicillin-Streptomycin (Gibco). Cells were cultured in Erlenmeyer shaker flasks in shaker incubators at 37° C., 8% $CO_2$ and 125 rpm and maintained at cell densities between $0.1-1.5 \times 10^6$ cells/ml.

DNA Transfection:

The cell density of cultures used for transfection was $0.9-1.1 \times 10^6$ cells/ml.

One µg DNA was used per ml cell culture.

The DNA was diluted in Opti-MEM media (Gibco) 30 µl media/pg DNA, mixed and incubated at room temperature (23-25° C.) for 5 min.

293Fectin™ (Invitrogen) was used as transfection reagent at a concentration of 1 µl per µg DNA.

The 293Fectin™ was diluted 30× in Opti-MEM media (Gibco), mixed and incubated at room temperature (23-25° C.) for 5 min.

The DNA and 293Fectin solutions were mixed and left to incubate at room temperature (23-25° C.) for 25 min.

The DNA-293Fectin mix was then added directly to the cell culture.

The transfected cell culture was transferred to a shaker incubator at 37° C., 8% $CO_2$ and 125 rpm.

5-6 days post transfection, cell culture supernatants were harvested by centrifugation, followed by filtration through a 0.22 µm PES filter (Corning).

When possible quantitative analysis of protein production was performed by Biolayer Interferometry using the ForteBio Octet system and protein A biosensors.

Purification of DR3-Fc Proteins

Cell supernatants were loaded directly onto a column with Protein A affinity beads (MabSelect Sure; GE Healthcare) with 20 mM Tris/HCl, pH 8.5 as buffer. Bound proteins were eluted stepwise with 10 mM, 50 mM and 100 mM sodium formiate pH 3.5. Eluted fractions were concentrated and shifted to PBS buffer by ultrafiltration. Gel filtration was carried out on a Superdex200 column (GE Healthcare) with PBS as buffer. Fractions containing dimeric proteins were pooled and concentrated by ultrafiltration. All chromatography steps were performed with an Akta Explorer FPLC instrument (GE Healthcare).

Example 4

Screening for Antibodies Blocking the TL1A:DR3 Interaction Pre-screening of Mice Sera It turned out essential to pre-screen the mice sera for blocking effect before performing fusions, since the mice had a very high difference in degree of blocking effect in sera.

Figure 5:
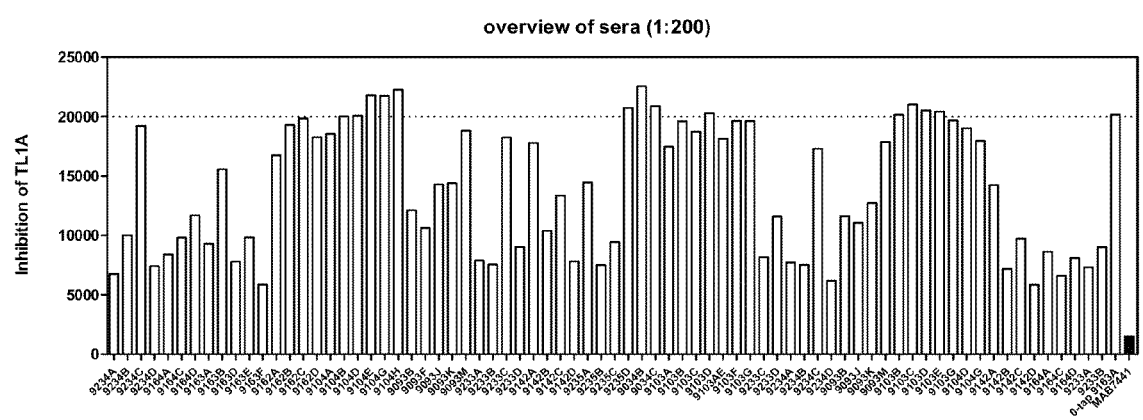
FIG. 5: Individual mice-sera pre-screened for the ability to block humanTL1A binding to CHO cells over-expressing DR3. The right bar (black) is anti-TL1A control (MAB7441 RnD Biosystems).

Mice have been immunized with both DR3 over-expressing cell-lines and DR3 protein. A whole range of immunization-regimens have been performed for obtaining different mice with different antibody-repertoires. Whole cell immunization includes injection of multiple antigens in contrast to single antigen immunization. It has previously been shown that more immunization optimization is needed when using whole cell immunization, as different immunizations-regimens give rise to different antibody repertoires. Screenings mice sera for blocking effect have been an important tool in order to select mice for fusions (FIG. 5).

Screening of Hybridoma Supernatants

In order to select for antibodies against DR3 with the ability to block TL1A binding, the screening plan has been as follows:

As a primary test for DR3 specific antibodies, a high-throughput image-based assay was set up. This was done in an FMAT system, by screening for the ability to bind DR3 transfected CHO cells and counter-screened against wild-type cells (see example 2 for generation of the DR3 cell line).

Assay was done by labelling 50 µl of cell-preparations (50000 cells pr well in 50 µl) to 96 well plates (Greiner, cat no. 65021) together with 25 µl of diluted monoclonal antibodies in titration or hybridoma supernatant undiluted and incubated at 4° C. for 1 hour. After incubation and wash (PBS buffer with 5% Fetal calf serum, centrifuge for 5 minutes at 200 g) 50 µl of secondary antibody pr well (diluted in PBS buffer 1:400) was added and incubated for another 1 hour at 4° C. APC anti mouse were used when screening from RBF mice or Balb/c mice Jacksons #115-136-071 1:400.

Finally cells were washed and transferred to black FMAT plates were read on a PerkinElmer Envision Turbo (FMAT) measuring fluorescence.

The next part of the initial screening was to test for the ability to block the DR3 ligand (TL1A) binding. This was done on the selected DR3 specific hybridoma supernatants, by screening the positive hybridoma-supernatant for the ability to block the TL1A-flag tag binding to DR3 transfected cells. As a control non-transfected cells irrelevant antibodies or supernantants were used.

FCM based inhibitions assay was done by adding 50 µl of diluted monoclonal antibodies in titration or hybridoma supernatant undiluted to the DR3 positive cells (50000 cells pr well) and incubated at 4° C. for 1 hour. After incubation and wash (PBS buffer with 5% Fetal calf serum, centrifuge for 5 minutes at 200 g) TL1A-flag tag (conc. In total volume of 50 µl) where added to 96 well plates (Greiner, cat no. 65021). Again after incubation and wash secondary antibody (APC anti FLAG tag ab from Perkin Elmer in a Final conc. of 5 pg/ml) (diluted in PBS buffer 1:400) was added and incubated for another 1 hour at 4° C.

In parallel a reporter gene assay as described in example 5 where performed in order to detect for agonistic or antagonistic functionality of the antibodies. In house produced TL1A is the mature extracellular domain of TL1A. The TL1A contains an N-terminal FLAG-HIS-TEV tag. FLAG-tag is used for detection in FACS/FMAT, HIS-tag is used for purification and the TEV site allows for optional TEV cleavage and removal of the tag. TL1A produced in E. coli is commercially available from R&D Systems. In house TL1A was produced in HEK cells and contained two N->Q point mutations in order to disrupt the potential N-glycosylation sites. Recombinant cynomolgus TL1A was produced similarly.

Example 5

DR3 Reporter Gene Assay

It was reported by Chinnaiyan et al. 1996 (Science yr:1996 vol:274 iss:5289 pg:990-992) that DR3 signals via NFkappaB and induces apoptosis when DR3 are ectopicly expressed in MCF7 cells. We wanted to utilize the NFkappaB signalling as a reporter and to use a reduced DR3 expression to avoid apoptotic cells.

The HEK293 cell line was stably transfected with a human DR3 expression plasmid and a NFkappaB-luciferase reporter plasmid. The DR3 expression plasmid is based on pcDNA3.1 (hygro)+ and contains a hygromycin resistance gene regulated by the SV40 promoter, the CMV promoter was removed and two heat-shock-elements (HSE), a minimal c-fos promoter and human DR3 coding sequence were inserted. The reporter is based on pGL3-basic and the Luc+ response is regulated by three NFkappaB sites and a minimal interferon promoter. The neomycin resistance gene regulated by the SV40 promoter was inserted in the vector.

A DR3/HEK293 reporter gene cell, named I5, gives a 20-25 fold response in luciferase activity on 40 ng/ml TL1A (R&D Systems) stimulation. The procedure to detect the effect of TL1A, agonizing antibodies and antagonizing antibodies/Fab are as follows. The I5 cells are seeded 20.000 cells/well in polyD-lysine coated black view 96 well plates. The following day TL1A or medium are added to the wells and after 4 hours of incubation the Steady-GLO kit (Promega) is used and luminescence are monitored by a TopCount NXT (Perkin Elmer) instrument. In order to determine a neutralizing effect, antibodies or Fabs are preincubated with cells for 15 minutes before addition of TL1A.

For screening of hybridoma supernatants, all samples were tested in at least duplicates and using both 0 ng/ml, 10 ng/ml TL1A and 50 ng/ml TL1A.

Example 6

Antibodies and Fabs Blocking the TL1A:DR3 Interaction

Monoclonal antibodies (mAb) with specificity for DR3 and tested positive for blocking of TL1A interaction with DR3 were identified. A total of several hundreds specific DR3 mAb have been selected after at least 50 fusions from mice immunized with primarily cells expressing DR3. Further testing of the DR3 specific clones for TL1A inhibition/blocking gave 74 clones. FIG. 6 shows some of the positive antibodies blocking DR3 antibodies. Also included are 2 positive DR3 specific clones without such blocking effect.

All of the mAbs were selected for further studies along with Fab version of the mAbs. Table 1 summarises a study performed and provide the correlation between mAb and Fab numbering and the hydridoma clone numbering.

Figure 7:
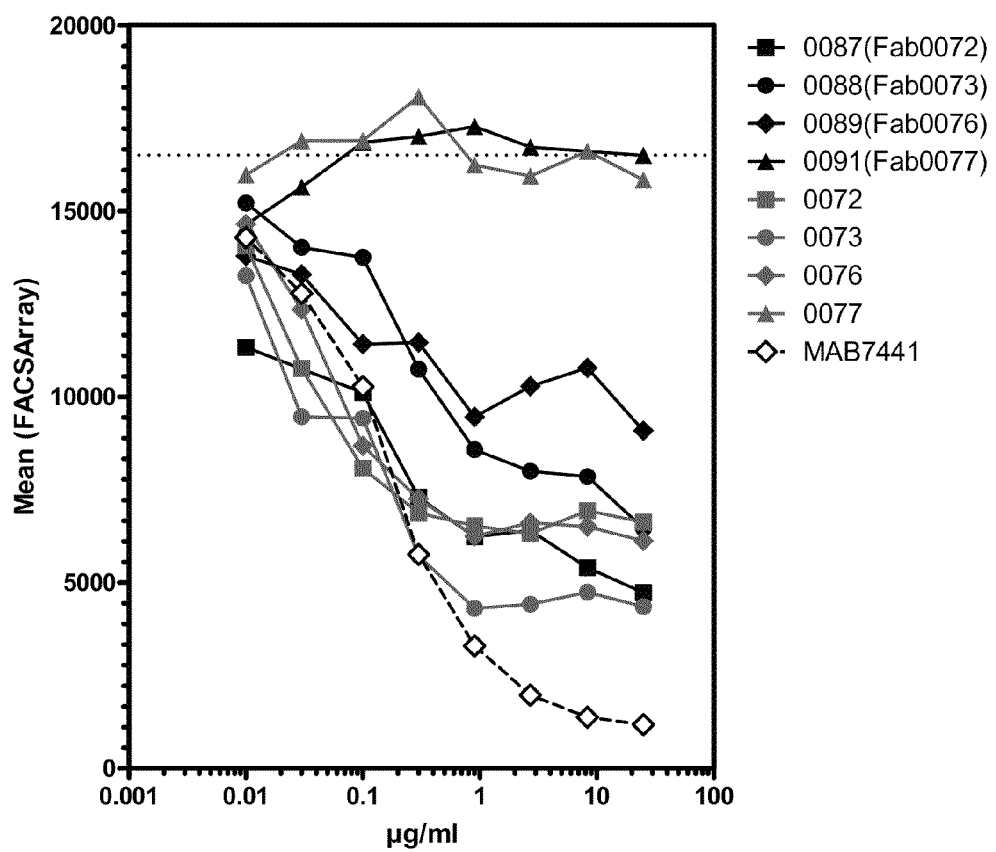
FIG. 7: Titration curves for 3 of the blocking antibodies and non-blocking DR3 specific ab as control—shown with full antibodies and with Fab's.

Antibodies 0072, 0073 and 0076 were found to block the TL1A:DR3 interaction in a dose-dependent manner. The corresponding Fab molecules (0087, 0088 and 0089) retained this ability also in a dose-dependent manner (FIG. 7). Correspondingly, a Fab derived from a DR3 binding mAb that was not able to inhibit the TL1A:DR3 interaction, also did not have this ability (compounds 0077 and 0091, FIG. 7).

Table 2 show examples of Fab characteristics: In total we characterized 46 Fabs for binding, ability to block TL1A-DR3 interaction, TL1A induced T cell activation, binding (more details in other examples). A number of selected Fab's together with controls are shown in the table:

TABLE 2

Fab characteristics

| | | | Fabs tested for displacement/blocking of TL1A binding to hDR3 expressing CHO cells Blocking/displacement of TL1A binding shown as IC50 value (nM) and as max percentage inhibition. | |
|---|---|---|---|---|
| | Inhibition assay | | | |
| Fab ID | Format of Fab | n: | IC50 nM | % inhibition |
| 00228 | IgG4-Cys, hz | 1 | 0.484 | 78 |
| 00123 | IgG4-Ser, chimeric | 8 | 0.443 | 80 |
| 00124 | IgG4-Ser, chimeric | 4 | 1.297 | 79 |
| 00130 | murine Fab | 2 | 1.340 | 73 |
| 00143 | IgG4-Ser, chimeric | 2 | 0.120 | 76 |
| 00152 | IgG4-Ser, chimeric | 1 | 0.512 | 53 |
| 00231 | IgG4-Ser, hz | 1 | 24.680 | 81 |
| 00158 | IgG4-Ser, hz | 11 | No inhib | 10 |
| 00148 | IgG4-Ser, chimeric | 2 | 9.221 | 33 |

TABLE 1

List of mAbs and Fabs selected for further studies and correlation between mAb and Fab numbering and the hydridoma clone numbering.

| Compound | Format | Prepared from | clone name | sequence (see example 9) | Reporter gene assay (see example 7) | Block TL1A to DR3 binding (see example 6) | TL1A-induced CD4+ T-cell proliferation assay (see example 8) |
|---|---|---|---|---|---|---|---|
| 0070 | mAb | hybridoma supernatant | 27F16A1 | + | agonistic | yes | n.d. |
| 0071 | mAb | hybridoma supernatant | 27F38 | n.d. | weak agonistic | no | n.d. |
| 0072 | mAb | hybridoma supernatant | 27F44A2 | + | agonistic | yes | see example 8 |
| 0073 | mAb | hybridoma supernatant | 28F26A3 | + | agonistic | yes | see example 8 |
| 0074 | mAb | hybridoma supernatant | 28F69 | n.d. | weak agonistic | no | n.d. |
| 0075 | mAb | hybridoma supernatant | 29F6 | n.d. | weak agonistic | no | n.d. |
| 0076 | mAb | hybridoma supernatant | 29F8 | n.d. | agonistic | yes | n.d. |
| 0077 | mAb | hybridoma supernatant | 30F1 | n.d. | weak agonistic | no | see example 8 |
| 0087 | Fab | papain cleavage of mAb 0072 | n.a. | + | antagonistic | yes | see example 8 |
| 0088 | Fab | papain cleavage of mAb 0073 | n.a. | + | antagonistic | yes | see example 8 |
| 0089 | Fab | papain cleavage of mAb 0076 | n.a. | n.d. | antagonistic | yes | n.d. |
| 0091 | Fab | papain cleavage of mAb 0077 | n.a. | n.d. | no effect | no | see example 8 | n.a.: not applicable
n.d.: not determined

TABLE 2-continued

Fab characteristics

|  |  |  | Fabs tested for displacement/blocking of TL1A binding to hDR3 expressing CHO cells Blocking/displacement of TL1A binding shown as IC50 value (nM) and as max percentage inhibition. | |
|---|---|---|---|---|
| | Inhibition assay | | | |
| Fab ID | Format of Fab | n: | IC50 nM | % inhibition |
| 00163 | IgG4-Ser, chimeric | 2 | No inhib | 12 |
| 00122 | IgG4-Ser, chimeric | 2 | 5.114 | 33 | n: number of determinations, No inhib: No inhibition seen.

Example 7

Functional Effect of DR3 Antibodies and Derived Fabs

Monoclonal antibodies (mAb) raised against DR3 and tested positive for blockade of TL1A interaction with DR3 were potential neutralizers of DR3 signalling.

The human DR3 reporter gene cell line was incubated with the antibodies for 15 minutes followed by either stimulation with TL1A or addition of medium. The antibodies did only at very high concentrations have a modest neutralization of TL1A action, by contrast they were efficient activators themselves at lower doses.

Table 3 shows the effect of the 0072 antibody. The activation profile of 0072 without addition of TL1A is bell-shaped, indicating that the bivalent antibody activates the DR3 by cross-binding the receptor. The activation increases until a certain concentration whereupon it decreases DR3 activation including the TL1A mediated activation. At higher concentration of antibodies all the paratopes are not any longer occupied by receptor but the antibody is still blocking for TL1A binding and activation and an inhibitory effect is seen. The TL1A specific antibody MAB7441 (R&D Systems) is included to emphasize that the activation of DR3 is TL1A specific.

TABLE 3

The 0227-0000-0072 anti-DR3 antibody tested on human DR3 reporter cell line

| | Medium | 2.5 microg/ml MAb7441 | 0.000256 microg/ml -0072 | 0.00128 microg/ml -0072 | 0.0064 microg/ml -0072 | 0.032 microg/ml -0072 | 0.08 microg/ml -0072 | 4 microg/ml -0072 | 20 microg/ml -0072 | 100 microg/ml -0072 |
|---|---|---|---|---|---|---|---|---|---|---|
| Fold response | 1 | 1.1 | 1.1 | 2.2 | 9.3 | 18.6 | 25.1 | 21.1 | 16.3 | 9.2 |

| | 40 ng/ml TL1A | TL1A + 2.5 microg/ml MAb7441 | TL1A + 0.000256 microg/ml -0072 | TL1A + 0.00128 microg/ml -0072 | TL1A + 0.0064 microg/ml -0072 | TL1A + 0.032 microg/ml -0072 | TL1A + 0.08 microg/ml -0072 | TL1A + 4 microg/ml -0072 | TL1A + 20 microg/ml -0072 | TL1A + 100 microg/ml -0072 |
|---|---|---|---|---|---|---|---|---|---|---|
| Fold response | 32.8 | 3.7 | 33.8 | 37.2 | 40.3 | 41.0 | 38.4 | 34.0 | 27.8 | 18.4 |

Based on these data we hypothesized that a monovalent antibody with affinity to DR3, e.g. a Fab (fragment ab), would probably not cluster the receptors but might still inhibit TL1A binding. The antibodies were cleaved with papain and Fab fragments were purified. The ability of Fab fragments to inhibit TL1A activation of DR3 was tested in the human DR3 reporter assay. Fab fragments from four different DR3 antibodies were tested and the three (0072, 0073 and 0076 corresponding to Fab 0087, 0088, 0089) of them could block TL1A activation (Table 4).

TABLE 4

Fabs derived from anti-DR3 antibodies tested on human DR3 reporter cell line

| | Medium | 2.5 microg/ml MAb7441 | 0.1 microg/ml anti-DR3 molecule | 1 microg/ml anti-DR3 molecule | 10 microg/ml anti-DR3 molecule | 100 microg/ml anti-DR3 molecule |
|---|---|---|---|---|---|---|
| Fold response -0087 Fab | 1.0 | 1.0 | 1.0 | 1.0 | 1.0 | 1.0 |
| Fold response -0088 Fab | 1.0 | 1.0 | 1.1 | 1.1 | 1.1 | 1.0 |
| Fold response -0089 Fab | 1.0 | 1.0 | 1.1 | 1.1 | 1.1 | 1.1 |
| Fold response -0097 Fab | 1.0 | 1.0 | 1.1 | 1.0 | 1.1 | 1.1 |

| | 40 ng/ml TL1A | TL1A + 2.5 microg/ml MAb7441 | TL1A + 0.1 microg/ml anti-DR3 molecule | TL1A + 1 microg/ml anti-DR3 molecule | TL1A + 10 microg/ml anti-DR3 molecule | TL1A + 100 microg/ml anti-DR3 molecule |
|---|---|---|---|---|---|---|
| Fold response -0087 Fab | 24.0 | 2.3 | 5.8 | 2.7 | 2.1 | 2.1 |

TABLE 4-continued

Fabs derived from anti-DR3 antibodies tested on human DR3 reporter cell line

| | | | | | | |
|---|---|---|---|---|---|---|
| Fold response −0088 Fab | 22.6 | 2.0 | 15.2 | 6.3 | 2.9 | 2.8 |
| Fold response −0089 Fab | 22.5 | 1.8 | 17.1 | 11.2 | 7.6 | 7.5 |
| Fold response −0097 Fab | 25.6 | 2.3 | 26.7 | 25.7 | 24.9 | 22.0 |

The fourth Fab 0097 (from mAb 0077) did not inhibit and this is in accordance with mAb 0077 not blocking TL1A binding to DR3 (FIGS. 6 and 7). Table 5 show the ability of the four mAbs (-0072, -0073, -0076 and -0077) to activate the DR3 gene reporter assay in absence of TL1A, also here -0077 prove to be a very poor agonist.

TABLE 5

Anti-DR3 antibodies tested on human DR3 reporter cell line

| | Medium | 2.5 microg/ml MAb7441 | 0.1 microg/ml anti-DR3 molecule | 1 microg/ml anti-DR3 molecule | 10 microg/ml anti-DR3 molecule | 100 microg/ml anti-DR3 molecule |
|---|---|---|---|---|---|---|
| Fold response −0072 antibody | 1.0 | 1.0 | 20.6 | 19.8 | 17.3 | 8.5 |
| Fold response −0073 antibody | 1.0 | 1.0 | 12.8 | 14.4 | 12.8 | 6.9 |
| Fold response −0076 antibody | 1.0 | 1.0 | 18.3 | 22.7 | 17.5 | 9.0 |
| Fold response −0077 antibody | 1.0 | 1.0 | 1.1 | 1.2 | 2.8 | 10.3 |

| | 40 ng/ml TL1A | TL1A + 2.5 microg/ml MAb7441 | TL1A + 0.1 microg/ml anti-DR3 molecule | TL1A + 1 microg/ml anti-DR3 molecule | TL1A + 10 microg/ml anti-DR3 molecule | TL1A + 100 microg/ml anti-DR3 molecule |
|---|---|---|---|---|---|---|
| Fold response −0072 antibody | 24.0 | 2.3 | 29.6 | 24.8 | 23.3 | 13.6 |
| Fold response −0073 antibody | 22.6 | 2.0 | 24.2 | 27.9 | 25.5 | 19.0 |
| Fold response −0076 antibody | 22.5 | 1.8 | 27.5 | 27.8 | 25.6 | 19.5 |
| Fold response −0077 antibody | 25.6 | 2.3 | 23.7 | 23.3 | 25.1 | 24.9 |

Recombinant Fabs were tested in the "I5" human DR3 reporter cell line assay and IC50 was determined when 40 microg/ml TL1A was used, see table 6. Two versions of the 11H08 anti-DR3 -Fabs, H1 L2 and H1 L4, from the patent WO2011/106707, were also included. The H1 L2 (0227-0000-0230) and H1 L4 (0227-0000-0231) has an IC50 of 3.7 nM and 2.8 nM, respectively, whereas 0227-0000-0228 is ten times lower, 320 pM.

TABLE 6

Fab's tested on the human DR3 reporter gene cell line (I5)

| Fab ID | Derived from antibody | IC50 at 40 ng/ml TL1A [Molar] |
|---|---|---|
| 0227-0000-0123 | 27F44 | 188 pM |
| 0227-0000-0228 | 27F44 | 320 pM |
| 0227-0000-0230 | H1L2 (11H08) (WO2011106707) | 3.7 nM |
| 0227-0000-0231 | H1L4 (11H08) (WO2011106707) | 2.8 nM |
| 0227-0000-0124 | 28F26 | 2.4 nM |
| 0227-0000-0130 | 45F36 | 1.4 nM |
| 0227-0000-0143 | 44F434 | 290 pM |
| 0227-0000-0152 | 50F191 | 2.1 nM |
| 0227-0000-0158 | Hz-aTNP | Isotype control |
| 0227-0000-0148 | 5F13 | Not antagonistic |

The cynomolgus DR3 reporter cell line was generated similar to the human reporter cell line. The stable cynomolgus DR3 reporter cell line was named Lyda20 and gives a 10-14-fold response by adding 40 ng/ml human (0227-0000-0011) or cynomogus (0227-0000-0141) soluble TL1A. In Table 7, data for 0123 and 0228 activation of cynomolgus DR3 is show.

TABLE 7

Fabs tested on the cynomolgus DR3
reporter gene cell line (Lyda20)

| Fab ID | IC50 at 40 ng/ml TL1A |
|---|---|
| 0227-0000-0123 | 236 nM |
| 0227-0000-0228 | 628 nM |

The marmoset DR3 reporter cell assay is a transient assay, the NFkappaB-reporter plasmid and marmoset DR3 expression vector regulated by two heat-shock-element and a minimal cFos promoter were transfected into HEK293 cells using FuGene 6 transfection reagent (Roche) two days before stimulation with TL1A. In table 8, activation of DR3 from three species is shown for a selection of Fabs.

TABLE 8

Fabs tested on the transiently transfected primate
DR3 reporter cells

| Fab ID | IC50 of at 40 ng/ml TL1A, human DR3 expressed HEK293 | IC50 of at 40 ng/ml TL1A, cynomolgus DR3 expressed HEK293 | IC50 of at 40 ng/ml TL1A, marmoset DR3 expressed HEK293 |
|---|---|---|---|
| 0227-0000-0123 | 330 pM | 99 nM | 323 pM |
| 0227-0000-0228 | 355 pM | 73 nM | 549 pM |
| 0227-0000-0230 | 4.2 nM | 14 nM | 219 nM |
| 0227-0000-0231 | 4.3 nM | 13 nM | 377 nM |

Fab molecules derived from the 27F44 antibody have a very poor IC50 when tested in the transient cynomolgus DR3 reporter cells, as shown in table 8, 99 and 73 nM. However, the transient marmoset DR3 reporter cell assay showed an IC50 value similar to the transient human DR3 assay.

The 11H08/H1L2 (0227-0000-0230) and 11H08/H1L4 (0227-0000-0231) Fabs has an IC50 of 4.2 and 4.3 nM in the transient human DR3 reporter assay, three times higher IC50 on the transient cynomolgus DR3 reporter assay, 14 and 13 nM, and finally 50 times higher IC50 in the transient marmoset DR3 reporter gene assay, 219 and 377 nM. All numbers are listed in table 8.

Example 8

Binding to Activated Human Cells by Flow Cytometry

Buffy Coats were obtained from normal healthy volunteers from Copenhagen University Hospital. CD4+ T cells were isolated through magnetic bead separation. Cells were activated with 2 ng/ml IL-12, 50 ng/ml IL-18 and 100 ng/ml TL1A (Flag-HIS-TEV-TL1A-produced at Novo Nordisk A/S) and cultured for 5 days. On day 5 cells were stained with 10, 5, 1, 0.5, 0.1 or 0.0001 µg/ml of the anti-DR3 mAb clones 0072, 0073, or 0077, or with Fab fragment clones 0087, 0088 and 0091. A secondary PE conjugated goat-anti-mouse (H+L) was used for detection.

Results: The monoclonal IgG clone 0077, and its corresponding Fab clone 0091 demonstrated only weak binding to the cells. The monoclonal IgG clones 0072 and 0073 showed potent binding to cytokine activated CD4+ T cells with maximal binding observed at concentrations of 1 ug/ml or lower. The corresponding Fab clones (0087 and 0088) bound with similar potency to cytokine activated cells, although slightly lower MFI values were recorded at binding saturation. The greater observed MFI values of IgG treated compared with Fab treated cells was expected since the secondary (detecting) antibody (anti-IgG heavy and light chain) bound to both Fab and Fc parts of the full-length IgG antibody clones, but only to Fab parts of Fab clones (Table 9).

TABLE 9

Mean fluorescence intensity (MFI) values are
shown for IL-12/IL-18/TL1A activated
cells on day 5. Cells are gated on singlets,
live and CD4+ T cells.

| Antibodies or Fab fragments | Concentration used in assay | MFI |
|---|---|---|
| 0072 | 1 µg/ml | 1300 |
| 0073 | 1 µg/ml | 1300 |
| 0077 | 1 µg/ml | 100 |
| 0087 | 1 µg/ml | 500 |
| 0088 | 1 µg/ml | 500 |
| 0091 | 1 µg/ml | 100 |

Functional Assay:

CD4+ T cells were isolated from Buffy Coats through magnetic bead separation using CD4 Rosettesep (Stem cell technologies) and Histopaque (Sigma). T cells ($2 \times 10^5$ cells/well in a 96-well plate) were activated for 5 days with 2 ng/ml IL-12, 50 ng/ml IL-18 and 100 ng/ml TL1A (Flag-HIS-TEV-TL1A; Novo Nordisk) with and without anti-TL1A (1000 ng/ml; MAB7441; RnDSystems) and DR3 mAbs or DR3Fabs (5 or 10 µg/ml) The DR3 mAbs used were 0072, 0073 and 0077. The DR3Fabs used were 0087, 0088 and 0091. Cells were pulsed with [$^3$H]thymidine after 5 days of activation and harvested 16 h later. Alternatively cells were activated for 3 days and subsequent production of cytokines was measured (see examples 6, 15, 18).

TABLE 10

T cell assay: CD4+ T cells from healthy donors activated with IL-12/IL18+TL1A

Inhibition of cytokine production (TNFalpha) represented as
IC50 values (shown as nM) and as max percentage inhibition:
Two representative donors shown together with average of all tested donors.

| Fab ID | Format of Fab | donor 1 IC50 nM | donor 1 % inhibition | donor 2 IC50 nM | donor 2 % inhibition | n: | average IC50 nM | average % inhib |
|---|---|---|---|---|---|---|---|---|
| 00228 | IgG4-Cys, hz | 0.300 | 92.20 | 0.170 | 82.30 | 3 | 0.189 | 89.27 |
| 00123 | IgG4-Ser, chimeric | 0.301 | 83.50 | 0.320 | 75.90 | 22 | 0.208 | 79.64 |

TABLE 10-continued

T cell assay: CD4+ T cells from healthy donors activated with IL-12/IL18+TL1A

Inhibition of cytokine production (TNFalpha) represented as IC50 values (shown as nM) and as max percentage inhibition: Two representative donors shown together with average of all tested donors.

| Fab ID | Format of Fab | donor 1 IC50 nM | donor 1 % inhibition | donor 2 IC50 nM | donor 2 % inhibition | n: | average IC50 nM | average % inhib |
|---|---|---|---|---|---|---|---|---|
| 00124 | IgG4-Ser, chimeric | 1.112 | 52.30 | 1.205 | 41.30 | 4 | 1.329 | 69.29 |
| 00130 | murine Fab | 0.539 | 84.40 | 1.766 | 78.00 | 5 | 0.642 | 82.73 |
| 00143 | IgG4-Ser, chimeric | 0.148 | 76.70 | 0.074 | 66.00 | 5 | 0.125 | 70.03 |
| 00152 | IgG4-Ser, chimeric | 0.183 | 73.50 | | | 1 | 0.183 | 73.50 |
| 00230 | IgG4-Ser, hz | 27.74 | 46.00 | 7.282 | 68.00 | 3 | 15.34 | 55.66 |
| 00231 | IgG4-Ser, hz | 31.73 | 56.00 | 14.91 | 72.00 | 3 | 17.97 | 60.15 |
| 00158 | IgG4-Ser, hz | no inhib | 1.24 | no inhib | 0.75 | 8 | no inhib | −1.80 |
| 00148 | IgG4-Ser, chimeric | no inhib | 9.50 | no inhib | −8.50 | 2 | no inhib | 0.50 |
| 00122 | IgG4-Ser, chimeric | no inhib | 3.90 | no inhib | 10.00 | 4 | no inhib | 6.95 |

T cell proliferation was increased 3-fold by co-stimulation with TL1A. This TL1A-dependent increase was blocked by co-incubation with the anti-TL1A neutralizing control antibody. All anti-DR3 mAbs as well as the Fab 0091 slightly inhibited proliferation at 10 μg/ml, while the Fabs 0087 and 0088 completely blocked proliferation even with the lowest concentration used in the assay. In conclusion, Fabs 0087 and 0088 are very efficient in downregulating the TL1A-dependent co-stimulation of CD4-positive T-cell proliferation.

Example 9

Cloning and Sequencing of Mouse 27F16A1, 27F44A2 and 28F26A3 mAbs

Murine heavy chain and light chain sequences for anti-DR3 antibodies were cloned from the hybridomas: 27F16A1, 27F44A2 and 28F26A3. Total RNA, extracted from hybridoma cells using the RNeasy-Mini Kit from Qiagen, was used as templates for cDNA synthesis. cDNA was synthesized in a 5'-RACE reaction using the SMARTer™ RACE cDNA amplification kit from Clontech. Subsequent target amplification of HC and LC sequences was performed by PCR using Phusion High-Fidelity PCR Master mix (Finnzymes) and the universal primer mix (UPM) included in the SMARTer™ RACE kit as a forward primer.

PCR products were separated by gel electrophoresis, extracted using the GFX PCR DNA and Gel Band Purification Kit from GE Healthcare Life Sciences and cloned for sequencing using a Zero Blunt TOPO PCR Cloning Kit and chemically competent TOP10 E. coli from Invitrogen. Colony PCR was performed on selected colonies using an AmpliTaq Gold Master Mix from Applied Biosystems and 13uni/M13rev primers. Colony PCR clean-up was performed using the ExoSAP-IT enzyme mix (USB). Sequencing was performed at Eurofins MWG Operon, Ebersberg, Germany using either T3/T7 sequencing primers.

Sequences were analyzed and annotated using the Vector NTI program. All kits and reagents were used according to the manufacturer's instructions. From the hybridomas, 27F16A1 and 27F44A2, a single unique murine LC type kappa and a single unique murine HC, subclass IgG1, was identified (SEQ ID NOs 8-11). From 28F26A3 a single unique murine LC type kappa and a single unique murine HC, subclass IgG2a was identified (SEQ ID NOs 12-13). Leader peptide sequences are not included.

BLAST Searches

The translated anti-DR327F16A1, 27F44A2 and 28F26A3 VL and VH amino acid sequences were used as query sequences. BLAST searches were performed against sequences in the GeneSeqP patent database (an internal database with imported sequences from external databases but with no access for external parties) using the BLASTp program. Out of the 100 highest identity scores the highest identity score for VH's was 87.4 (28F26A3) and for VL's it was 97.3 (27F44A2). In conclusion, the VH and VL sequences for anti-DR3 represent novel sequences.

Example 10

Evaluation of Antibody Binding by Flow Cytometry

Human CD4-positive T cells were purified from Buffy coats using CD4 Rosettesep (Stem cell technologies) and Histopaque (Sigma). T cells were stimulated with CD3/CD28 Dynabeads (Invitrogen) at a 1:1 ratio for 4 days in T75 flask at 2 mio CD4 T cells/ml in RPMI supplemented with 10% fcs. Beads were removed using a magnet, and cells were washed twice before titrating in antibodies on 500.000 cells/staining. Binding saturation was measured after incubation with goat-anti-mouse phycoerythrin (Jackson ImmunoResearch) and cells were subsequently analysed by flow cytometry on a BD LSRII. All antibodies reached saturation at 3 μg/ml. Median Fluorescence Intensity are given in table 11, while staining index (MFI Ab/MFI Isotype) is shown in table 12. Abs 0070, 0072, 0073 and 0076 demonstrated stronger binding than 0071 and 0077.

TABLE 11

Median Fluorescence Intensity

| Ab | Median Fluorescent Intensity |
|---|---|
| 0070 | 2329 |
| 0071 | 406 |
| 0072 | 2650 |
| 0073 | 2844 |
| 0076 | 2645 |
| 0077 | 645 |
| IgG1 isotype | 222 |

TABLE 12

Staining Index

| Ab | Staining index |
|---|---|
| 0070 | 10.49 |
| 0071 | 1.83 |
| 0072 | 11.94 |
| 0073 | 12.81 |
| 0076 | 11.91 |
| 0077 | 2.91 |
| IgG1 isotype | 1 |

An aliquot of all antibodies were conjugated using the Phycoerythrin labelling kit lightening link (Innova Biosciences). CD4 T cells were stimulated as described above and beads were removed using a magnet, before washing the cells. Unlabelled antibodies were titration from 0-50 µg/ml final concentration and added to the cells before incubated at 4° C. for 30 min. Cells were washed and directly labelled antibody is added at 2 µg/ml. After 30 min incubation, cells were washed and run on the flow cytometer. All combinations of labelled and unlabelled antibody were tested, and the Median Fluorescence Intensity recorded. Unlabelled antibodies competing for binding of the labelled antibodies are grouped as binding the same bin.

Only abs 0070, 0072, 0073, 0076 were able to stain the activated T cells sufficiently to bin them. As depicted in Table 13 0070, 0072, 0073, 0076 were able to compete for each other, and thus are grouped in the same bin. Most likely these mAbs bind the same epitope, overlapping epitopes or cannot bind simultaneously due to steric hindrance.

TABLE 13

"Bin 1" antibodies Bin 1

| |
|---|
| 0070 |
| 0072 |
| 0073 |
| 0076 |

Example 11

SPR Analyses of the Antibodies and Fab Fragments Binding to Different Domains of DR3

The extracellular moiety of DR3 is located at the aminoterminal portion of DR3 and is comprised of four TNF receptor cysteine-rich domains. Several fusion proteins were expressed and purified which contained parts of the extracellular domain of DR3 of increasing length fused to the Fc domain of a human IgG4. The DR3 proteins used for SPR analysis had been purified to exclude oligomerized material. These proteins were immobilized to a CM5 sensor chip using amine coupling chemistry. Binding of anti-DR3 antibodies termed 0070, 0072, 0073 and 0076, to the different DR3-Fc fusion proteins was tested by means of plasmon surface binding measurements on a Biacore T100 instrument (GE Healthcare). All of these antibodies inhibit binding of TL1A to DR3 in a FACS assay. These 4 antibodies bound to recombinant DR3 (CRD1)-Fc protein that contained only the aminoterminal CRD (SEQ ID NO:2) comprised of amino acids 25-71 of DR3. Another antibody 0077, that did not inhibit TL1A binding to DR3, did not bind to DR3 (CRD1)-Fc (SEQ ID NO:2) but bound to DR3 (CRD1+A1) Fc (SEQ ID NO:3), which contains amino acids 25-90 of DR3, indicating that its epitope or at least part of its epitope is located between amino acids 77 to 90.

The same analysis was also performed for some of the Fab fragments. Fab fragments 0123, 0124, 0130, 0143, 0152, 0219 and 0228 bound all to DR3(CRD1)-Fc (SEQ ID NO:2)

Binding of Fab fragments 230 and 231 to DR3-Fc was also tested by SPR. Both Fab bound to DR3 (ECD)-Fc (SEQ ID NO:7) that contained the complete extracellular domain of DR3, but not to DR3 (CRD1)-Fc (SEQ ID NO:2) nor DR3 (CRD1+A1) Fc (SEQ ID NO:3), indicating that these two prior art Fab fragments do not bind to the DR3CRD1 domain.

Measurement of Binding Kinetics for Anti-DR3Fab Fragments by SPR

The experiments were performed on a Biacore T200 instrument (GE Healhtcare) and analysed with the Biacore T200 Evaluation Software. Anti human IgG antibodies (human IgG capture kit from GE Healthcare) were immobilized on all flow cells of a CM5 sensor chip according to manufacturer's instructions. HBS-EP (GE Healthcare) with 0.1% human serum albumin was used as running buffer. DR3(CRD1)-Fc (SEQ ID NO:2) was captured on the chip at low surface densities between 14 and 45 RU. Fab fragments were diluted to concentrations between 90 and 0.037 nM and subsequently injected for 360 s. The standard dissociation time was 900 s, however due to the high affinities, extended dissociation times of up to 13 000 s were applied for the highest concentrations to determine correct $k_d$ values. Binding curves were measured at 25° C. with a flow rate between 30 and 60 µL/min.

Regeneration was performed with 3 M $CaCl_2$ for 2×20 s. The raw data were double referenced by subtraction of the signals from a reference flow cell without captured ligand and a buffer blank. Determination of the kinetic parameters was performed by fitting with a 1:1 binding model using the Biacore T200 Evaluation Software (GE Healthcare). Average values obtained from 3 different surface densities of DR3(CRD1)-Fc (SEQ ID NO:2) were calculated and are stated in table 14

TABLE 14

$K_D$ values

| Fab | $k_a$ [$M^{-1}s^{-1}$] | $k_d$ [$s^{-1}$] | $K_D$ [M] |
|---|---|---|---|
| 124 | 7.52E+05 | 2.01E−04 | 2.67E−10 |
| 130 | 1.74E+06 | 2.08E−04 | 1.20E−10 |

TABLE 14-continued

| | $K_D$ values | | |
|---|---|---|---|
| Fab | $k_a$ [M$^{-1}$s$^{-1}$] | $k_d$ [s$^{-1}$] | $K_D$ [M] |
| 143 | 3.49E+06 | 5.10E−06 | 1.47E−12 |
| 219 | 3.20E+06 | 3.06E−05 | 9.55E−12 |
| 228 | 3.97E+06 | 3.19E−05 | 8.05E−12 |

Fab Competition Assay

The experiments were performed on a Biacore T200 instrument (GE Healthcare). Anti human IgG antibodies (human IgG capture kit from GE Healthcare) were immobilized on all flow cells of a CM5 sensor chip according to manufacturer's instructions. HBS-EP (GE Healthcare) with 0.1% human serum albumin was used as running buffer. DR3 (ECD)-Fc (SEQ ID NO:7) was captured at surface densities between 700 and 1200 RU. Fab fragments were used at concentrations of 20 µg/mL. A dual injection of 2 Fab fragments was performed for 300 and 150 s, respectively, followed by regeneration with 3 M CaCl$_2$ for 2×20 s. Binding responses of the Fab fragments were analysed with Scrubber (BioLogic Software).

Fab fragments, which could not bind simultaneously to DR3 (ECD)-Fc, were considered to belong to the same epitope bin. As shown in table 15, Fab fragments 124, 130, 143 and 228, which are all directed against the CRD1 domain, fall into the same epitope bin. Likewise Fab fragments 230 and 231, which have the same CDR domain, also belong to the same epitope bin, different from the CRD1. Fab fragments 148 and 163 do not compete with any of the other Fab and are therefore falling into separate epitope bins. Fab fragment 148 does not compete with 124, 130, 143 and 228, when injected as 2. antibody, indicating that it belongs to a different bin. However, when 148 is bound first, neither 130, 143 or 228 do bind any longer, suggesting that there either is sterical hindrance or conformational change of DR3-Fc, that precludes binding of the other Fab fragments.

TABLE 15

Fab competition for binding DR3-Fc measured by SPR.

| | 2. Fab | | | | | | | |
|---|---|---|---|---|---|---|---|---|
| 1. Fab | 124 | 130 | 143 | 148 | 163 | 228 | 230 | 231 |
| 124 | − | − | − | + | + | − | + | n.t. |
| 130 | − | − | − | + | + | − | + | n.t. |
| 143 | − | − | − | + | + | − | + | n.t. |
| 148 | n.t. | − | − | − | + | − | + | + |
| 163 | n.t. | n.t. | + | + | − | + | + | + |
| 228 | n.t. | n.t. | − | + | + | − | + | + |
| 230 | + | + | + | + | + | + | − | − |
| 231 | n.t. | n.t. | + | + | + | + | − | − |

+: simultaneous binding of both Fab; −: no binding of 2. Fab; n..t.: not tested

Competition Assay

As shown in table 16, Fab fragments 228, 231, 230 and 148 were tested for ability for block Mab binding of 0107 (Mab of 0228) and 0121(Mab of 148) binding to DR3 expressing cells on FACS. Fab fragments 230 and 231 can not compete any of Mabs and can bind simultaneously with Mab 017 and Mab 0121.

TABLE 16

Competition assay performed by FACS

Competition assay
Fabs tested for blocking of binding Mab
using up to 1:10000 excess Fab.

| | MAB ID | |
|---|---|---|
| Fab ID | 0107 (murine Mab 0228) | 0121 (murine Mab of 0148) |
| 0228 | Inhibits from molar ratio Mab/Fab 1:1 | No inhibition |
| 0230 | No inhibition | No inhibition |
| 0231 | No inhibition | No inhibition |
| 0148 | Inhibits from molar ratio Mab/Fab 1:100 | Inhibits fully from molar ratio Mab/Fab 1:3 |

Example 12

Mapping the Epitope of Fab-0228 by Mutagenesis of DR3

In order to determine which amino acids in the CRD1 of human DR3 are responsible for interaction with the -0123 Fab, a few DR3 mutants were generated. The three mutations, R29Q, I43N and L45V were made by site-directed mutagenesis (Quikchange, Stratagene). The mutated DR3 expression plasmids and the NFkappaB-Luc reporter plasmid were transiently transfected into HEK293 cells and the cells were shortly preincubated with anti-DR3 anti-Fab-0228 and subsequently stimulated with human TL1A for four hours. The luciferase activity was assayed by using Steady-GLO (Promega) and monitored on a TopCount NXT (Perkin Elmer). The R29Q was neutralized slightly better than the human wildtype, whereas both I43N, L45V and the combined mutants I43N/L45V were neutralized much less efficiently, see table 17.

The anti-Fab-0123 was also tested and the ranking was similar to the -0228; R29Q>WT>L45V>I43N>I43N-L45V. Thus, residues I43 and L45 are very important for maintaining the binding affinity of 0228 to DR3. These residues are therefore most likely part of the binding epitope. In contrast, R29 does not seem to be essential for the 0228 binding to DR3 since the affinity is maintained and even slightly improved when this residue is mutated. However, since this position affects the 0228 binding it is of structural importance for the binding epitope.

TABLE 17

Fabs tested on the transiently transfected primate DR3
reporter cells, IC50 of Fab upon stimulation by TL1A

| Fab ID | Human DR3 | R29Q | I43N | 45V | I43N/L45V |
|---|---|---|---|---|---|
| 0227-0000-0228 | 645 pM | 372 pM | 68 nM | nM | 149 nM |

Example 13

Anti-DR3 Humanization

The sequence of 0072 was obtained from cloning of the hybridoma 27F44A2. All numbering used in this example refers to the Kabat numbering scheme.

```
>0072VH (CDRs marked with bold)
                                                       (SEQ ID NO: 10)
EVKLVESGGGLVKPGGSLKLSCSASGFAFSNYDMSWVRQTPEKRLEWVAAFSSDGYTFYP

DSLKGRFTISRDNARNTLYLQMSSLGSEDTALYCCARHADYANYPVMDYWGQGTSVTVSS

>0072VL (CDRs marked with bold)
                                                       (SEQ ID NO: 11)
DIVLAQSPASLLVSLGQRATISCRASKSVSTSGYSYMHWYQQKPGQPPKLLIYLASNLES

GVPARFSGSGSGTDFTLNIHPVEEEDAATYYCQHSRELPLTFGAGTMLELKR
```

A sequence analysis of 0072 reveals a free cysteine at position 91 of the heavy chain, that must be removed during the humanization.

A 3D model of 0072 was build using standard techniques in MOE [available from www.chemcomp.com] and all residues within 4.5 Å of the effective CDR regions (VH: 31-35B, 50-58, 95-102; VL: 24-34, 50-56, 89-97) are defined as mask residues. Mask residues are all potentially important for sustaining the binding in the CDRs.

The mask residues includes positions 2, 4, 27-37, 47, 50-59, 69-71, 78, 91-103 for the heavy chain and positions 3-5,7,23-36, 46-60, 62, 65, 67, 69-71, 87-98 for the light chain.

Using germline searches and manual inspection VH3_13 and JH4 were identified as an appropriate human germline combination for the heavy chain and VKI_02 and JK4 were identified as the appropriate human germline combination for the light chain.

The humanization can now be performed with the following rules:
  Residues outside the mask are taken as human.
  Residues inside the mask and inside the Kabat CDR are taken as murine.
  Residues inside the mask and outside the Kabat CDR with mouse/germline consensus are taken as the consensus sequence.
  Residues inside the mask and outside the Kabat CDR with mouse/germline difference are subject to potential back mutations.

Grafting the effective CDR regions of 0072 into the germlines forms the basic humanization construct of 0072, hz0072.

The only differences compared to the murine CDRs are in CDR_H2

Any discrepancy between 0072 and hz0072 in a mask residue will create a potential backmutation and the list includes hz0072VH: T28A, S49A, Y91C hz0072VL: Q3V, M4L, T5M, S60A In order to investigate all potentially humanized mAbs all combinations of the above mutants have to be produced.

The Fab proteins listed in Table 18 were expressed in HEK293 6E cells and expression levels of each variant were compared as evaluated by SDS-PAGE gel. Results in Table 18 showed that all the variants that contained the germline Tyr at site-91 of heavy chain (compound 0169, 1070 and 0171) had dramatically improved expression level comparing to those that contained other replacement, either Cys (compound 0172) or Ser (compound 0173 or 0174), at this site. Also from Table 18, human version of Met or murine version of Leu at site-4 of light chain did not have obvious effect on the expression level. This indicated that Y91 in the heavy chain is critical to the improvement of expression level of the fully-grafted version of 0072.

```
1. >hz0072VH
                                                       (SEQ ID NO: 28)
2. EVQLVESGGGLVQPGGSLRLSCAASGFTFSNYDMSWVRQATGKGLEWVSAFSSDGYTFYP

3. GSVKGRFTISRENAKNSLYLQMNSLRAGDTAVYYCARHADYANYPVMDYWGQGTLVTVSS

4.

5. >hz0072VL
                                                       (SEQ ID NO: 29)
6. DIQMTQSPSSLSASVGDRVTITCRASKSVSTSGYSYMHWYQQKPGKAPKLLIYLASNLES

7. GVPSRFSGSGSGTDFTLTISSLQPEDFATYYCQHSRELPLTFGGGTKVEIK
```

TABLE 18

Comparison of expression level of Fab by variants of anti-DR3 Fab that had mutations on site-91 of heavy chain or site-4 of light chain. The variants were generated on the humanized anti-DR3 0072 with backmutations of HC_T28A_S49A and LC_Q3A_T5A_S60A. HC_Y91 is the humanized version; Y91C is the murine version; Y91S is to mutate Y91 to an irrelevant amino acid Ser. LC_M4 is the humanized version; LC_M4L is the murine version. Expression level was evaluated by SDS-PAGE gel; "++++" represents high expression level of >50 mg/L, and "+" represents poor expression level.

|  | Mutation site | | |
|---|---|---|---|
| Compound name | HC_91 | LC_4 | Expression level |
| 0169 | Y91 | M4L | ++++ |
| 0170 | Y91 | M4 | ++++ |
| 0171 | Y91 | M4 | ++++ |
| 0172 | Y91C | M4L | + |
| 0173 | Y91S | M4L | + |
| 0174 | Y91S | M4 | + |

Selection of Back Mutation

The potential advantage of inserting a back mutation were evaluated based on expression, potency and affinity screening as well as by biophysical characterization.

Expression pattern: The expression levels of various humanized versions of 0072 including various back mutations (BM's) were evaluated transiently in HEK293-6E (see example 3 for transient expression in HEK293-6E).

In addition to the hz0072 the following BM's were evaluated individually regarding expression:
LC: T5A and S60A
HC: T28A and S49A The experiment was performed in triplicates. Cells were grown 5 days post transfection. Media were harvest and the expression levels were measured by forteBIO's Octet using protein G sensors.

The result show that the BM S49A on HC resulted in a 2 fold increase compared to hz0072 expression. Neither of the other BM had the capability to increase expression level (Table 19).

TABLE 19

Relative expression level of the heavy chain (HC) with back mutation and the light chain (LC) with back mutation and compared to the wild type (WT) that is set as 100% expression level.

|  | Average (%) | Stdev |
|---|---|---|
| hz0072 | 100 | 0.06 |
| hz0072 T28A(VH) | 91.7 | 6.02 |
| hz0072 S49A(VH) | 251.2 | 4.58 |
| hz0072 T5A(VL) | 45.7 | 1.26 |
| hz0072 S60A(VL) | 63.6 | 2.17 |

Biophysical Characterization

The thermostability of the humanized Fabs was measured using differential scanning fluorimetry (DSF). DSF was performed using a MyiQ Real-Time PCR detection system (Bio-rad Laboratories, Inc). Samples in PBS at pH 7.4 at a final concentration of 0.3 mg/ml were placed in sealed 96 well PCR plates and 2000 times diluted stock solution of the dye Sypro Orange, which was used to monitor the protein unfolding transition. The fluorescence intensity was measured with excitation/emission wavelength: 480/575 nm. Table 20 shows the thermostability of the humanized Fabs. The results show the two Fabs with back mutations (228 and 229) had the same thermostability (Tm) at 71° C., whereas the humanized Fab without back mutations (227) had a decreased thermostability at 66° C.

TABLE 20

$T_m$ (denaturation temperature) values are shown for the humanized Fabs.

| Fab | $T_m$ (° C.) |
|---|---|
| hz0072 (227) | 6 |
| hz0072 S49A(VH) (228) | 1 |
| hz0072 S49A(VH) S60A(VL) (229) | 1 |

Selection of IgG4 Backbone Using Biophysical Evaluation

The IgG1 and IgG4 isotypes of the humanized Fabs were measured at 3 mg/ml in PBS at pH 7.4 using Bioanalyser to look at the fragmentation patterns. An Agilent 2100 Bioanalyzer was used to look at fragmentation patterns. The kit was Agilent Protein 230, and the marker used was Protein 230 Ladder with 7 peaks. Non-reduced samples were prepared with 2 μl sample, 2 μl Mill-Q water, 2 μl sample buffer and 1 μl 0.5 M N-ethylmaleimide (NEM dissolved in $CH_3CN$). All samples were heated to 100° C. for max. 5 minutes.

Table 21 shows the Bioanalyser data of the integrated amount of free LC for the Fabs at non-reduced conditions. The results show that all the IgG4 Fabs all have less free LC in non-reduced conditions compared to the IgG1 Fabs.

TABLE 21

Integrated peak values of free LC in non-reduced conditions for IgG1 and IgG4 humanized Fabs.

| Fab | gG1 | gG4 |
|---|---|---|
| hz0072 | 1.9 | .0 |
| hz0072S49A(VH) | .6 | .6 |
| hz0072S49A(VH) S60A (VL) | .2 | .7 |

After extensive potency and affinity screening, expression analysis and stability studies as described above the final humanized candidate was selected as the IgG4 version of hz0072VH S49A, hz0072VL with the following sequence:

```
 8.  >hz0072VH_S49A
                                                                    (SEQ ID NO: 16)
 9.  EVQLVESGGGLVQPGGSLRLSCAASGFTFSNYDMSWVRQATGKGLEWVAAFSSDGYTFYP
10.       GSVKGRFTISRENAKNSLYLQMNSLRAGDTAVYYCARHADYANYPVMDYWGQGTLVTVSS
11.       >hz0072VL
                                                                    (SEQ ID NO: 17)
12.       DIQMTQSPSSLSASVGDRVTITCRASKSVSTSGYSYMHWYQQKPGKAPKLLIYLASNLES
13.       GVPSRFSGSGSGTDFTLTISSLQPEDFATYYCQHSRELPLTFGGGTKVEIK
```

This candidate has no free cysteine in the variable domain.

Example 14

Purification of Recombinant Fab Fragments

Recombinant Fab fragments were purified by chromatography steps using an Äkta Explorer FPLC system (GE Healthcare). Cell culture supernatants containing recombinant mouse Fab were diluted in order to reduce the conductivity below 2 mS. Depending on the theoretical pH of the Fab fragment, either anion or cation exchange chromatography was performed using MonoQ or MonoS columns (GE Healthcare). Fab fragments were bound to the column in a buffer of low ion strength at pH values between 5 and 8.5 and eluted with a salt gradient up to 1 M NaCl. Gel filtration with a Superdex200 column (GE Healthcare) and PBS as buffer was performed to remove oligomeric Fab complexes.

Chimeric Fab fragments, containing the constant part of human kappa immunoglobulin light chain, were purified by affinity purification with KappaSelect (GE Healthcare) according to manufacturer's instructions, followed by gel filtration to remove high molecular weight complexes.

Generation of Fab by Papain Cleavage of mAb

Fab fragments were generated by cleavage of mAb using the Pierce Fab Preparation Kit (Thermo Scientific) according to manufacturer's instructions. In some cases, gel filtration with a Superdex200 column (GE Healthcare) and PBS as buffer was performed to remove high molecular weight forms.

Example 15

Cytokine Release from or Proliferation of Primary Human T Cells

CD4+ T cells isolated from Buffy Coats through magnetic bead separation using CD4 Rosettesep (Stem cell technologies) and Histopaque(Sigma) were stimulated in the absence of TCR activation, with cytokines IL-12 (2 ng/ml), IL-18 (50 ng/ml) with and without 100 ng/ml TL1A (Flag-His-TEV-TL1A; Novo Nordisk). T cell proliferation and cytokine release was measured. Supernatants from CD4+ T cells ($2\times10^5$ cells/well) stimulated for 48 h were harvested and analysed for cytokine release by Bioplex. T cell proliferation was measured after 5 days.

IL-12 (2 ng/ml), IL-18 (50 ng/ml) and 100 ng/ml TL1A (Flag-His-TEV-TL1A; Novo Nordisk). treated CD4+ T cells demonstrated 6-fold increased T cell proliferation compared to IL-12/IL-18 treated T cells. The 0123 and 0124 Fabs totally blocked the induced T cell proliferation already at a concentration of 0.16 µg/ml of the Fab while the corresponding mAb 0072 and 0108 did not affect T cell proliferation (FIG. 8).

The released cytokines IL-6, IFNγ, GM-CSF and TNFα were all induced after 48 hours by TL1A by IL-12/IL-18 treated CD4+ T cells. TNFα was significantly (p=*) blocked by the anti-DR3 Fab 0124, compared to a DR3 binding non-blocking Fab 0091 (Table 22).

TABLE 22

| Cytokines | +TL1A (fold upregulation compared to IL12/IL18 activated T cells) | +TL1A+anti DR3 Fab (fold downregulation compared to IL12/IL18 activated T cells) |
|---|---|---|
| IL-6 | 16 (p = 0.051) | 13.3 (p = 0.08) |
| IFNγ | 1.2 (p = 0.025) | 1.1 (p = 0.08) |
| GM-CSF | 7.5 (p = 0.04) | 7.9 (p = 0.08) |
| TNFα | 4.4 (p = 0.0007=) | 5 (p = 0.025) |

Example 16

Conjugating a Lipid Moiety to a Fab

NAP-25 columns, cat#17-0852-02 from GE Healthcare

Hitrap Q-sepharose FF column (code: 17-5156-01) from GE Healthcare

TSPP: Triphenyl phosphine-3, 3',3"-trisulfonic acid trisodium salt hydrate, cat#39538, from Alfa Aesar TDSPP: Bis(p-sulfonatophenyl)phenylphosphine dihydrate dipotassium salt, cat#151888-20-9, from Strem Chemicals TEA: triethanolamine, product nr.: 90279 from Sigma Ethyleneglycol, cat#1.00949.1000 from MERCK NaCl: Code: 207790010 from Acros Organics EDTA, disodium salt, dihydrate cat#SC-29092 from ChemCruz PBS Tablets, cat#18912-014 from GIBCO Vivaspin 20, 10000 MWCO, PES membrane, cat#VS2001 from Sartorius PD10 G-25 columns, cat#17-0851-01 from Ge Healthcare Abbreviations CV: column volumes FLD: fluorescence detection MQ: MilliQ water (highly purified water)

m/z: mass to charge ratio

MS: mass spectrometry

M+H: mass of a singly protonated species

HPLC: high pressure liquid chromatography

RP: reversed phase

LC-MS: liquid chromatography-mass spectrometry

NMR: nuclear magnetic resonance spectroscopy
rt or RT: room temperature
Boc: tert butyloxycarbonyl
O-t-Bu: tert butyl ester
t-Bu: tert butyl
DCM: dichloromethane, $CH_2Cl_2$, methylenechloride
DIC: diisopropylcarbdiimide
DIPEA: N,N-diisopropylethylamine
DMF: N,N-dimethylformamide
DMSO: dimethylsulfoxide
Fmoc: 9H-fluoren-9-ylmethoxycarbonyl
Lys(Mtt)-OH: (S)-6-[(Diphenyl-p-tolyl-methyl)-amino]-2-amino-hexanoic acid
Thx: trans-4-aminomethylcyclohexancarboxylic acid
NMP: N-methylpyrrolidin-2-one
OEG: (2[2-(amino)ethoxy]ethoxy)acetic acid
TFA: trifluoroacetic acid
THF: tetrahydrofuran
TIS: triisopropylsilane
TNBS: trinitrobenzene sulfonic acid
HC: heavy chain
LC: light chain
wt: wild type
Amino acid abbreviations follow IUPAC conventions.
Buffer abbreviations follow Stoll, V. S, and Blanchard, J. S., *Methods of Enzymology*, 182, 1990, Academic Press, 24-38.

Conjugations, General Considerations

Fab's for conjugation with hydrophobic protraction groups were constructed with an unpaired cysteine at or near the C-terminus of the heavy chain (HC). This cysteine was intended for conjugations with thiophilic alkylation reagents bearing eg. maleimide or halo-acetyl groups. The Fab's were expressed as molecules with a disufide bonded cysteinylation to the mutated Cys. In order to free the mutated Cys for reaction with alkylation reagents, it was reduced using a phosphine reagent. After reduction, the protein was separated from the reducing reagent and subjected to alkylation by adding the alkylation reagent. Finally, the conjugate was purified by standard low pressure chromatography.

4-(1H-Tetrazol-16-yl-hexadecanoylsulfamoyl)butanoyl-OEG-γGlu-γGlu-OEG-$N^ε$(C(O)$CH_2$Br)Lys-OH (Albumin Binder I)

Compound I was synthesised on solid support according scheme 1, in 1 mM scale using standard Fmoc-peptide chemistry on an ABI433 synthetizer (Applied Biosystems). The peptide was assembled on a Fmoc-Lys(MTT)-Wang resin using Fmoc-OEG-OH and Fmoc-Glu-OtBu protected amino acids. 4-(16-1H-Tetrazol-5-yl-hexadecanoylsulfamoyl)butyric acid was manual coupled using DIC/NHS in DCM/NMP, 2 eq. over night, TNBS test showed the reaction to be completed. The resin was then treated with 50 mL DCM/TFA/TIS/water (94:2:2:2) in a flowthrough arrangement until the yellow colour disappeared, ~20 min. followed by washing and neutralizing with DIPEA/DMF. Bromo acetic acid (4 mM) in DCM/NMP (1:1) was activated with a 1 mM mixture of NHS and DIC, filtered and added to the resin with addition of further 1 mM of DIPEA. After 1 hr the reaction was completed. The resin was treated with 80 mL TFA/TIS/water (95:2.5:2.5) for 1 hr. Evaporated with a stream of $N_2$, precipitated by addition of $Et_2O$ and washed with $Et_2O$ and dried. Crude product was purified on preparative HPLC (2 runs), with a gradient from 30-80% 0.1 TFA/MeCN against 0.1% TFA in water. Fractions were collected and lyophilized with ~50% MeCN affording compound I.

TOF-MS: mass 1272.52 (M+1)

The above example shows that it is possible to prepare albumin binder compound I in high purity using solid phase synthesis.

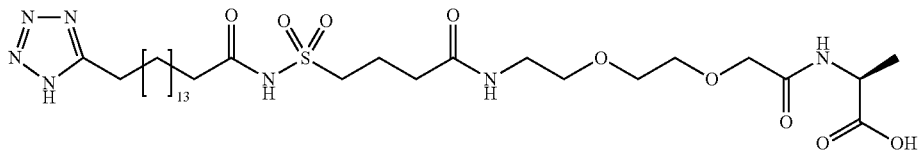

(Compound I)

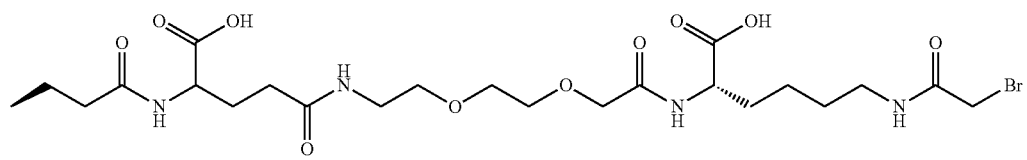

Scheme 1
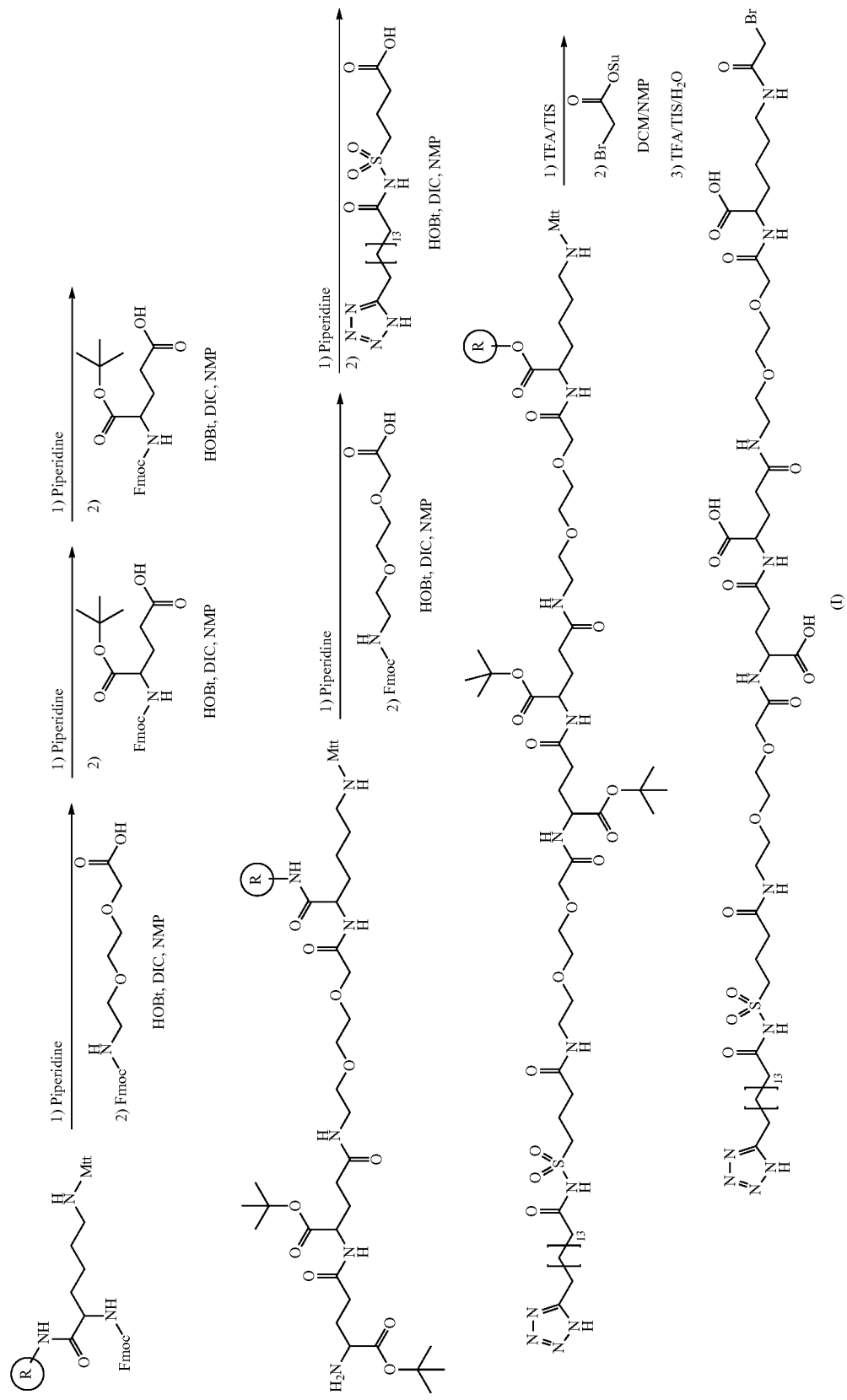

Conjugation of Fab 0120 to Albumin Binder I

Fab 0120 (25 mg, 0.53 umol, 4.2 mg/ml) in PBS buffer was mixed with a solution of triphenylphosphine-3,3',3" trisulfonic acid trisodium salt hydrate (TSPP, 40 mg/ml, 350 ul, final conc. 3.7 mM) in 20 mM triethanolamine, 2 mM EDTA, pH 8.5. The reaction mixture was incubated at r.t. for a period of 150 min. Small molecular weight substances were then removed by buffer exchange on three NAP-25 columns equilibrated and eluted with 20 mM triethanolamine, 2 mM EDTA, 400 mM NaCl, pH 8.5. The buffer exchanged reduced Fab-solution was then mixed with a solution of albumin binder I (490 ul, 16 mM, final conc: 0.8 mM) in 20 mM triethanolamine 2 mM EDTA, 400 mM NaCl, pH 8.5. The reaction mixture (approx. 9.5 ml) was incubated at r.t. for a period of 20 hours and then diluted with 10 ml of buffer 20 mM triethanolamine, 10% ethylenglycol, pH 8.0. Subsequently, the mixture was buffer exchanged on four NAP25 columns equilibrated with 20 mM triethanolamine, 10% ethylenglycol, pH 8.0. The buffer exchanged material was loaded to a 5 ml Hitrap Q-sepharose FF column equilibrated with 20 mM triethanolamine, 10% ethylenglycol, pH 8.0 using an Akta Puifier 100 system (GE Healthcare). Unbound material (incl. the inconjugated Fab) was washed out using this buffer and the product was eluted using a linear gradient of 20 mM triethanolamine, 10% ethylenglycol, 1 M NaCl, pH 8.0 over a period of 1.5 hours. The product eluted at approx. 380 mM NaCl with a symmetric peak profile. Relevant fractions were pooled, concentrated by ultra-filtration a using Vivaspin 20 devices at 3500 g (10000 MWCO, Sartorius) and finally buffer exchanged to PBS buffer. The final isolated product was 11.9 mg (48%), at a concentration of 1.7 mg/ml determined by A280 measurement. SDS-PAGE and MS analysis confirmed the identity of the product (found m/z 49919 (M+H), calc. 49917 (M+H)).

The above example shows a successful, site-specific conjugation of the Fab with the albumin binder I. The conjugation gives rise to a product in good yield and high purity.

Conjugation of Fab's to Albumin Binder II-VI

Albumin binders II-VI has the structures as shown below

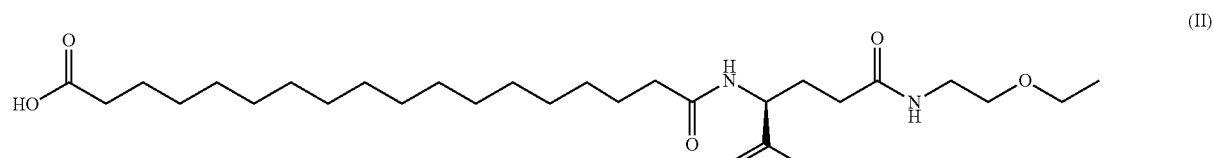

(II)

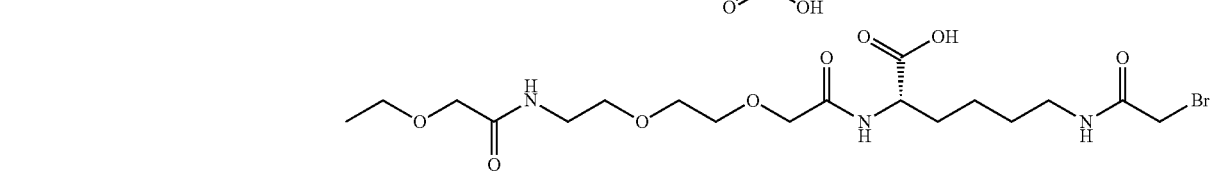

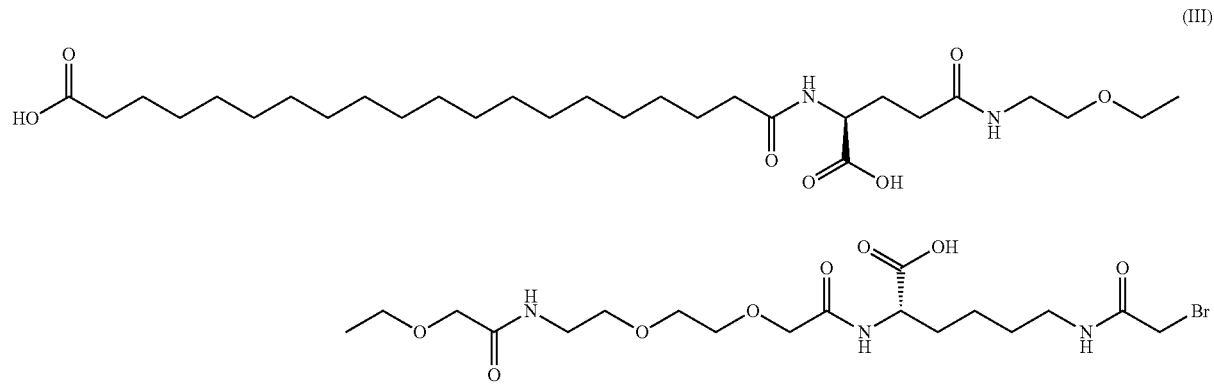

(III)

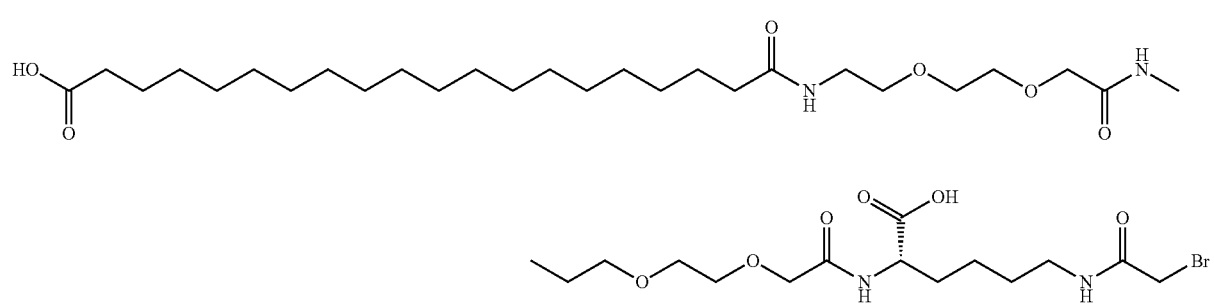

(IV)

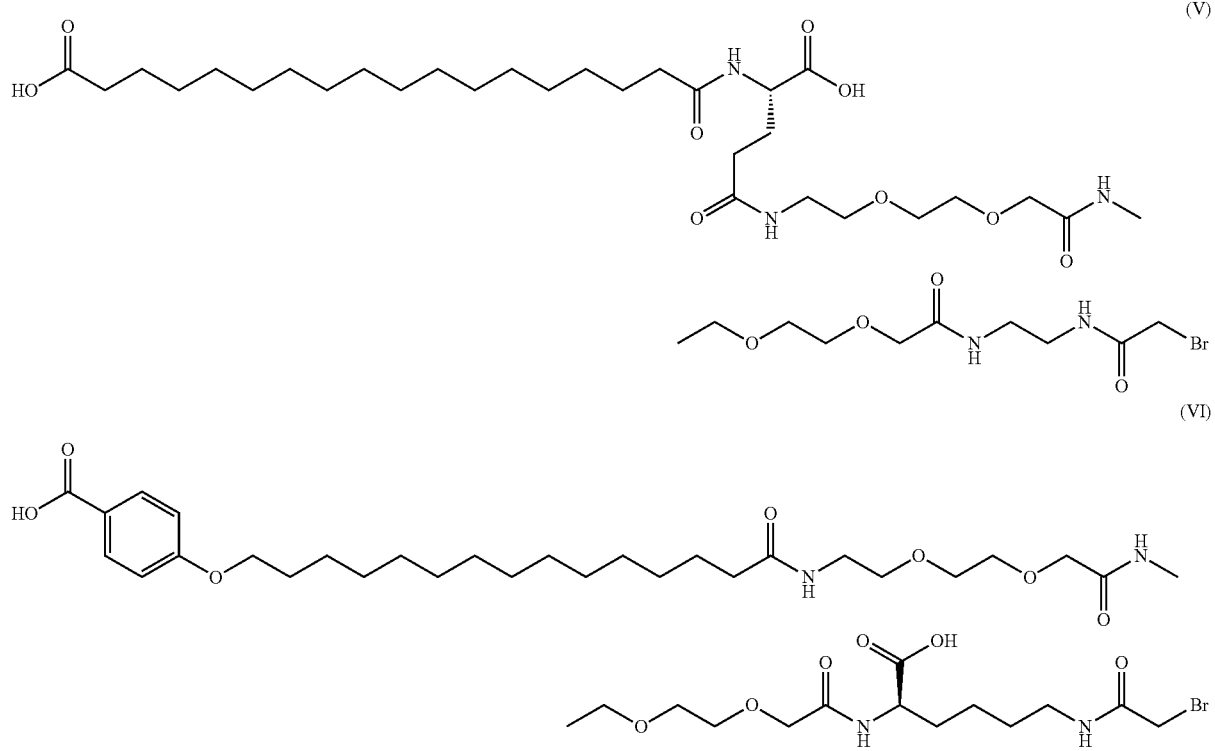

Conjugation of albumin binders I-VI followed the same procedure as described for compound I above. In the case of albumin binders IV and VI, the compounds were not fully soluble before addition to the Fab-solution. In some cases organic solvent was added to facilitate solubilisation. Due to the lower number of acidic groups on albumin binders II-VI, the conjugates did not bind to an AIEX column unless pH was increased to 8.6. In the case of albumin binders II-VI, the pure mono-substituted product was contaminated with varying amounts of multiply modified Fab. These were difficult to remove by ion exchange chromatography.

The identity of all conjugates were confirmed by SDS-page and LC-MS example shown in table 23. The purity was determined to be >90% for conjugates with II, III and V, while conjugates with IV and VI contained approx. 30% of an un-conjugated Fab-based impurity.

TABLE 23

LC-MS data of two different Fab's conjugated to various albumin binders, compared to the calculated mass.

| Conjugate with albumin binder | Compound number | Fab number | m/z found (M + H) | m/z calculated (M + H) |
|---|---|---|---|---|
| II | 0190 | 0120 | 49629 | 49629 |
| III | 0192 | 0120 | 49657 | 49657 |
| IV | 0193 | 0120 | 49427 | 49528 |
| V | 0191 | 0120 | 49543 | 49543 |
| VI | 0194 | 0120 | 49550 | 49550 |
| II | 0243 | 0228 | 48764 | 48765 |
| III | 0240 | 0228 | 48792 | 48793 |
| IV | 0242 | 0228 | 48663 | 48664 |
| V | 0244 | 0228 | 48678 | 48679 |
| I | 0241 | 0228 | 49053 | 49053 |

The above example shows that a variety of different albumin binders can be conjugated to Fab's of both IgG1 and IgG4 origin, in good yield and purity.

The above example shows that a variety of different albumin binders can be conjugated to Fab's of both IgG1 and IgG4 origin, in good yield and purity.

Conjugation of Various Fab's with Albumin Binder I

The following Fab's were conjugated: 0118, 0119, 0127, and 0147 (See table 25). These Fab's contained an unpaired cysteine residue at the C-terminal, or in the case of 0157, close to the C-terminal. The Fab's were derived from IgG1 or IgG4 and correspond to different clones all binding the DR3 receptor. When reacted according to the method described above, conjugates were formed in good yield according to LC-MS data.

The following MS data were obtained (Table 24)

TABLE 24

LC-MS data of various Fab's conjugated with albumin binder I, compared to the calculated mass

| Conjugate with Fab | m/z found (M + H) | m/z calculated (M + H) |
|---|---|---|
| 118 | 49947 | 49947 |
| 119 | 49408 | 49408 |
| 127 | 49712 | 49712 |
| 134 | 49975 | 49975 |
| 147 | 49409 | 49409 |
| 157 | 50169 | 50169 |

The above example shows that a variety of Fab's can be conjugated to different albumin binder molecules in good yield and purity.

TABLE 25

List of anti-DR3 Fab albumin binder conjugates for PK studies.

| Albumin binder structure | Internal Number | Fatty acid Length | Conjugated to Fab | Conjugated compound number |
|---|---|---|---|---|
| (structure) | I | Not applicable | 0120<br>0228<br>0118<br>0119<br>0127<br>0147 | 0153<br>0241<br><br>0189<br><br><br>0166 |
| (structure) | II | C18 | 0120<br>0228 | 0190<br>0243 |
| (structure) | V | C18 | 0120<br>0228 | 0191<br>0244 |
| (structure) | III | C20 | 0120<br>0228 | 0192<br>0240 |
| (structure) | IV | C20 | 0120<br>0228 | 0193<br>0242 |
| (structure) | VI | Not applicable | 0120 | 0194 |

TABLE 25-continued

List of anti-DR3 Fab albumin binder conjugates for PK studies.

| Albumin binder structure | Internal Number | Fatty acid Length | Conjugated to Fab | Conjugated compound number |
|---|---|---|---|---|

A note on nomenclature:
This table uses four-number identification (e.g. 0228). However, different nomenclature can be observed for the same compound. For example compound 0228 is also be named 0227-0000-0228, 0227-0228, 00228, or 228. All these nomenclature denotes the same compound. This rule applies to all compounds.

Example 17

The main objectives have been to characterize the pharmacokinetic parameters after both iv and sc administration to DBA/1 mice, main focus have been on the terminal half-life in order to evaluate the extent of prolongation after modifying the Fab fragment.

Study Design and Methods

Results from two studies are included in the present summary (DKPF111105 and DKPF110703). Both studies were performed in male DBA/1 mice, the mice were dosed either intravenously (i.v.) in the tail vein or subcutaneously (s.c.) in the groin. Dosings were 5 mg/kg for Fab and 1 mg/kg for modified Fab. A sparse sampling design were used, three blood samples were collected at each sampling point, samples were collected from pre-dose up till 7 days after dosing, depending on the compound (e.g. when testing a Fab samples were only collected up to 7 hours after dosing, whereas samples were collected up to 7 days after dosing when testing a conjugated Fab).

The collected plasma samples were all analysed using an ELISA assay, briefly the plates were coated with hDR3-Fc fusion protein (SEQ ID NO:7), diluted blood samples were added and the analyte (Fab or conjugated Fab) would bind to the hDR3, the bound analyte was then detected by a peroxidase labelled anti-Fab antibody, and the absorbance were measure using standard methods. Base on the measured plasma concentration values, the pharmacokinetic parameters were assessed using standard non-compartmental methods, using the commercial available software Phoenix WinNonlin (Pharsight Corp.).

Results

Several different linkers were evaluated to prolong the terminal half-life of the Fab, based on the albumin binding technology it was possible to increase the terminal half-life of the Fab to more than 20 hours for several of the molecules (Table 26). The half-life of the Fab was estimated to be below 1 hour, which illustrates the difference of the Fab compared with a conjugated Fab (Table 26) that all display a much longer half-life.

TABLE 26

Pharmacokinetic parameters after iv of sc administration to mice.

| Study | Route | COMPOUND | NNC | Dose (mg/kg) | T½ (h) | MRT (h) | Cl (mL/h/kg) | F (%) |
|---|---|---|---|---|---|---|---|---|
| DKPF111105 | iv | IgG1 (G1m17) chimeric Fab wt Cys | 0227-0000-0120-1A | 5 | 0.8 | 0.2 | 158 | — |
| DKPF111105 | iv | 0120 with albumin binder linker 0195-0000-3007 C18+ Glu | 0227-0000-0190-1A | 1 | 14 | 17 | 1.7 | — |
| DKPF111105 | iv | 0120 with albumin binder linker 0186-0000-3007 C20+ Glu | 0227-0000-0192-1A | 1 | 21 | 25 | 1.9 | — |
| DKPF111105 | iv | 0120 with albumin binder linker 0195-0000-3007 C20+ Glu | 0227-0000-0193-1A | 1 | 24 | 24 | 3.0 | — |
| DKPF111105 | iv | 0120 with albumin binder linker 0194-0000-3032 (FGF-21 linker) C18+ Glu | 0227-0000-0191-1A | 1 | 16 | 18 | 1.8 | — |
| DKPF111105 | iv | 0120 with albumin binder | 0227-0000-0194-1A | 1 | 7.2 | 9 | 4.3 | — |
| DKPF111105 | sc | IgG1 (G1m17) chimeric Fab wt Cys | 0227-0000-0120-1A | 5 | 1.1 | 2.5 | — | 13 |
| DKPF111105 | sc | 0120 with albumin binder linker 0186-0000-3007 C20+ Glu | 0227-0000-0192-1A | 1 | 27 | 37 | — | 31 |
| DKPF111105 | sc | 0120 with albumin binder linker 0195-0000-3007 C20+ Glu | 0227-0000-0193-1A | 1 | 23 | 32 | — | 34 |
| DKPF111105 | sc | 0120 with albumin binder linker 0194-0000-3032 (FGF-21 linker) C18+Glu | 0227-0000-0191-1A | 1 | 19 | 27 | — | 52 |
| DKPF111105 | sc | 0120 with albumin binder | 0227-0000-0194-1A | 1 | 32 | — | — | 34 |
| DKPF110703 | iv | 0120 with albumin binder | 0227-0000-0153-1A | 1 | 25 | 30 | 1.1 | — |
| DKPF110703 | iv | 0120 wt with Cys to Ser | 0227-0000-0124-2A | 1 | 0.2 | 0.16 | 183 | — |
| DKPF110703 | iv | IgG1 (G1m17) chimeric Fab wt Cys | 0227-0000-0120-1A | 1 | 0.4 | 0.31 | 181 | — |
| DKPF110703 | sc | 0120 with albumin binder | 0227-0000-0153-1A | 1 | 24 | 40 | — | 55 |
| DKPF110703 | sc | 0120 wt with Cys to Ser | 0227-0000-0124-2A | 1 | . | — | — | 16 |
| DKPF110703 | sc | IgG1 (G1m17) chimeric Fab wt Cys | 0227-0000-0120-1A | 1 | . | — | — | 22 |

T½: terminal half-life, MRT: Mean Residence Time, Cl: Clearance, F: Bioavailability

Example 18

Reading Interferon-amma Release as a Way to Determine Anti-Dr3 Activity

Fresh human peripheral blood mononuclear cells (PBMC) were separated from the blood buffy coat (307 Hospital Blood Center of PLA; Beijing, PRC) by centrifugation in Ficoll (GE Healthcare, Cat#17-5442-02) for 20 min at 2000 rpm. After wash in DPBS, the cell pellet was aspirated and resuspended in pre-warmed assay media (RPMI 1640, 10% heat inactivated FBS, 1% penicillin/streptomycin) at $1\times10^6$/ml for overnight culture in flask. Non-adherent lymphocytes were then removed and used in the T cell costimulation assay.

For costimulation assay, recombinant human TL1A (12 µg/mL) was added as a costimulator at 50 µl/well to a dry 96 well U-bottom assay plate (Corning costar 3799) that had been pre-coated, to all wells except the edge, with the primary stimuli, anti-CD3 mAb (BD Pharmingen cat#555336) at 0.3 µg/mL in a 37° C. incubator for 3 hours. The testing anti-DR3 Fabs (0170, 0171, 0173, 0169 & 0118) were transferred in duplicate to the assay plate at 50 pL/well, following an 1:3 serial titration in 96 well deep-well plates (Nunc 278743) for 4× concentrations ranging from 0.012 to 12 µg/mL at 1.5 mL/well. Then the assay plates were added with 0.1 mL of the enriched lymphocytes at $2\times10^5$ cell/well, bringing the final volume to 0.2 mL/well. After 40 hours of cell cultures in 37° C. incubator with 5% $CO_2$, 120 mL supernatants were harvested from each well of the culture plates in order to measure cytokine secretion by IFN-γ ELISA kits (eBioscience Cat#88-7316-88). According to manufacturer's suggestions, the testing supernatants were 1:20 diluted in order to measure the full range of the cytokine been secreted in the T cell assay.

A number of humanized anti-DR3Fabs with (173, 170 &169) or without (171) back mutations was evaluated for their ability to block the TL1A-costimulated cytokine secretion of primary T cells from a healthy donor's peripheral blood.

As shown in Table 27, anti-CD3 priming caused a moderate level (~50 ng/mL) of IFN-γ secretion, which was enhanced more than 3 fold (~159 ng/mL) by recombinant TL1A costimulation; whereas TL1A treatment alone only resulted in a minimal amount of the cytokine release (1.2 ng/mL). Under the TL1A costimulation condition, all testing humanized anti-DR3 Fabs inhibited IFN-γ secretion in dose-dependent and complete manner (IC50~0.01-0.03 ug/mL), with minimal effect on anti-CD3 priming. As the negative control identified from a number of experiments with multiple donors, a non ligand-blocking chimeric anti-DR3Fab 0118 showed no significant effect as expected on TL1A costimulation of T lymphocytes. Similar results were obtained on second batch of 0171 and 0170 Fabs in another experiment with a different blood donor.

Example 19

Anti-DR3 Antibody Fabs Block TL 1A Costimulation of Effector T Cells in Synovial Fluid of Rheumatoid Arthritis Patients Humanized anti-DR3Fabs were shown to inhibit the activity of primary T cells isolated from peripheral blood of healthy individuals in the previous examples. Additionally, some Fab's were also evaluated for their ability to block the effector function of synovial T cells derived from rheumatoid arthritis (RA) patients. Effector functions of T cells include, but are not limited to, IFN-γ secretion which was analyzed in this example. The levels of secreted IFN-γ were measured by the same ELISA kit as described in Example 18.

Fresh human synovial fluid (SF) cells were separated, by centrifugation for 10 min at 2000 rpm, from the knee joint fluid of RA patients as the side product (waste) of intra-articular injection of DMARDs (Beijing University People's Hospital, PRC). The cell pellet was aspirated and resuspended in pre-warmed assay media (RPMI 1640, 10% heat inactivated FBS, 1% penicillin/streptomycin) at $1\times10^6$/mL. A small sample (~$10^5$/0.1 mL) of the synovial cells was examed for the presence (%) of T lymphocyte by FACS analysis. RA/SF cell samples with >5-10% lymphocyte population were used in the T cell costimulation experiments.

For costimulation assay, recombinant human TL1A (12 µg/mL) was added as a costimulator at 50 µl/well to a dry 96 well U-bottom assay plate (Corning costar 3799) that had been pre-coated, to all wells except the edge, with the primary stimuli, anti-CD3 mAb (BD cat#555336) at 0.3 µg/mL in a 37° C. incubator for 3 hours. The testing anti-DR3Fabs (0170, 0171, 0173 & 0118) were transferred in duplicate to the assay plate at 50 µL/well, following an 1:3 serial titration in 96 well deep-well plates (Nunc 278743) for 4× concentrations ranging from 0.012 to 4 µg/mL at 1.5 mL/well. Then the assay plates were added with 0.1 mL of RA/SF cells at $2\times10^5$ cell/well, bringing the final volume to 0.2 mL/well. After 40 hours of cell cultures in 37° C. incubator with 5% $CO_2$, 120 mL supernatants were harvested from each well of the culture plates in order to measure cytokine secretion by IFN-γ ELISA kits (eBioscience Cat#88-7316-88). According to manufacturer's suggestions, the appropriate dilution factor was determined on the testing supernatants in order to measure the full range of the cytokine been secreted in the T cell assay.

Humanized anti-DR3Fab (171) and its backbone-mutated variants (173 & 170) were evaluated for their ability to block the TL1A-costimulated cytokine secretion of synovial T cells from RA patients' knee joints.

As shown in Table 28, anti-CD3 priming induced a moderate level (~1228 pg/mL) of IFN-γ secretion, which was

TABLE 27

Effect of humanized anti-DR3 Fabs on IFN-γ secretion of TL1A-costimulated T lymphocytes from a healthy blood donor

| [µg/mL] | IFN-γ (ng/mL) | | | | |
|---|---|---|---|---|---|
| | cFab-0118 | hFab-0169 | hFab-0170 | hFab-0171 | hFab-0173 |
| 0 | 159 ± 38 | 159 ± 38 | 159 ± 38 | 159 ± 38 | 159 ± 38 |
| 0.003 | 132 ± 0.2 | 121 ± 0.2 | 131 ± 31 | 140 ± 8.2 | 160 ± 3.7 |
| 0.01 | 134 ± 0.3 | 138 ± 34 | 101 ± 64 | 105 ± 58 | 163 ± 0.5 |
| 0.03 | 158 ± 42 | 81 ± 26 | 108 ± 24 | 69 ± 10 | 95 ± 2.8 |
| 0.1 | 151 ± 0.1 | 58 ± 25 | 46 ± 27 | 52 ± 12 | 69 ± 18 |
| 0.3 | 124 ± 68 | 31 ± 0.1 | 51 ± 7.1 | 62 ± 0.3 | 62 ± 11 |
| 1.0 | 132 ± 55 | 55 ± 24 | 63 ± 4.7 | 40 ± 0.4 | 48 ± 3.1 |

The number after ± indicates the standard deviation in the determination.

enhanced about 2 fold (~2188 pg/ml) by recombinant TL1A costimulation; whereas TL1A treatment alone showed no detectable cytokine release. Under the TL1A costimulation condition, three testing humanized anti-DR3Fabs inhibited IFN-γ secretion in dose-dependent and complete manner ($IC_{100}$ ~0.1 ug/mL), with minimal effect on anti-CD3 priming. As the negative control, a non ligand-blocking chimeric anti-DR3Fab 0118 showed no significant effect as expected on TL1A costimulation of T lymphocytes. Similar results were obtained on different batches of 0171 (3 batches) and 0170 (2 batches) Fabs in five experiments with different RASF samples.

TABLE 28

Humanized anti-DR3 Fabs Inhibit TL1A-costimulated IFN-γ secretion of SF cells from a RA patient

| [µg/mL] | IFN-γ (pg/mL) | | | |
|---|---|---|---|---|
| | cFab-0118 | hFab-0170 | hFab-0171 | hFab-0173 |
| 0 | 2188 ± 255 | 2188 ± 255 | 2188 ± 255 | 2188 ± 255 |
| 0.003 | 2308 ± 639 | 1794 ± 366 | 1870 ± 80 | 1552 ± 195 |
| 0.01 | 2280 ± 0.4 | 1635 ± 370 | 1375 ± 248 | 1230 ± 248 |
| 0.03 | 2079 ± 368 | 1357 ± 331 | 1220 ± 0.4 | 1127 ± 122 |
| 0.1 | 2103 ± 0.0 | 1166 ± 0.2 | 1143 ± 65 | 1131 ± 82 |
| 0.3 | 2121 ± 75 | 1301 ± 0.1 | 1157 ± 180 | 992 ± 56 |
| 1 | 2232 ± 567 | 1249 ± 184 | 1232 ± 0.1 | 1062 ± 36 |

Example 20

Epitope Mapping by HX-MS of Anti-DR3Fabs

The HX-MS technology exploits that hydrogen exchange (HX) of a protein can readily be followed by mass spectrometry (MS). By replacing the aqueous solvent containing hydrogen with aqueous solvent containing deuterium, incorporation of a deuterium atom at a given site in a protein will give rise to an increase in mass of 1 Da. This mass increase can be monitored as a function of time by mass spectrometry in quenched samples of the exchange reaction. The deuterium labelling information can be sub-localized to regions in the protein by pepsin digestion under quench conditions and following the mass increase of the resulting peptides.

One use of HX-MS is to probe for sites involved in molecular interactions by identifying regions of reduced hydrogen exchange upon protein-protein complex formation. Usually, binding interfaces will be revealed by marked reductions in hydrogen exchange due to steric exclusion of solvent. Protein-protein complex formation may be detected by HX-MS simply by measuring the total amount of deuterium incorporated in either protein members in the presence and absence of the respective binding partner as a function of time. The HX-MS technique uses the native components, ie protein and antibody or Fab fragment, and is performed in solution. Thus HX-MS provides the possibility for mimicking the in vivo conditions (for a recent review on the HX-MS technology, see Wales and Engen, Mass Spectrom. Rev. 25, 158 (2006)).

Protein Batches Used were:

hDR3: Full extracellular domain oh hDR3 fused to Fc (SEQ ID NO:7). This molecule is dimeric with respect to hDR3 due to the dimerization of the Fc. An expression batch also contains oligomerized version of the protein, but only the purified dimeric fraction was used for HX-MS experiments.

Fab molecules: 0120, 0130, 0143, 0148, 0163, 0228, 0230 and 0231 (see table 29). All proteins were buffer exchanged into PBS pH 7.4 before experiments.

Instrumentation and Data Recording

The HX experiments were performed on a nanoACQUITY UPLC System with HDX Technology (Waters Inc.) coupled to a Synapt G2 mass spectrometer (Waters Inc.). The Waters HDX system contained a Leap robot (H/D-x PAL; Waters Inc.) operated by the LeapShell software (Leap Technologies Inc/Waters Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Waters HDX system furthermore contained a temperature controlled chamber holding the pre-and analytical columns, and the LC tubing and switching valves at 1° C. A separately temperature controlled chamber holds the pepsin column at 25° C. For the inline pepsin digestion, 100 µL quenched sample containing 200 pmol hDR3 was loaded and passed over a Poroszyme® Immobilized Pepsin Cartridge (2.1×30 mm (Applied Biosystems)) placed at 25° C. using a isocratic flow rate of 100 µL/min (0.1% formic acid:$CH_3CN$ 95:5). The resulting peptides were trapped and desalted on a VanGuard pre-column BEH C18 1.7 µm (2.1×5 mm (Waters Inc.)). Subsequently, the valves were switched to place the pre-column inline with the analytical column, UPLC-BEH C18 1.7 µm (1×100 mm (Waters Inc.)), and the peptides separated using a 9 min gradient of 10-40% B delivered at 200 µl/min from the nanoAQUITY UPLC system (Waters Inc.). The mobile phases consisted of A: 0.1% formic acid and B: 0.1% formic acid in $CH_3CN$. The ESI MS data, and the separate elevated energy ($MS^E$) experiments were acquired in positive ion mode using a Synapt G2 mass spectrometer (Waters Inc.). Leucine-enkephalin was used as the lock mass ($[M+H]^+$ion at m/z 556.2771) and data was collected in continuum mode (For further description, see Andersen and Faber, Int. J. Mass Spec., 302, 139-148 (2011)).

Data Analysis

Peptic peptides were identified in separate experiments using standard $MS^E$ methods where the peptides and fragments are further aligned utilizing the ion mobility properties of the Synapt G2 (Waters Inc.). $MS^E$ data were processed using ProteinLynx Global Server version version 2.5 (Waters Inc.). The HX-MS raw data files were processed in the DynamX software (Waters Inc.). DynamX automatically performs the lock mass-correction and deuterium incorporation determination, i.e., centroid determination of deuterated peptides. Furthermore, all peptides were inspected manually to ensure correct peak and deuteration assignment by the software.

Epitope Mapping Experiment

Amide hydrogen/deuterium exchange (HX) was initiated by a 7-fold dilution of hDR3 in the presence or absence of Fabs 0120, 0130, 0143, 0148, 0163, 0228, 0230 or 0231 into the corresponding deuterated buffer (i.e. PBS prepared in $D_2O$, 96% $D_2O$ final, pH 7.4 (uncorrected value)). All HX reactions were carried out at 20° C. and contained 2 µM hDR3 in the absence or presence of 10 µM Fab thus giving a 5 fold molar excess of Fab. At appropriate time intervals ranging from 10 sec to 3000 sec, 50 µl aliquots of the HX reaction were quenched by 50 µl ice-cold quenching buffer (1.35M TCEP) resulting in a final pH of 2.5 (uncorrected value).

Results and Discussion

The HX time-course of 20 peptic peptides, covering 75% of the primary structure of hDR3 extracellular domain were monitored in the absence or presence of 0120, 0130, 0143, 0148, 0163, 0228, 0230 or 0231 Fab for 10 to 3000 sec. hDR3 contains two N-glycosylation sites at positions N67 and N106 and the peptide map thus has gaps in these regions.

The observed exchange pattern in the early time points (<300 sec) in the presence or absence of Fabs 0120, 0130, 0143, 0148, 0163, 0228, 0230 or 0231 can be divided into two different groups: One group of peptides display an exchange pattern that is unaffected by the binding of Fabs. In contrast, another group of peptides in hDR3 show protection from exchange upon Fab binding (table 29). Observed exchange protection in a peptide is indicative of this region being involved in Fab binding. Thus the epitope is partly or maybe even fully located within the region defined by the specific peptides. However, since the resolution of HX-MS is based on peptic peptide, exchange protection within a given region does not means that every residue within the region necessarily is involved in Fab binding.

Epitope Mapping of 0148 and 0163

Fabs 0148 and 0163 represent Fab molecules that bind hDR3 but do not block TL1A binding. These Fab molecules were included in the study for control. Epitope signal was observed in region P140-L153 in CRD3 for Fab 0148 (table 29). The current experiment was performed with 5x surplus of Fab, however HX-MS experiments using equimolar rations of 0148 to hDR3 confirms that this Fab can be mapped under standard equimolar conditions.

Weak epitope signal for Fab 0163 was observed partly in region G163-F169 and partly in region Y170-L184 in the CRD4 region.

Epitope Mapping of 0120, 0130, 0143 and 0228

Fab 0228 was mapped in several experiments using 3-5x surplus of Fab molecule. Epitope signal was observed in regions R32-G54, G37-L45 and F46-A59 in CRD1. However, based on the relative level of exchange protection in the peptic peptides and the weak or absent exchange protection in region F46-Y56, it is concluded that the epitope for 0228 is strongest in region G37-L45 and L57-A59. The region G37-L45 also covers the residues found by mutagenesis to be important for 0228/0123 binding to hDR3 and the data from these experiments are thus in full accordance (Example 12, Table 16). Surprisingly, it was necessary to use a large surplus of 0228 Fab relative to hDR3. Normally, it is sufficient to use equimolar ratio of mAb or Fab when performing epitope mapping by HX-MS. If using equimolar ration of 0228 to hDR3, no epitope signal was observed (data not shown) even though 0228 has a very high affinity (Example 11, table 14). These observations points towards the 0228 epitop being in a region that is not fully solvent accessible under the experimental conditions. Thus the low exchange protection in spite of a high affinity of 0228 could be a result of the fab molecule having to either appear on top of—or compete with—hDR3 self-interactions. The hDR3 self-interaction may be a consequence of unspecific aggregation or a consequence of clustering of the extracellular domain as for example described for other members of the TNFR super-family (Mukai et al. (2010) Sci. Signal.3, ra83). Furthermore, weak effects could be observed in the C-terminal region. Since 0228 and 0120 have full affinity when binding to a protein containing only CRD1 (Example 11, table 14), the C-terminal effects is most likely a result of conformational rearrangements upon Fab binding and may be a result of movements in the hinge region fusing DR3 to Fc.

From SPR experiments it has been established that 0120, 0130 and 0143 all compete with 0228 and with each other for binding to hDR3 (Example 11, Table 15). Thus, these Fabs share epitopes either partly or fully.

In agreement, HX-MS on these Fabs also reveal epitope signal in the same region G37-L45. However the exchange protection magnitude is weaker. Based on the observations above it can be speculated that in order to have HX-MS reveal exchange protection in a clustering interface it is needed to have high surplus of the binding molecule and it should be a high affinity interaction.

Epitope Mapping of 0230 and 0231

Epitope mapping on Fab 0230 and 0231 (11H08 from WO2011106707) did not reveal any epitope. Given the observations described above that epitope mapping on hDR3 need a good affinity in order to be successful it can be speculated that the relatively poorer affinity of these Fabs (WO2011106707) preclude successful epitope mapping by HX-MS.

TABLE 29

HXMS analysis of DR3 yielding epitope information for Fab molecules. After deuterium exchange reaction. DR3 is digested with pepsin yielding the following peptic peptide regions that were analyzed. Positions N67 and N106 are glycosylated and the peptide map thus has gaps in these regions. Numbering of DR3 residues follows SEQ ID NO: 1.

| Sequence | Region | 0120 blocking | 0130 blocking | 0143 blocking | 0148 non-blocking | 0163 non-blocking | 0228 blocking |
|---|---|---|---|---|---|---|---|
| R32-G54 | CRD1 | EX | NA | NA | N | NA | EX |
| G37-L45 | CRD1 | W | W | W | N | N | EX |
| F46-Y56 | CRD1 | W/N | N | N | N | N | W/N |
| F46-A59 | CRD1 | EX/W | N | NA | N | N | EX |
| L71-F78 | CRD2 | N | N | N | N | N | N |
| L71-L79 | CRD2 | N | N | N | N | N | N |
| L79-E88 | CRD2 | N | N | N | N | N | N |
| L79-C89 | CRD2 | N | N | N | N | N | N |
| A80-C89 | CRD2 | N | N | N | N | N | N |
| V110-W121 | CRD2/CRD3 | N | N | N | N | N | N |
| V110-F122 | CRD2/CRD3 | N | N | N | N | N | N |
| V123-C130 | CRD3 | NA | N | N | N | N | N |
| V131-L142 | CRD3 | N | NA | N | N | N | N |
| P140-L153 | CRD3 | N | N | N | EX | N | N |
| D143-L153 | CRD3 | N | N | N | EX | N | N |
| L154-L166 | CRD3/CRD4 | N | N | N | N | N | N |
| L154-F169 | CRD3/CRD4 | N | N | N | N | W | N |
| G163-F169 | CRD4 | N | N | N | N | W | N |

TABLE 29-continued

HXMS analysis of DR3 yielding epitope information for Fab molecules. After deuterium exchange reaction. DR3 is digested with pepsin yielding the following peptic peptide regions that were analyzed. Positions N67 and N106 are glycosylated and the peptide map thus has gaps in these regions. Numbering of DR3 residues follows SEQ ID NO: 1.

| Sequence | Region | 0120 blocking | 0130 blocking | 0143 blocking | 0148 non-blocking | 0163 non-blocking | 0228 blocking |
|---|---|---|---|---|---|---|---|
| Y170-L184 | CRD4 | N/W | N | N | N | W | N/W |
| Y170-A193 | CRD4 | N/W | N | N | N | W | N/W |

EX: exchange protection upon Fab binding indicating epitope region (>0.4 Da).
W: Weak exchange protection upon Fab binding (0.2-0.4 Da).
N: No exchange protection upon Fab binding (<0.2 Da).
NA: Not analyzable in respective experiment.

More than one assignment indicates that two or more experiments have given slightly different results regarding magnitude of exchange protection.

Example 21

Overview of Antibodies Mentioned Herein

Table 30 provides and overview of antibodies mentioned herein and the naming of them dependent on the different mAb/Fab formats used. A note on nomenclature: Table 30 uses four-number identification (e.g. 0228). However, different nomenclature can be observed for the same compound. For example compound 0228 is also be named 0227-0000-0228, 0227-0228, 00228 or 228. All these nomenclature denotes the same compound. This rule applies to all compounds.

TABLE 30

List of anti-DR3 mAb and Fab compounds selected for studies. This table gives the correlation between mAb, Fab and hydridoma clone numbering. Compounds in the same row have the same CDR regions and originate from the same murine mAb, but have been prepared in different formats. Compound in the same column share the same molecular format, e.g. species or isotype of the compound, but have been prepared from different murine mAbs.

| Hybridoma number | hybridoma purified murine mAb | recombinant murine mAb | Fab from papain cleaved murine mAb | Recombinant murine Fab | Chimeric Fab. Murine variable domain, human IgG1 constant domain. | Chimeric Fab. Murine variable domain, human IgG4 constant domain. |
|---|---|---|---|---|---|---|
| 5F13 | 0025 | 0121 | | 0140 | 0147 | 0149 |
| 27F16 or 27F16A1 | 0070 or 0083 | 0106 | | 0110 | 0118 | 0125 |
| 27F38 | 0071 | | | | | |
| 27F44 or 27F44A2 | 0072 or 0084 | 0107 | 0087 | 0111 | 0119 | 0126 |
| 28F26 or 28F26A3 | 0073 or 0085 | 0108 | 0088 | 0112 | 0120 | 0127 |
| 28F69 | 0074 | | | | | |
| 29F6 | 0075 | | | | | |
| 29F8 | 0076 or 0086 | 0116 | 0089 | | | |
| 30F1 | 0077 | | 0091 | | | |
| 44F434 | | | | 0128 | | |
| 44F478 | | | | 0129 | | |
| 45F36 | | | | 0130 | | |
| 45F187 | | | | | | |
| 45F243 | | | | | | |
| 45F284 | | | | 0131 | | |
| 45F304 | | | | 0132 | | |
| 46F108 | | | | | | |
| 46F147 or 46F42 | | | | | 0136 | |
| | | | | | 0135 | |
| 46F164 | | | | | 0137 | |
| 46F172 | | | | | 0138 | |
| 46F186 | | | | | 0139 | |
| 48F312 | | | | | | |
| 49F23 | | | | | | |
| 50F1 | | | | | | |
| 50F3 | | | | | | |
| 50F62 | | | | | | |
| 50F134 | | | | | | |
| 50F141 | | | | | | |
| 50F142 | | | | | | |
| 50F189 | | | | | | |
| 50F191 | | | | | | |
| 50F213 | | | | | | |
| 11H08 | | | | | | |

TABLE 30-continued

List of anti-DR3 mAb and Fab compounds selected for studies. This table gives the correlation between mAb, Fab and hydridoma clone numbering. Compounds in the same row have the same CDR regions and originate from the same murine mAb, but have been prepared in different formats. Compound in the same column share the same molecular format, e.g. species or isotype of the compound, but have been prepared from different murine mAbs.

(WO2011106707)
aTNP

| Hybridoma number | Chimeric Fab. Murine variable domain, human IgG4 constant domain. Hinge Cys -> Ser | Humanized Fab, IgG4 | Humanized Fab, IgG1 | blocking TL1A binding | SEQ ID NO |
|---|---|---|---|---|---|
| 5F13 | 0148 | | | No | 24, 25 |
| 27F16 or 27F16A1 | 0122 | | | partially | 8, 9 |
| 27F38 | | | | no | |
| 27F44 or 27F44A2 | 0123 | 0227, 0228 (S49A HC), 0229 (S49A HC, S60A LC) | 0169, 0170, 0171, 0172, 0173, 0174, 0222, 0219 (S49A HC), 0226 (S49A HC, S60A LC) | yes | 10, 11, 16, 17 |
| 28F26 or 28F26A3 | 0124 | | | yes | 12, 13 |
| 28F69 | | | | no | |
| 29F6 | | | | no | |
| 29F8 | | | | yes | |
| 30F1 | | | | no | |
| 44F434 | 0143 | | | yes | 20, 21 |
| 44F478 | 0144 | | | partially | |
| 45F36 | | | | yes | 18, 19 |
| 45F187 | 0150 or 0163 | | | no | 26, 27 |
| 45F243 | 0184 or 0185 | | | yes | |
| 45F284 | 0145 | | | partially | |
| 45F304 | 0146 | | | no | |
| 46F108 | | | | yes | |
| 46F147 or 46F42 | 0151 | | | yes | |
| 46F164 | | | | partially | |
| 46F172 | | | | partially | |
| 46F186 | | | | yes | |
| 48F312 | 0179 | | | no | |
| 49F23 | 0180 | | | partially | |
| 50F1 | 0159 | | | yes | |
| 50F3 | 0177 | | | yes | |
| 50F62 | 0186 | | | yes | |
| 50F134 | 0160 | | | yes | |
| 50F141 | 0161 | | | partially | |
| 50F142 | 0162 | | | yes | |
| 50F189 | 0178 | | | yes | |
| 50F191 | 0152 | | | yes | 22, 23 |
| 50F213 | 0187 | | | yes | |
| 11H08 (WO2011106707) | | 0230 (H1L2) 0231 (H1L4) | | yes | 14, 15 |
| aTNP | 0158* | | | isotype control, does not bind DR3 | |

*Isotype control - not DR3 binding

Example 22

Binding Experiment

Material and Methods: Buffy Coats were obtained from normal healthy volunteers from Copenhagen Hospital. CD4+ T cells were isolated through magnetic bead separation. Cells were activated with 2 ng/ml IL-12, 50 ng/ml IL-18 and 100 ng/ml TL1A (Flag-HIS-TEV-TL1A-produced at Novo Nordisk A/S) and cultured for 5 days. On day 5 cells were stained with 10, 5, 1, 0.5, 0.1 or 0.0001 µg/ml of the anti-DR3 mAb clones 0072, 0073, or 0077, or with Fab fragment clones 0087, 0088 or 0091. A secondary PE conjugated goat-anti-mouse (H+L) was used for detection. Samples were in duplicate. Staining intensity was evaluated by FACS.

Results: No binding to the cells could be detected for the monoclonal IgG clone 0077, and its corresponding Fab clone 0091. The monoclonal IgG clones 0072 and 0073 showed potent binding to cytokine activated CD4+ T cells with maximal binding observed at concentrations of 1 ug/ml or lower. The corresponding Fab clones (0087 and 0088) bound with similar potency to cytokine activated cells, although slightly lower MFI values were recorded at binding saturation. The greater observed MFI values of full-length antibody treated compared with Fab treated cells was expected since the secondary (detecting) antibody (anti-IgG heavy and light chain) bound to both Fab and Fc parts of the full-length IgG antibody clones, but only to Fab parts of Fab clones (Table 31).

TABLE 31

Mean fluorescence intensity (MFI) values are shown for IL-12/IL-18/TL1A activated cells on day 5. Cells are gated on singlets, live and CD4+ T cells.

| Antibodies or Fab fragments | Concentration used in assay | MFI |
| --- | --- | --- |
| 0072 | 1 µg/ml | 1300b |
| 0073 | 1 µg/ml | 1300 |
| 0077 | 1 µg/ml | 100 |
| 0087 | 1 µg/ml | 500 |
| 0088 | 1 µg/ml | 500 |
| 0091 | 1 µg/ml | 100 |

Example 23

T Cell Proliferation

CD4+ T cells were isolated from Buffy Coats through magnetic bead separation using CD4 Rosettesep (Stem cell technologies) and Histopaque (Sigma). T cells ($2*10^5$ cells/well in a 96-well plate) were activated for 5 days with 2 ng/ml IL-12, 50 ng/ml IL-18 and 100 ng/ml TL1A (Flag-HIS-TEV-TL1A; Novo Nordisk) with and without anti-TL1A (1000 ng/ml; MAB7441; RnDSystems) or DR3 mAbs or DR3Fabs (5 or 10 µg/ml) The DR3 mAbs used were 0072, 0073 and 0077. The DR3Fabs used were 0087, 0088 and 0091. All samples were done in triplicate. Cell proliferation was measured by thymidine incorporation. Cells were pulsed with [$^3$H]thymidine after 5 days of activation and harvested 16 h later. The incorporated thymidine was detected as counts pr minute (cpm) by a Top Counter.

Results: T cell proliferation was increased 3-fold by costimulation with TL1A. This TL1A-dependent increase was blocked by co-incubation with the anti-TL1A neutralizing control antibody. All anti-DR3 mAbs as well as the Fab 0091 slightly inhibited proliferation at 10 µg/ml, while the Fabs 0087 and 0088 completely blocked proliferation even with the lowest concentration used in the assay. In conclusion, Fabs 0087 and 0088 are very efficient in downregulating the TL1A-dependent co-stimulation of CD4-positive T-cell proliferation.

In a similar experiment IL-12 (2 ng/ml), IL-18 (50 ng/ml) and 100 ng/ml TL1A (Flag-His-TEV-TL1A; Novo Nordisk). treated CD4+ T cells demonstrated 6-fold increased T cell proliferation compared to IL-12/IL-18 treated T cells. The 0123 and 0124 Fabs totally blocked the induced T cell proliferation already at a concentration of 0.16 µg/ml of the Fab while the corresponding mAb 0072 and 0108 did not affect T cell proliferation. In Table 2 data for the pair of mAb 0072 and the corresponding Fab 0123 is shown. Proliferation detected by thymidine incoporation is given as counts pr minute (cpm).

TABLE 32

| Treatment | mAb 0072 | Fab 0123 |
| --- | --- | --- |
| IL-12/IL-18 | 1629 ± 109 cpm | 1629 ± 109 cpm |
| IL-12/IL-18+TL1A | 10439 ± 689 cpm | 10439 ± 689 cpm |
| IL-12-IL-18+TL1A+0.00128 µg/ml mAb or Fab | 10434 ± 1132 cpm | 5492 ± 1330 cpm |
| IL-12/IL-18+TL1A+0.16 µg/ml mAb or Fab | 11886 ± 984 cpm | 2329 ± 336 cpm |
| IL-12/IL-18+TL1A+10 µg/ml mAb or Fab | 10139 ± 689 cpm | 1619 ± 109 cpm |

The standard deviation is indicated by the number after the ±.

Cytokine Release Affected by Anti-DR3Fabs

CD4+ T cells isolated from Buffy Coats through magnetic bead separation using CD4 Rosettesep (Stem cell technologies) and Histopaque(Sigma) were stimulated in the absence of TCR activation, with cytokines IL-12 (2 ng/ml), IL-18 (50 ng/ml) with and without 100 ng/ml TL1A (Flag-His-TEV-TL1A; Novo Nordisk). Supernatants from activated CD4+ T cells ($2\times10^5$ cells/well) were harvested after 48 h and analysed for cytokine release by Bioplex.

The released cytokines IL-6, IFNγ, GM-CSF and TNFα were all induced after 48 hours by TL1A by the IL-12/IL-18 treated CD4+ T cells. IL-6, IFNγ, GM-CSF, TNFα were induced 16-fold (p=0.05), 1.2 (p=0.02), 7.5-fold (p=0.04), 4.4 (p=0.0007) by TL1A, compared to IL-12/IL-18 activated cells. IL-6 (p=0.04), GM-CSF (p=0.04) and TNFα (p=0.0008) were all significantly blocked by the anti-DR3Fab 0124, when compared to the DR3 binding non-blocking Fab 0091 (Table 33).

TABLE 33

| Cytokines (mean +/− SEM) | IL-12/IL-18-activated CD4+ T cells (mean ± SEM) | IL-12/IL-18-activated CD4+ T cells + TL1A (mean ± SEM) | IL-12/IL-18-activated CD4+ T cells + TL1A+0124 (mean ± SEM) | IL-12/IL-18-activated CD4+ T cells + TL1A+0091 (mean ± SEM) |
| --- | --- | --- | --- | --- |
| IL-6 | 361 ± 145 | 5981 ± 1918 | 698 ± 282 | 9268 ± 3564 |
| IFNγ | 4207 ± 270 | 4893 ± 400 | 4388 ± 195 | 4945 ± 516 |
| GM-CSF | 45 ± 11 | 336 ± 101 | 55 ± 17 | 437 ± 167 |
| TNFα | 23 ± 2.3 | 102 ± 3 | 24 ± 2.5 | 121 ± 21 |

The standard deviation is indicated by the number after the ± .

Example 24

Functional Studies Using Lamina Propria Mononuclear Cells Isolated from Intestinal Biopsies from Crohn's Patients Lamina Propria Mononuclear Cells (LPMCs) isolated from intestinal biopsies from Crohn's patients versus non-IBD controls were activated with IL-12 (2 ng/ml), IL-18 (50 ng/ml) and 100 ng/ml TL1A (Flag-His-TEV-TL1A; Novo Nordisk) with and without anti-DR3Fab 0124 and the non-blocking control 0091.

LPMCs from inflamed Crohn's patients were able to respond to IL-12/IL-18+ TL1A by inducing IFNγ and the TL1A-induced level of IFNγ was significantly blocked by 0124 (p=0.0001, n=4), Table 34. The DR3Fabs 0124 and 0228 furthermore inhibit GM-CSF, TNF-a, and IFNg secretion by IL-12/IL-18 stimulated TL1A treated LPMCs from Crohn's patients.

TABLE 34

| Cytokines (mean +/− SEM) | IL-12/IL-18-activated LPMCs (mean ± SEM, n = 4)) | IL-12/IL-18-activated LPMCs + TL1A (mean ± SEM, n = 4) | IL-12/IL-18-activated LPMCs + TL1A+0124 (mean ± SEM, n = 4) |
|---|---|---|---|
| IFNγ | 195 ± 51 | 577 ± 158 | 199 ± 53 |

The invention claimed is:

1. An isolated monovalent antagonistic anti-DR3 antibody, the antibody comprising a heavy chain variable region comprising a heavy chain CDR1, a heavy chain CDR2, and a heavy chain CDR3 and a light chain variable region comprising a light chain CDR1, a light chain CDR2, and a light chain CDR3, the heavy chain CDR1 comprising an amino acid sequence corresponding to Kabat residues 31-35 of SEQ ID NO:10; the heavy chain CDR2 comprising an amino acid sequence corresponding to Kabat residues 50-58 of SEQ ID NO:10; the heavy chain CDR3 comprising an amino acid sequence corresponding to Kabat residues 95-102 of SEQ ID NO:10; the light chain CDR1 comprising an amino acid sequence corresponding to Kabat residues 24-34 of SEQ ID NO:11; the light chain CDR2 comprising an amino acid sequence corresponding to Kabat residues 50-56 of SEQ ID NO:11; and the light chain CDR3 comprising an amino acid sequence corresponding to Kabat residues 89-97 of SEQ ID NO:11.

2. The isolated monovalent antagonistic anti-DR3 antibody of claim 1, wherein the heavy chain variable region comprises an amino acid sequence that is at least 90% identical to SEQ ID NO:10, and wherein the light chain variable region comprises an amino acid sequence that is at least 90% identical to SEQ ID NO:11.

3. The isolated monovalent antagonistic anti-DR3 antibody of claim 2, wherein the heavy chain variable region comprises an amino acid sequence of SEQ ID NO:10, and wherein the light chain variable region comprises an amino acid sequence of SEQ ID NO:11.

4. The isolated monovalent antagonistic anti-DR3 antibody of claim 1, wherein the monovalent antibody is conjugated to a lipophilic moiety.

5. The isolated monovalent antagonistic anti-DR3 antibody of claim 4, wherein the lipophilic moiety comprises a —(CH$_2$)$_n$—CO— fatty acyl group, and wherein n is 16-18.

6. The isolated monovalent antagonistic anti-DR3 antibody of claim 4, wherein the lipophilic moiety comprising a —(CH$_2$)$_n$—CO— fatty acyl group, and wherein n is 15.

7. The isolated monovalent antagonistic anti-DR3 antibody of claim 4, wherein said antibody is conjugated to a lipophilic moiety selected from the group consisting of formulas (I), (II), (III), (IV), (V), and (VI):

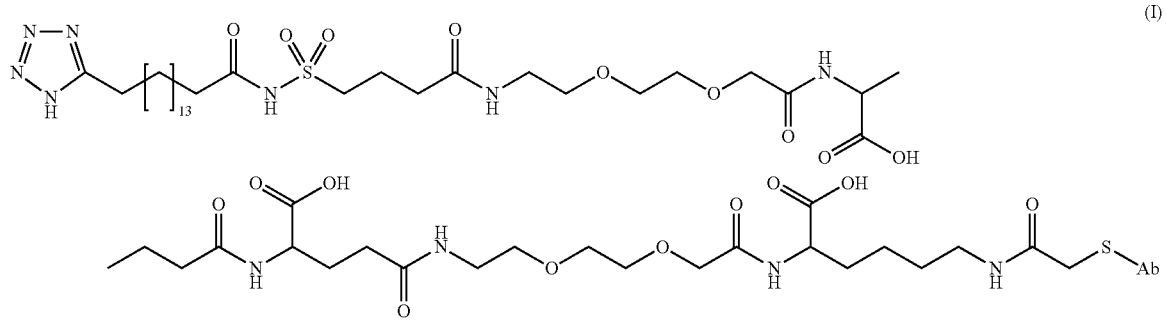

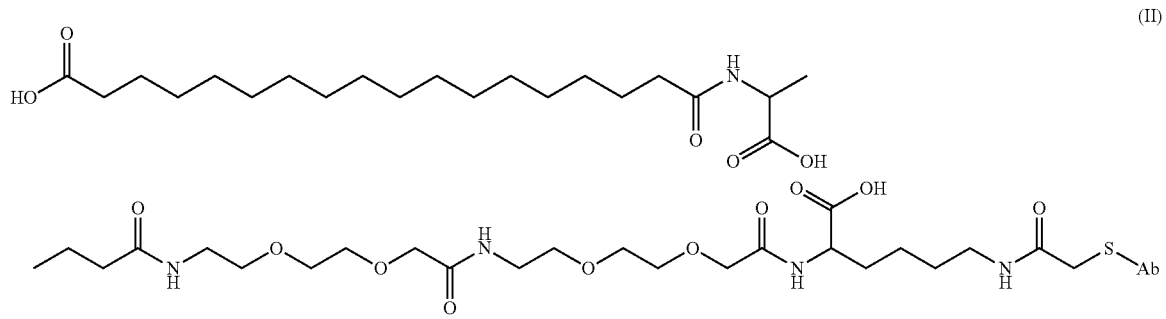

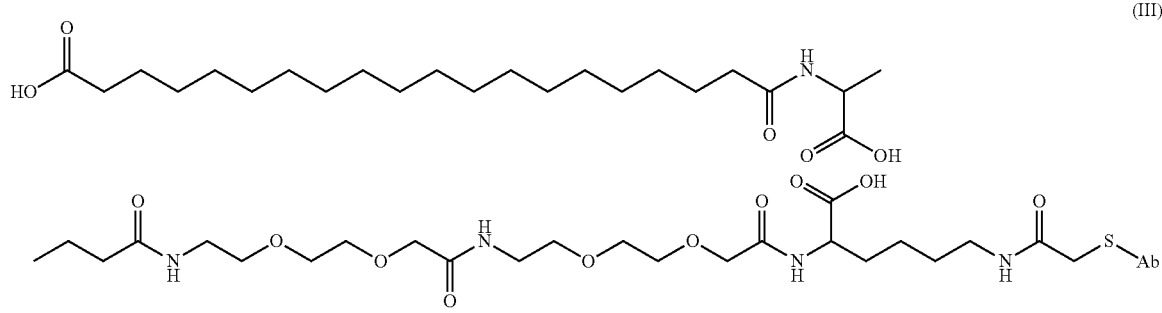

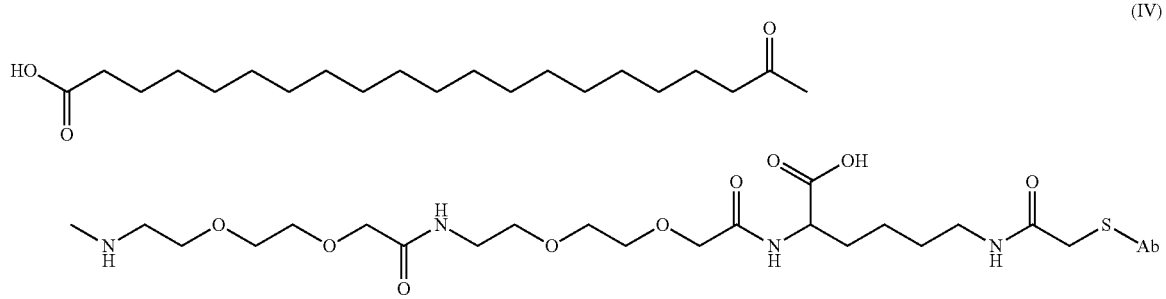

-continued

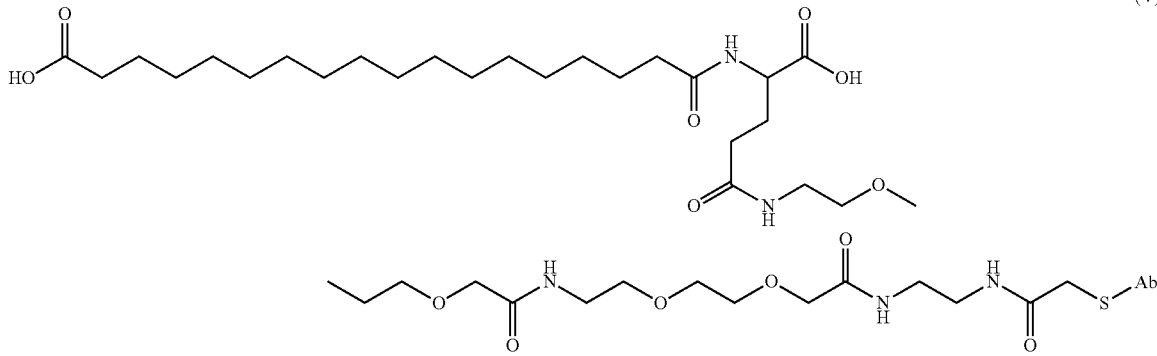

(V)

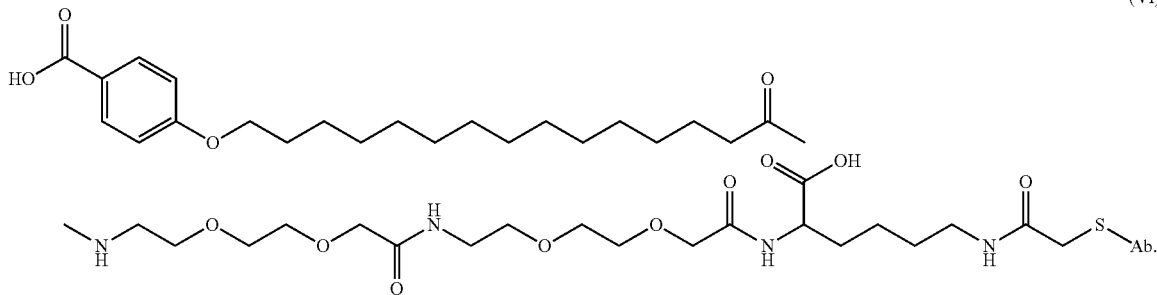

(VI)

8. The isolated monovalent antagonistic anti-DR3 antibody of claim 4 further comprising a heavy chain constant region, wherein the lipophilic moiety is attached to a cysteine amino acid residue of the heavy chain constant region corresponding to Kabat residue 239 via a hydrophilic spacer.

9. The isolated monovalent antagonistic anti-DR3 antibody of claim 3, further comprising a heavy chain constant region, wherein the monovalent antibody is conjugated to a lipophilic moiety having the formula (I)

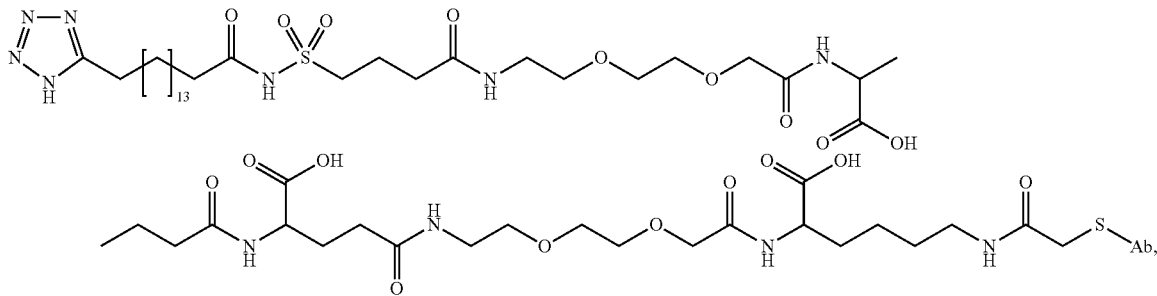

and wherein the lipophilic moiety is attached to a cysteine amino acid residue of the heavy chain constant region corresponding to Kabat residue 239 via a hydrophilic spacer.

10. The isolated monovalent antagonistic anti-DR3 antibody of claim 1, wherein the antibody is a Fab fragment.

11. The isolated monovalent antagonistic anti-DR3 antibody of claim 9, wherein the antibody is a Fab fragment.

12. The isolated monovalent antagonistic anti-DR3 antibody of claim 1, wherein the antibody is an IgG4 type antibody.

13. A pharmaceutical composition comprising a monovalent antagonistic anti-DR3 antibody and a pharmaceutically acceptable excipient, the monovalent antagonistic anti-DR3 antibody comprising a heavy chain CDR1 comprising an amino acid sequence corresponding to Kabat residues 31-35B of SEQ ID NO:10; a heavy chain CDR2 comprising an amino acid sequence corresponding to Kabat residues 50-58 of SEQ ID NO:10; a heavy chain CDR3 comprising an amino acid sequence corresponding to Kabat residues 95-102 of SEQ ID NO:10; a light chain CDR1 comprising an amino acid sequence corresponding to Kabat residues 24-34 of SEQ ID NO:11; a light chain CDR2 comprising an amino acid sequence corresponding to Kabat residues 50-56 of SEQ ID NO:11; and a light chain CDR3 comprising an amino acid sequence corresponding to Kabat residues 89-97 of SEQ ID NO:11.

14. The pharmaceutical composition of claim 13, wherein the monovalent antagonistic anti-DR3 antibody comprises a heavy chain comprising an amino acid sequence of SEQ ID NO:10 and a light chain comprising an amino acid sequence of SEQ ID NO:11; and wherein the monovalent antagonistic DR3 antibody is conjugated to a lipophilic moiety having the formula

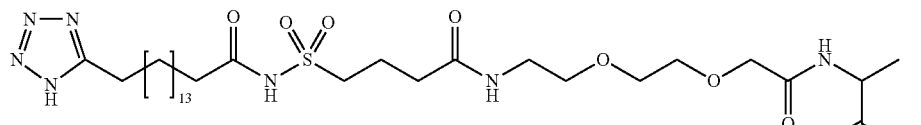

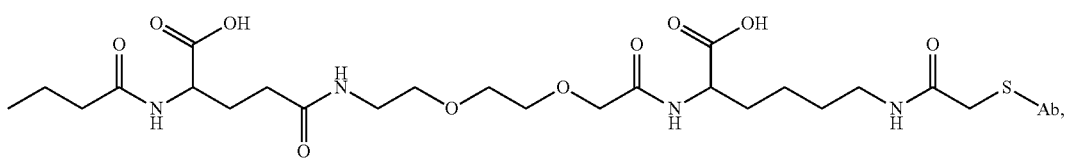

and wherein the lipophilic moiety is attached to a cysteine amino acid residue of the heavy chain corresponding to Kabat residue 239 via a hydrophilic spacer.

15. The pharmaceutical composition of claim 14, wherein the monovalent antagonistic anti-DR3antibody is a Fab.

16. The isolated monovalent antagonistic anti-DR3 antibody of claim 1, wherein the heavy chain variable region comprises an amino acid sequence that is at least 90% identical to SEQ ID NO:16, and wherein the light chain variable region comprises an amino acid sequence that is at least 90% identical to SEQ ID NO:17.

17. The isolated monovalent antagonistic anti-DR3 antibody of claim 16, wherein the heavy chain variable region comprises an amino acid sequence of SEQ ID NO:16, and wherein the light chain variable region comprises an amino acid sequence of SEQ ID NO:17.

18. The isolated monovalent antagonistic anti-DR3 antibody of claim 17, wherein the monovalent antibody is conjugated to a lipophilic moiety.

19. The isolated monovalent antagonistic anti-DR3antibody of claim 18, wherein the lipophilic moiety comprises a —(CH$_2$)$_n$—CO— fatty acyl group, and wherein n is 16-18.

20. The isolated monovalent antagonistic anti-DR3antibody of claim 18, wherein said antibody is conjugated to a lipophilic moiety selected from the group consisting of formulas (I), (II), (III), (IV), (V), and (VI):

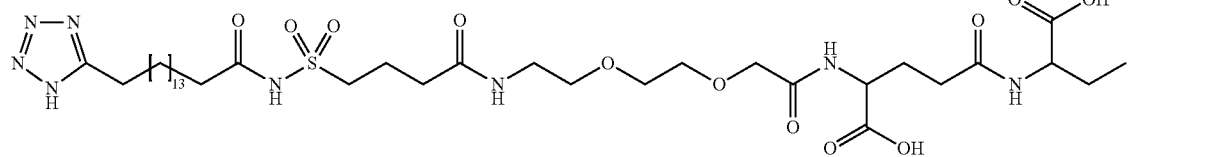

(I)

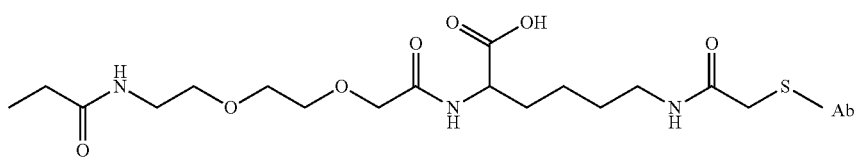

(II)

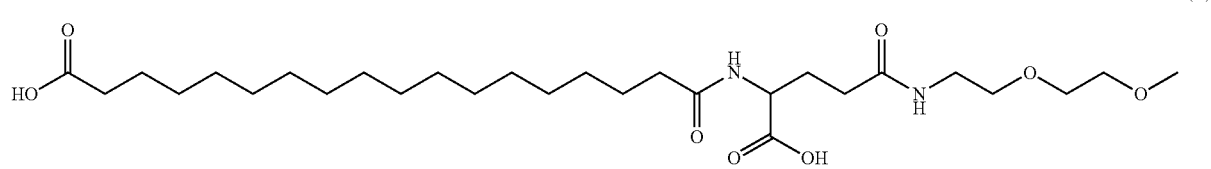

(III)

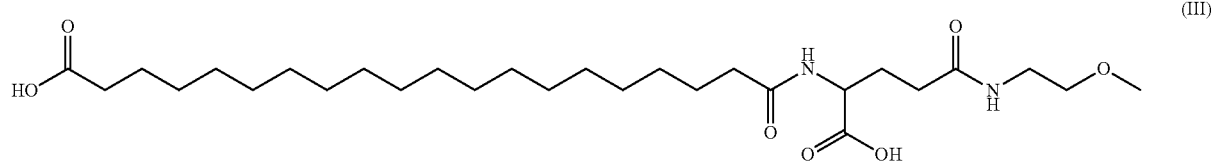

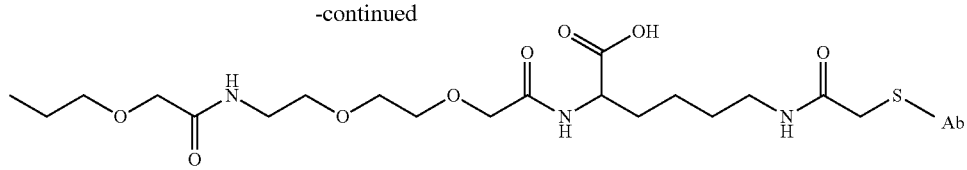

(IV)

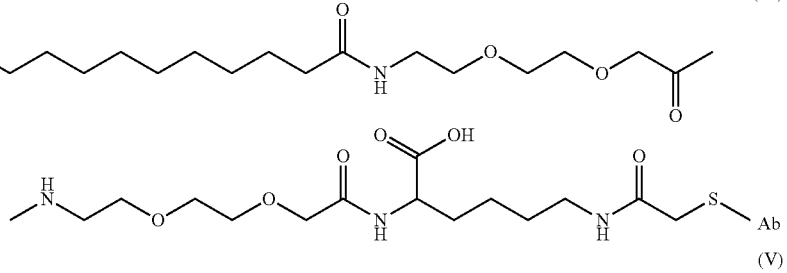

(V)

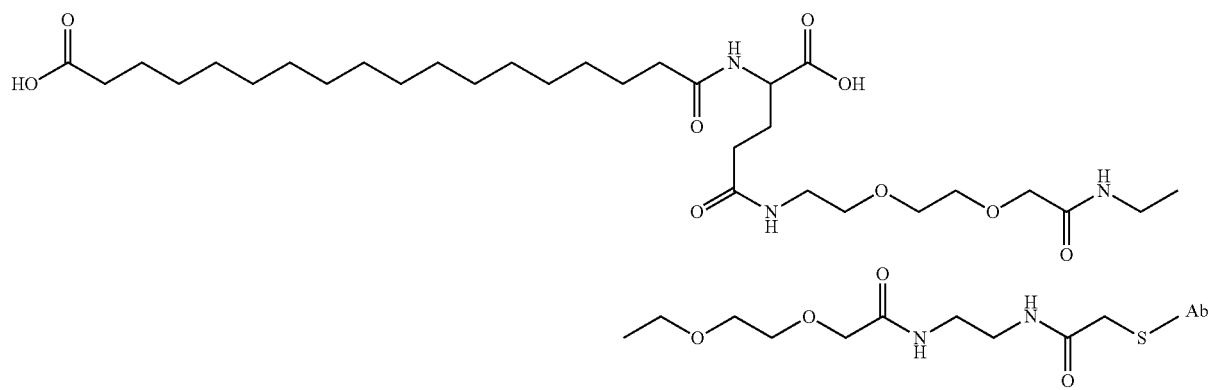

(VI)

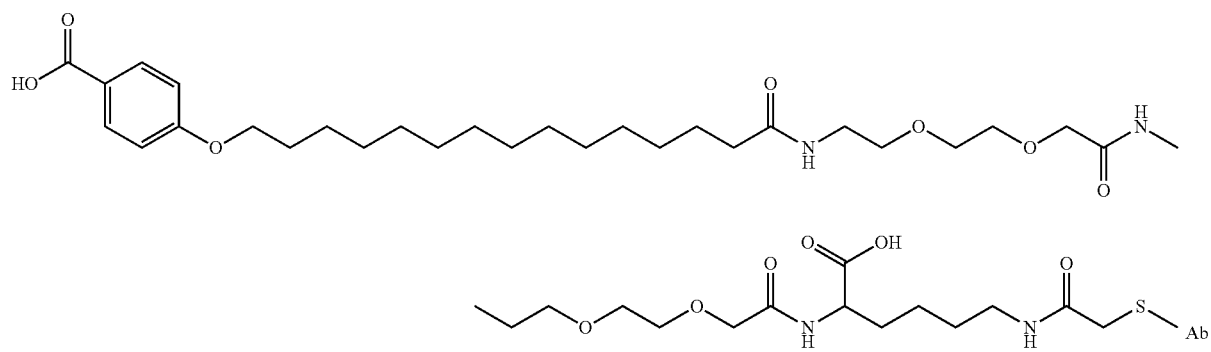

21. The isolated monovalent antagonistic anti-DR3antibody of claim 18 further comprising a heavy chain constant region, wherein the lipophilic moiety is attached to a cysteine amino acid residue of the heavy chain constant region corresponding to Kabat residue 239 via a hydrophilic spacer.

22. The isolated monovalent antagonistic anti-DR3antibody of claim 17, further comprising a heavy chain constant region, wherein the monovalent antibody is conjugated with a lipophilic moiety having the formula (I)

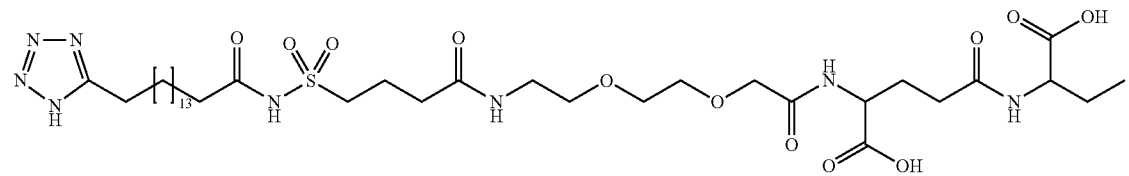

-continued
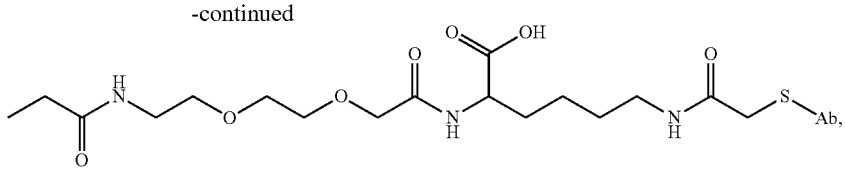
and wherein the lipophilic moiety is attached to a cysteine amino acid residue of the heavy chain constant region corresponding to Kabat residue 239 via a hydrophilic spacer.
23. The isolated monovalent antagonistic anti-DR3 antibody of claim 22, wherein the antibody is a Fab fragment.
* * * * *

UNITED STATES PATENT AND TRADEMARK OFFICE
CERTIFICATE OF CORRECTION

PATENT NO.        : 8,765,130 B2                                    Page 1 of 1
APPLICATION NO.   : 13/974275
DATED             : July 1, 2014
INVENTOR(S)       : Mette D. Andersen et al.

It is certified that error appears in the above-identified patent and that said Letters Patent is hereby corrected as shown below:

In the Claims

Please replace column 106, claim number 13, line number 33 with the following:

"...31-35 of SEQ ID NO:10; a heavy chain CDR2 comprising..."

Signed and Sealed this
Twentieth Day of January, 2015

Michelle K. Lee
*Deputy Director of the United States Patent and Trademark Office*

SEQUENCE LISTING

```
<160> NUMBER OF SEQ ID NOS: 29

<210> SEQ ID NO 1
<211> LENGTH: 417
<212> TYPE: PRT
<213> ORGANISM: homo sapiens

<400> SEQUENCE: 1

Met Glu Gln Arg Pro Arg Gly Cys Ala Ala Val Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
            35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
```

```
            290                 295                 300
Ser Arg Ala Leu Gly Pro Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
                340                 345                 350

Thr Leu Gly Leu Arg Glu Ala Glu Ile Glu Ala Val Glu Val Glu Ile
                355                 360                 365

Gly Arg Phe Arg Asp Gln Gln Tyr Glu Met Leu Lys Arg Trp Arg Gln
                370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro

<210> SEQ ID NO 2
<211> LENGTH: 276
<212> TYPE: PRT
<213> ORGANISM: Artificial Sequence
<220> FEATURE:
<223> OTHER INFORMATION: Synthetic

<400> SEQUENCE: 2

Gln Gly Gly Thr Arg Ser Pro Arg Cys Asp Cys Ala Gly Asp Phe His
1               5                   10                  15

Lys Lys Ile Gly Leu Phe Cys Cys Arg Gly Cys Pro Ala Gly His Tyr
            20                  25                  30

Leu Lys Ala Pro Cys Thr Glu Pro Cys Gly Asn Ser Thr Cys Leu Glu
        35                  40                  45

Ser Lys Tyr Gly Pro Pro Cys Pro Pro Cys Pro Ala Pro Glu Phe Leu
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240
```

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
            260                 265                 270

Ser Leu Gly Lys
        275

<210> SEQ ID NO 3
<211> LENGTH: 295
<212> TYPE: PRT
<213> ORGANISM: Artificial Sequence
<220> FEATURE:
<223> OTHER INFORMATION: Synthetic

<400> SEQUENCE: 3

Gln Gly Gly Thr Arg Ser Pro Arg Cys Asp Cys Ala Gly Asp Phe His
1               5                   10                  15

Lys Lys Ile Gly Leu Phe Cys Cys Arg Gly Cys Pro Ala Gly His Tyr
            20                  25                  30

Leu Lys Ala Pro Cys Thr Glu Pro Cys Gly Asn Ser Thr Cys Leu Val
        35                  40                  45

Cys Pro Gln Asp Thr Phe Leu Ala Trp Glu Asn His His Asn Ser Glu
50                  55                  60

Cys Ala Glu Ser Lys Tyr Gly Pro Pro Cys Pro Pro Cys Pro Ala Pro
65                  70                  75                  80

Glu Phe Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser Gln Glu Asp Pro Glu Val Gln Phe Asn Trp Tyr Val Asp
        115                 120                 125

Gly Val Glu Val His Asn Ala Lys Thr Lys Pro Arg Glu Glu Gln Phe
130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Gly Leu
                165                 170                 175

Pro Ser Ser Ile Glu Lys Thr Ile Ser Lys Ala Lys Gly Gln Pro Arg
            180                 185                 190

Glu Pro Gln Val Tyr Thr Leu Pro Pro Ser Gln Glu Glu Met Thr Lys
        195                 200                 205

Asn Gln Val Ser Leu Thr Cys Leu Val Lys Gly Phe Tyr Pro Ser Asp
210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Arg Leu Thr Val Asp Lys Ser Arg Trp Gln Glu Gly Asn Val Phe Ser
            260                 265                 270

Cys Ser Val Met His Glu Ala Leu His Asn His Tyr Thr Gln Lys Ser
        275                 280                 285

Leu Ser Leu Ser Leu Gly Lys
    290                 295

<210> SEQ ID NO 4

<211> LENGTH: 321
<212> TYPE: PRT
<213> ORGANISM: Artificial Sequence
<220> FEATURE:
<223> OTHER INFORMATION: Synthetic

<400> SEQUENCE: 4

```
Gln Gly Gly Thr Arg Ser Pro Arg Cys Asp Cys Ala Gly Asp Phe His
1               5                   10                  15

Lys Lys Ile Gly Leu Phe Cys Cys Arg Gly Cys Pro Ala Gly His Tyr
            20                  25                  30

Leu Lys Ala Pro Cys Thr Glu Pro Cys Gly Asn Ser Thr Cys Leu Val
        35                  40                  45

Cys Pro Gln Asp Thr Phe Leu Ala Trp Glu Asn His His Asn Ser Glu
50                  55                  60

Cys Ala Arg Cys Gln Ala Cys Asp Glu Gln Ala Ser Gln Val Ala Leu
65                  70                  75                  80

Glu Asn Cys Ser Ala Val Ala Asp Thr Arg Cys Gly Glu Ser Lys Tyr
                85                  90                  95

Gly Pro Pro Cys Pro Pro Cys Pro Ala Pro Glu Phe Leu Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser Gln Glu Asp
130                 135                 140

Pro Glu Val Gln Phe Asn Trp Tyr Val Asp Gly Val Glu Val His Asn
145                 150                 155                 160

Ala Lys Thr Lys Pro Arg Glu Glu Gln Phe Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Gly Leu Pro Ser Ser Ile Glu Lys
        195                 200                 205

Thr Ile Ser Lys Ala Lys Gly Gln Pro Arg Glu Pro Gln Val Tyr Thr
210                 215                 220

Leu Pro Pro Ser Gln Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Arg Leu Thr Val Asp Lys
        275                 280                 285

Ser Arg Trp Gln Glu Gly Asn Val Phe Ser Cys Ser Val Met His Glu
290                 295                 300

Ala Leu His Asn His Tyr Thr Gln Lys Ser Leu Ser Leu Ser Leu Gly
305                 310                 315                 320

Lys
```

<210> SEQ ID NO 5
<211> LENGTH: 344
<212> TYPE: PRT
<213> ORGANISM: Artificial Sequence
<220> FEATURE:
<223> OTHER INFORMATION: Synthetic

<400> SEQUENCE: 5

```
Gln Gly Gly Thr Arg Ser Pro Arg Cys Asp Cys Ala Gly Asp Phe His
1               5                   10                  15

Lys Lys Ile Gly Leu Phe Cys Cys Arg Gly Cys Pro Ala Gly His Tyr
            20                  25                  30

Leu Lys Ala Pro Cys Thr Glu Pro Cys Gly Asn Ser Thr Cys Leu Val
        35                  40                  45

Cys Pro Gln Asp Thr Phe Leu Ala Trp Glu Asn His His Asn Ser Glu
50                  55                      60

Cys Ala Arg Cys Gln Ala Cys Asp Glu Gln Ala Ser Gln Val Ala Leu
65                      70                  75                  80

Glu Asn Cys Ser Ala Val Ala Asp Thr Arg Cys Gly Cys Lys Pro Gly
                85                  90                  95

Trp Phe Val Glu Cys Gln Val Ser Gln Cys Val Ser Ser Pro Phe
                100                 105                 110

Tyr Cys Gln Glu Ser Lys Tyr Gly Pro Pro Cys Pro Pro Cys Pro Ala
        115                 120                 125

Pro Glu Phe Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser Gln Glu Asp Pro Glu Val Gln Phe Asn Trp Tyr Val
                165                 170                 175

Asp Gly Val Glu Val His Asn Ala Lys Thr Lys Pro Arg Glu Glu Gln
                180                 185                 190

Phe Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Gly
        210                 215                 220

Leu Pro Ser Ser Ile Glu Lys Thr Ile Ser Lys Ala Lys Gly Gln Pro
225                 230                 235                 240

Arg Glu Pro Gln Val Tyr Thr Leu Pro Pro Ser Gln Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
        290                 295                 300

Ser Arg Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Leu Gly Lys
            340

<210> SEQ ID NO 6
<211> LENGTH: 287
<212> TYPE: PRT
<213> ORGANISM: Artificial Sequence
<220> FEATURE:
<223> OTHER INFORMATION: Synthetic

<400> SEQUENCE: 6

Ser Pro Ile Leu Gly Tyr Trp Lys Ile Lys Gly Leu Val Gln Pro Thr
1               5                   10                  15
```

```
Arg Leu Leu Leu Glu Tyr Leu Glu Glu Lys Tyr Glu His Leu Tyr
         20                  25                  30

Glu Arg Asp Glu Gly Asp Lys Trp Arg Asn Lys Lys Phe Glu Leu Gly
             35                  40                  45

Leu Glu Phe Pro Asn Leu Pro Tyr Tyr Ile Asp Gly Asp Val Lys Leu
 50                  55                  60

Thr Gln Ser Met Ala Ile Ile Arg Tyr Ile Ala Asp Lys His Asn Met
 65                  70                  75                  80

Leu Gly Gly Ser Pro Lys Glu Arg Ala Glu Ile Ser Met Leu Glu Gly
                 85                  90                  95

Ala Val Leu Asp Ile Arg Tyr Gly Val Ser Arg Ile Ala Tyr Ser Lys
                100                 105                 110

Asp Phe Glu Thr Leu Lys Val Asp Phe Leu Ser Lys Leu Pro Glu Met
            115                 120                 125

Leu Lys Met Phe Glu Asp Arg Leu Ser His Lys Thr Tyr Leu Asn Gly
130                 135                 140

Asp His Val Thr His Pro Asp Phe Met Leu Tyr Asp Ala Leu Asp Val
145                 150                 155                 160

Val Leu Tyr Met Asp Pro Met Cys Leu Asp Ala Phe Pro Lys Leu Val
                165                 170                 175

Ser Phe Lys Lys Arg Ile Glu Ala Ile Pro Gln Ile Asp Lys Tyr Leu
            180                 185                 190

Lys Ser Ser Lys Tyr Ile Ala Trp Pro Leu Gln Gly Trp Gln Ala Thr
        195                 200                 205

Phe Gly Gly Gly Asp His Pro Pro Lys Ser Asp Leu Val Pro Arg Gly
210                 215                 220

Ser Pro Glu Phe Gln Gly Gly Thr Arg Ser Pro Arg Cys Asp Cys Ala
225                 230                 235                 240

Gly Asp Phe His Lys Lys Ile Gly Leu Phe Cys Cys Arg Gly Cys Pro
                245                 250                 255

Ala Gly His Tyr Leu Lys Ala Pro Cys Thr Glu Pro Cys Gly Asn Ser
            260                 265                 270

Thr Cys Leu Glu Phe Pro Gly Arg Leu Glu Arg Pro His Arg Asp
        275                 280                 285

<210> SEQ ID NO 7
<211> LENGTH: 411
<212> TYPE: PRT
<213> ORGANISM: Artificial Sequence
<220> FEATURE:
<223> OTHER INFORMATION: Synthetic

<400> SEQUENCE: 7

Gln Gly Gly Thr Arg Ser Pro Arg Cys Asp Cys Ala Gly Asp Phe His
 1               5                  10                  15

Lys Lys Ile Gly Leu Phe Cys Cys Arg Gly Cys Pro Ala Gly His Tyr
             20                  25                  30

Leu Lys Ala Pro Cys Thr Glu Pro Cys Gly Asn Ser Thr Cys Leu Val
         35                  40                  45

Cys Pro Gln Asp Thr Phe Leu Ala Trp Glu Asn His His Asn Ser Glu
 50                  55                  60

Cys Ala Arg Cys Gln Ala Cys Asp Glu Gln Ala Ser Gln Val Ala Leu
 65                  70                  75                  80

Glu Asn Cys Ser Ala Val Ala Asp Thr Arg Cys Gly Cys Lys Pro Gly
                 85                  90                  95
```

```
Trp Phe Val Glu Cys Gln Val Ser Gln Cys Val Ser Ser Pro Phe
                100                 105                 110

Tyr Cys Gln Pro Cys Leu Asp Cys Gly Ala Leu His Arg His Thr Arg
            115                 120                 125

Leu Leu Cys Ser Arg Arg Asp Thr Asp Cys Gly Thr Cys Leu Pro Gly
        130                 135                 140

Phe Tyr Glu His Gly Asp Gly Cys Val Ser Cys Pro Thr Ser Thr Leu
145                 150                 155                 160

Gly Ser Cys Pro Glu Arg Cys Ala Ala Val Cys Gly Trp Arg Gln Glu
                165                 170                 175

Asn Leu Tyr Phe Gln Gly Glu Ser Lys Tyr Gly Pro Pro Cys Pro Pro
            180                 185                 190

Cys Pro Ala Pro Glu Phe Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser Gln Glu Asp Pro Glu Val Gln Phe Asn
225                 230                 235                 240

Trp Tyr Val Asp Gly Val Glu Val His Asn Ala Lys Thr Lys Pro Arg
                245                 250                 255

Glu Glu Gln Phe Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Gly Leu Pro Ser Ser Ile Glu Lys Thr Ile Ser Lys Ala Lys
    290                 295                 300

Gly Gln Pro Arg Glu Pro Gln Val Tyr Thr Leu Pro Pro Ser Gln Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Arg Leu Thr Val Asp Lys Ser Arg Trp Gln Glu Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Leu Gly Lys
                405                 410

<210> SEQ ID NO 8
<211> LENGTH: 119
<212> TYPE: PRT
<213> ORGANISM: Artificial Sequence
<220> FEATURE:
<223> OTHER INFORMATION: Synthetic

<400> SEQUENCE: 8

Glu Val Gln Leu Val Glu Ser Gly Gly Asp Phe Val Lys Pro Gly Gly
1               5                   10                  15

Ser Leu Lys Leu Ser Cys Ala Ala Ser Gly Phe Thr Phe Asn Asn Tyr
            20                  25                  30

Gly Met Ser Trp Val Arg Gln Thr Pro Asp Lys Arg Leu Glu Trp Val
        35                  40                  45
```

```
Ala Ala Ile Ser Ser Gly Val Thr Tyr Thr Tyr Tyr Pro Asp Thr Val
        50                   55                   60

Lys Gly Arg Phe Thr Ile Ser Arg Asp Asn Ala Lys Asn Thr Leu Tyr
 65                   70                   75                  80

Leu His Met Ser Ser Leu Lys Ser Glu Asp Thr Ala Met Tyr Tyr Cys
                 85                   90                   95

Gly Arg His Asp Asp Tyr Gly Asn His Phe Asp Tyr Trp Gly Gln Gly
                100                  105                 110

Thr Thr Leu Thr Val Ser Ser
            115
```

<210> SEQ ID NO 9
<211> LENGTH: 114
<212> TYPE: PRT
<213> ORGANISM: Artificial Sequence
<220> FEATURE:
<223> OTHER INFORMATION: Synthetic

<400> SEQUENCE: 9

```
Asp Ile Val Met Thr Gln Ser Pro Ser Ser Leu Ala Met Ser Leu Gly
 1               5                   10                  15

Gln Arg Val Thr Met Asn Cys Lys Ser Ser Gln Ser Leu Leu Asn Ser
                20                  25                  30

His Asn Gln Lys Asn Tyr Leu Ala Trp Tyr Gln Lys Pro Gly Gln
             35                  40                  45

Ser Pro Lys Leu Leu Val Tyr Phe Ala Ser Arg Glu Ser Gly Val
         50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Phe Thr Phe Gly Ser Gly Thr Lys Leu Glu Ile
                100                 105                 110

Lys Arg
```

<210> SEQ ID NO 10
<211> LENGTH: 120
<212> TYPE: PRT
<213> ORGANISM: Artificial Sequence
<220> FEATURE:
<223> OTHER INFORMATION: Synthetic

<400> SEQUENCE: 10

```
Glu Val Lys Leu Val Glu Ser Gly Gly Gly Leu Val Lys Pro Gly Gly
 1               5                   10                  15

Ser Leu Lys Leu Ser Cys Ser Ala Ser Gly Phe Ala Phe Ser Asn Tyr
                20                  25                  30

Asp Met Ser Trp Val Arg Gln Thr Pro Glu Lys Arg Leu Glu Trp Val
            35                  40                  45

Ala Ala Phe Ser Ser Asp Gly Tyr Thr Phe Tyr Pro Asp Ser Leu Lys
        50                  55                  60

Gly Arg Phe Thr Ile Ser Arg Asp Asn Ala Arg Asn Thr Leu Tyr Leu
 65                  70                  75                  80

Gln Met Ser Ser Leu Gly Ser Glu Asp Thr Ala Leu Tyr Cys Cys Ala
                 85                  90                  95

Arg His Ala Asp Tyr Ala Asn Tyr Pro Val Met Asp Tyr Trp Gly Gln
                100                 105                 110
```

```
Gly Thr Ser Val Thr Val Ser Ser
        115                 120

<210> SEQ ID NO 11
<211> LENGTH: 112
<212> TYPE: PRT
<213> ORGANISM: Artificial Sequence
<220> FEATURE:
<223> OTHER INFORMATION: Synthetic

<400> SEQUENCE: 11

Asp Ile Val Leu Ala Gln Ser Pro Ala Ser Leu Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Met Leu Glu Leu Lys Arg
            100                 105                 110

<210> SEQ ID NO 12
<211> LENGTH: 122
<212> TYPE: PRT
<213> ORGANISM: Artificial Sequence
<220> FEATURE:
<223> OTHER INFORMATION: Synthetic

<400> SEQUENCE: 12

Glu Val Lys Val Val Glu Ser Gly Gly Gly Leu Val Lys Pro Gly Gly
1               5                   10                  15

Ser Leu Lys Leu Ser Cys Ala Ala Ser Gly Phe Val Phe Ser Ser Tyr
            20                  25                  30

Asp Met Ser Trp Val Arg Gln Ile Pro Glu Lys Arg Leu Glu Trp Val
        35                  40                  45

Ala Ala Ile Ser Ser Gly Asp Tyr Tyr Thr Tyr Tyr Pro Asp Ser Val
    50                  55                  60

Lys Gly Arg Phe Thr Ile Ser Arg Asp Asp Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg His Arg Gly Gly Asn Tyr Pro Gln Tyr Ala Met Asp Tyr Trp
            100                 105                 110

Gly Gln Gly Thr Ser Val Thr Val Ser Ser
        115                 120

<210> SEQ ID NO 13
<211> LENGTH: 112
<212> TYPE: PRT
<213> ORGANISM: Artificial Sequence
<220> FEATURE:
<223> OTHER INFORMATION: Synthetic

<400> SEQUENCE: 13
```

Asp Ile Leu Leu Thr Gln Ser Pro Ala Ser Phe Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Asn Tyr Ile His Trp Tyr Gln Gln Lys Pro Gly Gln Pro Pro
        35                  40                  45

Lys Leu Leu Ile Tyr Leu Thr Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
            85                  90                  95

Glu Leu Pro Phe Thr Phe Gly Ser Gly Thr Lys Leu Glu Ile Lys Arg
        100                 105                 110

<210> SEQ ID NO 14
<211> LENGTH: 227
<212> TYPE: PRT
<213> ORGANISM: Artificial Sequence
<220> FEATURE:
<223> OTHER INFORMATION: Synthetic

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Val
        35                  40                  45

Ser Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Asn Cys
            85                  90                  95

Ala Arg Arg Lys Asp Gly Asn Tyr Tyr Tyr Ala Met Asp Tyr Trp Gly
        100                 105                 110

Gln Gly Thr Thr Val Thr Val Ser Ser Ala Ser Thr Lys Gly Pro Ser
    115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
210                 215                 220

Pro Pro Ser
225

<210> SEQ ID NO 15
<211> LENGTH: 218

```
<212> TYPE: PRT
<213> ORGANISM: Artificial Sequence
<220> FEATURE:
<223> OTHER INFORMATION: Synthetic

<400> SEQUENCE: 15

Asp Ile Val Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Glu Asp Pro Trp Thr Phe Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 16
<211> LENGTH: 226
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Thr Gly Lys Gly Leu Glu Trp Val
        35                  40                  45

Ala Ala Phe Ser Ser Asp Gly Tyr Thr Phe Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg His Ala Asp Tyr Ala Asn Tyr Pro Val Met Asp Tyr Trp Gly Gln
            100                 105                 110
```

```
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys
225

<210> SEQ ID NO 17
<211> LENGTH: 218
<212> TYPE: PRT
<213> ORGANISM: Artificial Sequence
<220> FEATURE:
<223> OTHER INFORMATION: Synthetic

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 18
```

<211> LENGTH: 123
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Asp Lys Arg Leu Glu Trp Val
        35                  40                  45

Ala Glu Ile Ser Ser Gly Asp Thr Tyr Thr Tyr Tyr Pro Asp Thr Val
    50                  55                  60

Thr Gly Arg Phe Thr Ile Ser Arg Asp Asn Ala Lys Lys Thr Leu Tyr
65                  70                  75                  80

Leu Glu Met Ser Gly Leu Arg Ser Glu Asp Thr Ala Met Tyr Tyr Cys
                85                  90                  95

Ala Arg Asp Arg Glu Ala Tyr Tyr Gly Gln Gln Tyr Val Met Asp Tyr
            100                 105                 110

Trp Gly Gln Gly Thr Ser Val Thr Val Ser Ser
        115                 120
```

<210> SEQ ID NO 19
<211> LENGTH: 112
<212> TYPE: PRT
<213> ORGANISM: Artificial Sequence
<220> FEATURE:
<223> OTHER INFORMATION: Synthetic

<400> SEQUENCE: 19

```
Asp Ile Val Leu Thr Gln Ser Pro Ala Ser Leu Ala Val Ser Leu Gly
1               5                   10                  15

Leu Ser Val Thr Ile Ser Cys Arg Ala Ser Glu Ser Ile Glu Tyr Ser
            20                  25                  30

Gly Thr Ser Phe Leu Gln Trp Tyr Gln Gln Lys Pro Gly Gln Pro Pro
        35                  40                  45

Arg Leu Leu Ile Tyr Gly Ser Ser Thr Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ser Ala Met Tyr Phe Cys Gln Gln Ser Arg
                85                  90                  95

Arg Leu Pro Trp Thr Phe Gly Gly Gly Thr Lys Leu Glu Ile Lys Arg
            100                 105                 110
```

<210> SEQ ID NO 20
<211> LENGTH: 123
<212> TYPE: PRT
<213> ORGANISM: Artificial Sequence
<220> FEATURE:
<223> OTHER INFORMATION: Synthetic

<400> SEQUENCE: 20

```
Glu Val Gln Leu Val Glu Ser Gly Gly Asp Leu Val Met Pro Gly Gly
1               5                   10                  15

Ser Leu Lys Leu Ser Cys Ala Ala Ser Gly Phe Ile Phe Ser Ser Tyr
            20                  25                  30
```

Gly Leu Ser Trp Ile Arg Gln Thr Pro Asp Lys Arg Leu Glu Trp Val
            35                  40                  45

Ala Thr Ile Ser Gly Gly Asp Ser Tyr Thr Tyr Tyr Pro Asp Ser Val
 50                      55                  60

Lys Gly Arg Phe Thr Ile Ser Ser Asp Asn Ala Lys Asn Thr Leu Tyr
 65                  70                  75                  80

Leu Gln Met Thr Ser Leu Lys Ser Glu Asp Thr Ala Met Tyr Tyr Cys
                85                  90                  95

Ala Thr Gln Arg Glu Ile Tyr Tyr Gly Thr Tyr Tyr Ala Leu Asp His
            100                 105                 110

Trp Gly Gln Gly Thr Ser Val Thr Val Ser Ser
            115                 120

<210> SEQ ID NO 21
<211> LENGTH: 108
<212> TYPE: PRT
<213> ORGANISM: Artificial Sequence
<220> FEATURE:
<223> OTHER INFORMATION: Synthetic

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
 50                     55                  60

Ser Gly Ser Gly Thr Asp Tyr Ser Leu Thr Ile Ser Ser Leu Glu Gln
 65                 70                  75                  80

Asp Asp Ile Ala Thr Tyr Phe Cys Gln Gln Gly Ser Pro Leu Pro Trp
                85                  90                  95

Thr Phe Gly Gly Gly Thr Lys Leu Glu Ile Lys Arg
            100                 105

<210> SEQ ID NO 22
<211> LENGTH: 123
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Glu Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Ser Pro Glu Lys Arg Leu Glu Trp Val
        35                  40                  45

Ala Glu Ile Ser Ser Gly Asp Ser Tyr Thr Tyr Tyr Pro Asp Ile Val
 50                     55                  60

Thr Gly Arg Phe Thr Ile Ser Arg Asp Asp Ala Lys Asn Thr Leu Phe
 65                 70                  75                  80

Leu Glu Met Ser Ser Leu Arg Ser Glu Asp Thr Ala Ile Tyr Tyr Cys
                85                  90                  95

Val Arg Asp Gln Asp Tyr Arg Tyr Asp Gly Tyr Tyr Ala Met Asp His
            100                 105                 110

```
Trp Gly Gln Gly Thr Ser Val Thr Val Ser Ser
        115                 120

<210> SEQ ID NO 23
<211> LENGTH: 112
<212> TYPE: PRT
<213> ORGANISM: Artificial Sequence
<220> FEATURE:
<223> OTHER INFORMATION: Synthetic

<400> SEQUENCE: 23

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu His Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Arg Gly Ser Gly Pro Asp Phe Ser Leu Asn Ile His
65                  70                  75                  80

Pro Val Glu Glu Asp Asp Ile Ala Met Tyr Phe Cys Gln Gln Ser Arg
                85                  90                  95

Arg Ile Pro Trp Thr Phe Gly Gly Gly Thr Lys Leu Glu Ile Lys Arg
            100                 105                 110

<210> SEQ ID NO 24
<211> LENGTH: 118
<212> TYPE: PRT
<213> ORGANISM: Artificial Sequence
<220> FEATURE:
<223> OTHER INFORMATION: Synthetic

<400> SEQUENCE: 24

Glu Val Gln Leu Val Glu Ser Gly Gly Gly Leu Val Lys Pro Gly Gly
1               5                   10                  15

Ser Leu Lys Phe Ser Cys Ala Val Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Ala Ile Ser Ser Asp Ser Thr Tyr Thr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Thr Arg Ser Asp Ala Met Asp Tyr Trp Gly Gln Gly Thr
            100                 105                 110

Ser Val Thr Val Ser Ser
        115

<210> SEQ ID NO 25
<211> LENGTH: 112
<212> TYPE: PRT
<213> ORGANISM: Artificial Sequence
<220> FEATURE:
<223> OTHER INFORMATION: Synthetic

<400> SEQUENCE: 25
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Ile Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

<210> SEQ ID NO 26
<211> LENGTH: 126
<212> TYPE: PRT
<213> ORGANISM: Artificial Sequence
<220> FEATURE:
<223> OTHER INFORMATION: Synthetic

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asn Tyr
            20                  25                  30

Tyr Met Ala Trp Val Arg Lys Pro Pro Gly Lys Thr Leu Glu Trp Leu
        35                  40                  45

Gly Phe Met Arg Asn Ile Val Asn Gly Tyr Thr Thr Asp Tyr Ser Gly
    50                  55                  60

Ser Val Glu Gly Arg Phe Thr Ile Ser Arg Asp Asn Ser Gln Ser Ile
65                  70                  75                  80

Leu Tyr Leu Gln Met Asn Ala Leu Arg Pro Glu Asp Ser Ala Thr Tyr
                85                  90                  95

Tyr Cys Ala Arg Asp Ile Gly Tyr Arg Tyr Asp Gly Gly Tyr Gly Gly
            100                 105                 110

Leu Asp Tyr Trp Gly Gln Gly Thr Ser Val Thr Val Ser Ser
        115                 120                 125

<210> SEQ ID NO 27
<211> LENGTH: 108
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ala Ser Leu Ser Ala Ser Val Gly
1               5                   10                  15

Glu Thr Val Thr Leu Thr Cys Arg Ala Ser Gly Asn Ile His Asn Tyr
            20                  25                  30

Leu Thr Trp Tyr Gln Gln Lys Gln Gly Lys Ser Pro Gln Leu Leu Val
        35                  40                  45

Tyr Asn Val Lys Thr Leu Ala Asp Gly Val Ser Ser Arg Phe Ser Gly
    50                  55                  60

Ser Gly Ser Gly Thr Gln Phe Ser Leu Lys Ile Asn Ser Leu Gln Pro
65                  70                  75                  80

```
Glu Asp Phe Gly Ser Tyr Tyr Cys Gln His Phe Trp Thr Thr Pro Tyr
                85                  90                  95

Thr Phe Gly Gly Gly Thr Lys Leu Glu Ile Arg Arg
            100                 105

<210> SEQ ID NO 28
<211> LENGTH: 120
<212> TYPE: PRT
<213> ORGANISM: Artificial Sequence
<220> FEATURE:
<223> OTHER INFORMATION: Synthetic

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Thr Gly Lys Gly Leu Glu Trp Val
        35                  40                  45

Ser Ala Phe Ser Ser Asp Gly Tyr Thr Phe Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg His Ala Asp Tyr Ala Asn Tyr Pro Val Met Asp Tyr Trp Gly Gln
            100                 105                 110

Gly Thr Leu Val Thr Val Ser Ser
        115                 120

<210> SEQ ID NO 29
<211> LENGTH: 111
<212> TYPE: PRT
<213> ORGANISM: Artificial Sequence
<220> FEATURE:
<223> OTHER INFORMATION: Synthetic

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Leu Thr Phe Gly Gly Gly Thr Lys Val Glu Ile Lys
            100                 105                 110
```